US012599560B2

(12) United States Patent
Zhang et al.

(10) Patent No.: US 12,599,560 B2
(45) Date of Patent: Apr. 14, 2026

(54) LIPIDS AND LIPID NANOPARTICLE FORMULATIONS

(71) Applicant: Longuide Biopharma Corporation, Shenzhen (CN)

(72) Inventors: Longgui Zhang, Shenzhen (CN); Yuebao Zhang, Shenzhen (CN); Chen Liu, Shenzhen (CN); Xiuting Xu, Shenzhen (CN); Yan Wang, Shenzhen (CN); Meigui Liang, Shenzhen (CN); Yuanyuan Xu, Shenzhen (CN); Wenting Song, Shenzhen (CN); Zehao Liao, Shenzhen (CN); Qinying Zhu, Shenzhen (CN); Yingxin Lu, Shenzhen (CN)

(73) Assignee: Longuide Biopharma Corporation, Shenzhen (CN)

(*) Notice: Subject to any disclaimer, the term of this patent is extended or adjusted under 35 U.S.C. 154(b) by 238 days.

(21) Appl. No.: 18/532,785

(22) Filed: Dec. 7, 2023

(65) Prior Publication Data

US 2025/0152510 A1 May 15, 2025

(30) Foreign Application Priority Data

Nov. 2, 2023 (WO) ................ PCT/CN2023/129327
Nov. 8, 2023 (WO) ................ PCT/CN2023/130500

(51) Int. Cl.

| | |
|---|---|
| ***A61K 9/127*** | (2006.01) |
| ***A61K 9/1271*** | (2025.01) |
| ***A61K 45/06*** | (2006.01) |
| ***C07C 229/32*** | (2006.01) |
| ***C07C 235/06*** | (2006.01) |
| ***C07C 323/03*** | (2006.01) |
| ***C07D 295/125*** | (2006.01) |

(52) U.S. Cl.

CPC ............ *A61K 9/1271* (2013.01); *A61K 45/06* (2013.01); *C07C 229/32* (2013.01); *C07C 235/06* (2013.01); *C07C 323/03* (2013.01); *C07D 295/125* (2013.01)

(58) Field of Classification Search

CPC .... A61K 9/1271; A61K 45/06; A61K 9/5123; C07C 229/32; C07C 235/06; C07C 323/03; C07C 237/06; C07C 2601/14; C07C 229/22; C07D 295/125; C07D 295/13; C07B 2200/07

See application file for complete search history.

(56) References Cited

FOREIGN PATENT DOCUMENTS

| | | |
|---|---|---|
| WO | WO2012068176 | 5/2012 |
| WO | WO 2018089801 A1 | 5/2018 |
| WO | WO2019036028 | 2/2019 |
| WO | WO 2019246203 A1 | 12/2019 |
| WO | WO 2020257611 A1 | 12/2020 |
| WO | WO 2022066916 A1 | 3/2022 |
| WO | WO 2022221688 A1 | 10/2022 |
| WO | WO2023078946 | 5/2023 |
| WO | WO2023078950 | 5/2023 |
| WO | WO2023091787 | 5/2023 |
| WO | WO 2023178167 A1 | 9/2023 |

OTHER PUBLICATIONS

International Search Report and Written Opinion dated Jul. 4, 2024, for PCT International Patent Application No. PCT/CN2023/129327, 10 pages.

*Primary Examiner* — Kamal A Saeed
*Assistant Examiner* — Meghan C Heasley
(74) *Attorney, Agent, or Firm* — Sheppard, Mullin, Richter & Hampton LLP

(57) ABSTRACT

The present disclosure relates generally to lipids, lipid nanoparticle formulations, and methods of using the same for delivering nucleic acids, such as mRNA.

20 Claims, No Drawings

LIPIDS AND LIPID NANOPARTICLE FORMULATIONS

CROSS REFERENCE TO RELATED APPLICATIONS

This application claims the benefit under 35 U.S.C. § 119(d) of Chinese Patent Application Nos. PCT/CN2023/130500 filed Nov. 8, 2023, and PCT/CN2023/129327 filed Nov. 2, 2023, the contents of each of which are hereby incorporated by reference in their entirety into the instant application.

BACKGROUND

Lipid nanoparticles (LNPs) are now used in the development and delivery of mRNA-based vaccines as they serve as carriers or vehicles for delivering the mRNA (messenger RNA) into cells, allowing them to instruct the cells to produce a specific protein, such as a viral antigen, to trigger an immune response.

The lipids are an essential component in LNPs, encapsulating nucleic acids and other components. In classical formulations, more than one lipid is required, such as an ionizable cationic lipid, a helper lipid, cholesterol, and a PEG-lipid. The classical liposome usually required cholesterol and phospholipids, sometimes accompanied by some additional, minor components. The lipids used, and molar ratio of each, can dictate the diameter, encapsulation of nucleic acids, zeta potential, and the length of encapsulated nucleic acids. The inclusion of novel lipids requires individual optimization. In addition, the structure and composition of lipids can also dictate which tissue is targeted.

As such, alternative lipid structures are required to further the field of this important nucleic acid delivery platform.

SUMMARY

In one aspect, provided is a compound of Formula I:

I

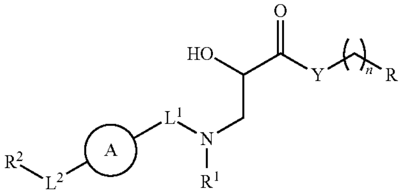

or a pharmaceutically acceptable salt, stereoisomer, or mixture of stereoisomers thereof, wherein:

Ring A is $C_{3-10}$ cycloalkyl, heterocyclyl, aryl, or heteroaryl;

$L^1$ is a bond, $C_{1-10}$ alkylene, or $C_{2-10}$ heteroalkylene;

$L^2$ is a bond, $C_{1-10}$ alkylene, or $C_{2-10}$ heteroalkylene;

$R^1$ is hydrogen, $C_{1-20}$ alkyl, $C_{2-20}$ alkenyl, $C_{2-20}$ alkynyl, $C_{2-20}$ heteroalkyl,

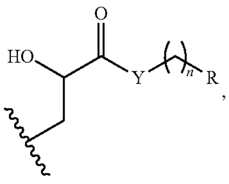

,

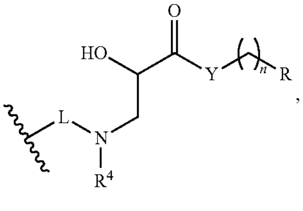

, or

-continued

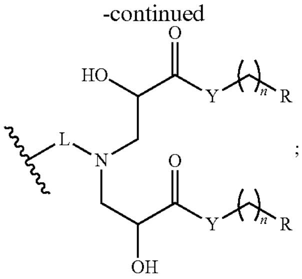

;

wherein the $C_{1-20}$ alkyl, $C_{2-20}$ alkenyl, $C_{2-20}$ alkynyl, or $C_{2-20}$ heteroalkyl is independently optionally substituted with one to five halo, cyano, —$OR^4$, —$SR^4$, —$NR^4_2$, —$N(R^4)_3^+$, oxo, $C_{1-6}$ alkyl, $C_{2-6}$ alkenyl, $C_{2-6}$ alkynyl, or $C_{1-6}$haloalkyl;

$R^2$ is

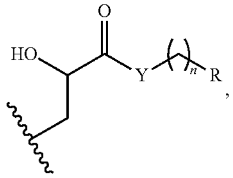

,

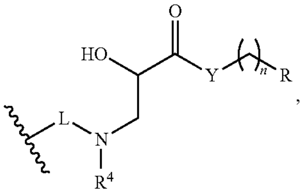

,

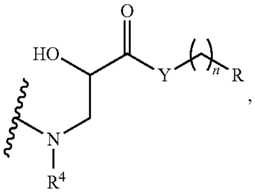

, or

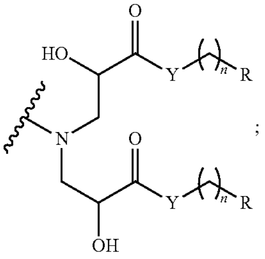

;

L is $C_{1-10}$ alkylene or $C_{3-10}$ heteroalkylene;

each $R^4$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —$SR^5$, —$NR^5_2$, —$N(R^5)_3^+$, or oxo;

each $R^5$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —SH, —$NH_2$, —$NH(C_{1-6}$ alkyl), —$N(C_{1-6}$ alkyl$)_2$, —$N(C_{1-6}$ alkyl$)_3^+$, or oxo;

each Y is independently —O— or —$NR^7$—;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —NH($C_{1-6}$ alkyl), —N($C_{1-6}$ alkyl)$_2$, —N($C_{1-6}$ alkyl)$_3^+$, oxo, $C_{1-6}$ alkoxy, or $C_{1-6}$ haloalkoxy;

each n is independently an integer from 1-20;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2$$NR^4$—;

each $Z^1$ is independently —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2$$NR^4$—; and provided that each

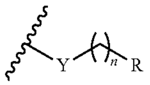

moiety comprises at least 6 linear atoms.

Also provided herein is a lipid nanoparticle comprising one or more of the compounds as disclosed herein. In some embodiments, the compounds disclosed herein can be used alone, or in combination with other lipid components, such as neutral lipids, charged lipids, steroids (including for example, all sterols) and/or their analogs, and/or polymer conjugated lipids, to form lipid nanoparticles for the delivery of therapeutic agents. In some embodiments, the lipid nanoparticles are used to deliver nucleic acids such as antisense and/or messenger RNA. Methods for using such lipid nanoparticles for treatment or prevention of various diseases or conditions, such as those caused by infectious entities and/or insufficiency of a protein, are also provided.

Pharmaceutical compositions comprising a lipid nanoparticle composition as disclosed herein and a therapeutic agent are also provided. In some embodiments, the pharmaceutical compositions further comprise one or more components selected from neutral lipids, charged lipids, steroids and polymer conjugated lipids. Such compositions are useful for formation of lipid nanoparticles for the delivery of the therapeutic agent.

Also provided herein is a method of delivering an mRNA to a mammalian cell, the method comprising administering to a subject a composition comprising a lipid nanoparticle comprising a compound as disclosed herein and an mRNA.

Also provided herein is a method for preventing a disease or disorder, comprising administering a lipid nanoparticle as disclosed herein to a subject in need thereof, wherein the lipid nanoparticle comprises one or more therapeutic or prophylactic agent such as mRNA.

DETAILED DESCRIPTION

Definitions

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)$NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes i-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group $—C(O)NR^yR^z$ and an "N-amido" group which refers to the group $—NR^yC(O)R^z$, wherein $R^y$ and $R^z$ are independently selected from the group consisting of hydrogen, alkyl, aryl, haloalkyl, or heteroaryl; each of which may be optionally substituted.

"Amino" refers to the group $—NR^yR^z$ wherein $R^y$ and $R^z$ are independently selected from the group consisting of hydrogen, alkyl, haloalkyl, aryl, or heteroaryl; each of which may be optionally substituted.

"Amidino" refers to $—C(NH)(NH_2)$.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-2}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to $—N_3$.

"Carbamoyl" refers to both an "O-carbamoyl" group which refers to the group $—O—C(O)NR^yR^z$ and an "N-carbamoyl" group which refers to the group $—NR^yC(O)OR^z$, wherein $R^y$ and $R^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Guanidino" refers to $—NHC(NH)(NH_2)$.

"Hydrazino" refers to $—NHNH_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, w % here a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl ($—CHF_2$) and trifluoromethyl ($—CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group, e.g., a "$C_{2-10}$ heteroalkyl" group comprises 3 to 9 carbon atoms and 1 to 3 heteroatoms, such that the number of carbon+heteroatoms atoms in the heteroalkyl chain is from 2 to 10. Heteroatomic groups include, but are not limited to, —NR—, —O—, —S—, —S(O)—, $—S(O)_2—$, and the like, where R is H, alkyl, aryl, cycloalkyl, heteroalkyl, heteroaryl or heterocyclyl, each of which may be optionally substituted. "Heteroalkylene" refers to a divalent heteroalkyl group. "Heteroalkylene" groups must have at least one carbon and at least one heteroatomic group within the chain. Non-limiting examples of heteroalkyl groups include $—CH_2OCH_2—$, $OCH_2—$, $—CH(CH_3)OCH_2—$, $—CH_2CH_2OCH_2—$, $—CH_2CH_2OCH_2CH_2OCH_2—$, $—CH_2SCH_2—$, $—CH(CH_3)SCH_2—$, $—CH_2CH_2SCH_2—$, $—CH_2CH_2SCH_2CH_2SCH_2—$, $—CH_2S(O)_2CH_2—$, $—CH(CH_3)S(O)_2CH_2—$, $—CH_2CH_2S(O)_2CH_2—$, $—CH_2CH_2S(O)_2CH_2CH_2OCH_2—$, $—CH_2NR^yCH_2—$, $—NR^yCH_2CH_2—$, $—CH(CH_3)NR^yCH_2—$, $—CH_2CH_2NR^yCH_2—$, $—CH_2CH_2NR^yCH_2CH_2NR^yCH_2—$, etc., where $R^y$ is hydrogen, alkyl, alkenyl, alkynyl, cycloalkyl, heterocyclyl, aryl, heteroalkyl, or heteroaryl; each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazoyl, Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocycyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Hydroxy" or "hydroxyl" refers to the group —OH.

"Oxo" refers to the group (=O) or (O).

"Nitro" refers to the group $—NO_2$.

"Sulfonyl" refers to the group $—S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl, "Alkylsulfonyl" refers to the group $—S(O)_2R$, where R is alkyl.

"Alkylsulfinyl" refers to the group —S(O)R, where R is alkyl.

"Thiocyanate" refers to the group —SCN.

"Thiol" refers to the group —SH.

"Thioxo" or "thione" refer to the group (=S) or (S).

Certain commonly used alternative chemical names may be used. For example, a divalent group such as a divalent "alkyl" group, a divalent "heteroalkyl" group, a divalent "aryl" group, etc., may also be referred to as "alkylene", "heteroalkylene", "arylene", respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN$(alkyl)_2$), trialkyl amines (i.e., N$(alkyl)_3$), substituted alkyl amines (i.e., $NH_2$(substituted alkyl)), di(substituted alkyl) amines (i.e., HN$(substituted\ alkyl)_2$), tri (substituted alkyl) amines (i.e., N$(substituted\ alkyl)_3$), alkenyl amines (i.e., $NH_2$(alkenyl)), dialkenyl amines (i.e., HN$(alkenyl)_2$), trialkenyl amines (i.e., N$(alkenyl)_3$), substituted alkenyl amines (i.e., $NH_2$(substituted alkenyl)), di(substituted alkenyl) amines (i.e., HN$(substituted\ alkenyl)_2$), tri(substituted alkenyl) amines (i.e., N$(substituted\ alkenyl)_3$, mono-, di- or tri-cycloalkyl amines (i.e., $NH_2$(cycloalkyl), HN$(cycloalkyl)_2$, N$(cycloalkyl)_3$), mono-, di- or tri-arylamines (i.e., $NH_2$(aryl), HN$(aryl)_2$, N$(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

As used herein, "encapsulation efficiency" refers to the amount of a therapeutic and/or prophylactic that becomes part of a nanoparticle composition, relative to the initial total amount of therapeutic and/or prophylactic used in the preparation of a nanoparticle composition. For example, if 97 mg of therapeutic and/or prophylactic are encapsulated in a nanoparticle composition out of a total 100 mg of therapeutic and/or prophylactic initially provided to the composition, the encapsulation efficiency may be given as 97%. As used herein, "Encapsulation" may refer to complete, substantial, or partial enclosure, confinement, surrounding, or encasement.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cisltrans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

As used herein, a "lipid component" is that component of a nanoparticle composition that includes one or more lipids. For example, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety. As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, the "N:P ratio" is the molar ratio of ionizable (in the physiological pH range) nitrogen atoms in a lipid to phosphate groups in an RNA, e.g., in a nanoparticle composition including a lipid component and an RNA.

As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxy toluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term “crystal polymorphs”, “polymorphs” or “crystal forms” means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility.

Recrystallization solvent, rate of crystallization, storage temperature, and other factors may cause one crystal form to dominate. Crystal polymorphs of the compounds can be prepared by crystallization under different conditions.

Compositions may also include salts of one or more compounds. Salts may be pharmaceutically acceptable salts. As used herein, “pharmaceutically acceptable salts” refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like.

Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington’s Pharmaceutical Sciences, $17^{th}$ ed., Mack Publishing Company, Easton, Pa., 1985, p. 1418, Pharmaceutical Salts: Properties, Selection, and Use, P. H. Stahl and C. G Wermuth (eds.), Wiley-VCH, 2008, and Berge et al, Journal of Pharmaceutical Science, 66, 1-19 (1977), each of which is incorporated herein by reference in its entirety.

Compounds

In one aspect, provided is a compound of Formula I:

I

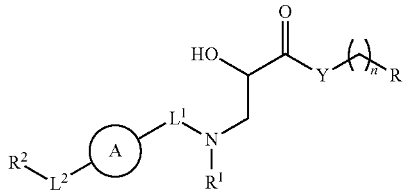

or a pharmaceutically acceptable salt, stereoisomer, or mixture of stereoisomers thereof, wherein:

Ring A is $C_{3-10}$ cycloalkyl, heterocyclyl, aryl, or heteroaryl;

$L^1$ is a bond, $C_{1-10}$ alkylene, or $C_{2-10}$ heteroalkylene;

$L^2$ is a bond, $C_{1-10}$ alkylene, or $C_{2-10}$ heteroalkylene;

$R^1$ is hydrogen, $C_{1-20}$ alkyl, $C_{2-20}$ alkenyl, $C_{2-20}$ alkynyl, $C_{2-20}$ heteroalkyl,

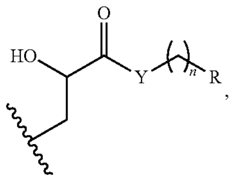,
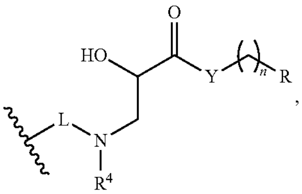, or

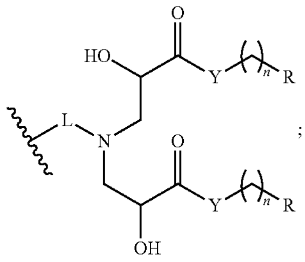;

wherein the $C_{1-20}$ alkyl, $C_{2-20}$ alkenyl, $C_{2-20}$ alkynyl, or $C_{2-20}$ heteroalkyl is independently optionally substituted with one to five halo, cyano, —$OR^4$, —$SR_4$, —$NR^4_2$, —$N(R^4)_3^+$, oxo, $C_{1-6}$ alkyl, $C_{2-6}$ alkenyl, $C_{2-6}$ alkynyl, or $C_{1-6}$haloalkyl;

$R^2$ is 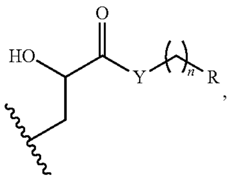,

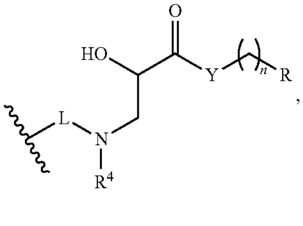,

-continued

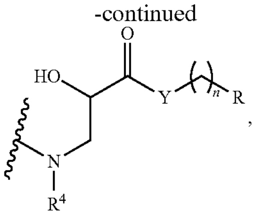

, or

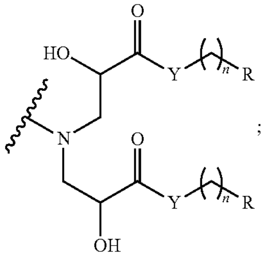

;

L is $C_{1-10}$ alkylene or $C_{3-10}$ heteroalkylene;

each $R^4$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —$SR_5$, —$NR^5_2$, —$N(R^5)_3^+$, or oxo;

each $R^5$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —SH, —$NH_2$, —$NH(C_{1-6}$ alkyl), —$N(C_{1-6}$ alkyl$)_2$, —$N(C_{1-6}$ alkyl$)_3^+$, or oxo;

each Y is independently —O— or —$NR^7$—;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —$NH(C_{1-6}$ alkyl), —$N(C_{1-6}$ alkyl$)_2$, —$N(C_{1-6}$ alkyl$)_3^+$, oxo, $C_{1-6}$ alkoxy, or $C_{1-6}$ haloalkoxy;

each n is independently an integer from 1-20;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—;

each $Z^1$ is independently —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—; and provided that each

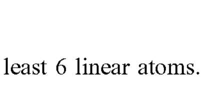

moiety comprises at least 6 linear atoms.

In one aspect, provided is a compound of Formula I:

I

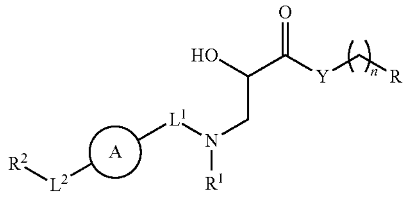

or a pharmaceutically acceptable salt, stereoisomer, or mixture of stereoisomers thereof, wherein:

Ring A is $C_{3-10}$ cycloalkyl, heterocyclyl, aryl, or heteroaryl;

$L^1$ is a bond, $C_{1-10}$ alkylene, or $C_{2-10}$ heteroalkylene;

$L^2$ is a bond, $C_{1-10}$ alkylene, or $C_{2-10}$ heteroalkylene;

$R^1$ is hydrogen, $C_{1-20}$ alkyl, $C_{2-20}$ alkenyl, $C_{2-20}$ alkynyl, $C_{2-20}$ heteroalkyl,

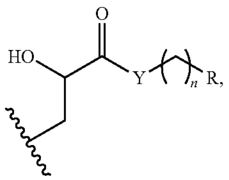

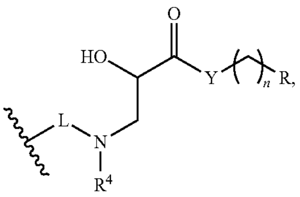

or

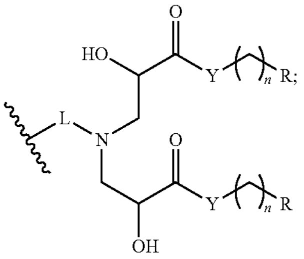

wherein the $C_{1-20}$ alkyl, $C_{2-20}$ alkenyl, $C_{2-20}$ alkynyl, or $C_{2-20}$ heteroalkyl is independently optionally substituted with one to five halo, cyano, —$OR^4$, —$SR^4$, —$NR^4_2$, —$N(R^4)_3^+$, oxo, $C_{1-6}$ alkyl, $C_{2-6}$ alkenyl, $C_{2-6}$ alkynyl, or $C_{1-6}$haloalkyl;

$R^2$ is

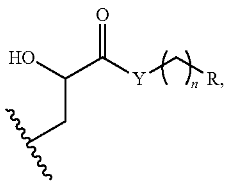

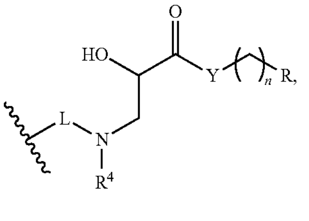

or

-continued

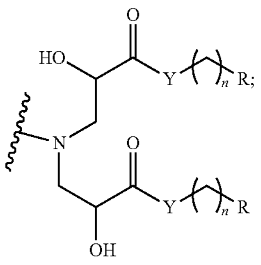

L is $C_{1-10}$ alkylene or $C_{3-10}$ heteroalkylene;

each $R^4$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —$SR^5$, —$NR^5_2$, —$N(R^5)_3^+$, or oxo;

each $R^5$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —SH, —$NH_2$, —$NH(C_{1-6}$ alkyl), —$N(C_{1-6}$ alkyl$)_2$, —$N(C_{1-6}$ alkyl$)_3^+$, or oxo;

each Y is independently —O— or —$NR^7$—;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —$NH(C_{1-6}$ alkyl), —$N(C_{1-6}$ alkyl$)_2$, —$N(C_{1-6}$ alkyl$)_3^+$, oxo, $C_{1-6}$ alkoxy, or $C_{1-6}$ haloalkoxy;

each n is independently an integer from 1-20;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—; and each $Z^1$ is independently —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—;

provided that each

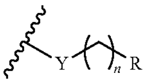

moiety comprises at least 6 linear atoms.

In one aspect, provided is a compound of Formula I:

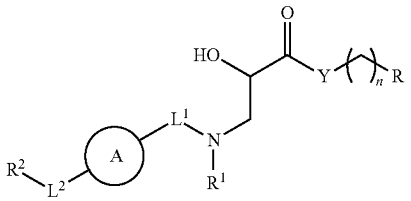

I or a pharmaceutically acceptable salt, stereoisomer, or mixture of stereoisomers thereof, wherein:

Ring A is $C_{3-10}$ cycloalkyl, heterocyclyl, aryl, or heteroaryl;

$L^1$ is a bond, $C_{1-10}$ alkylene, or $C_{2-10}$ heteroalkylene;

$L^2$ is a bond, $C_{1-10}$ alkylene, or $C_{2-10}$ heteroalkylene;

$R^1$ is hydrogen,

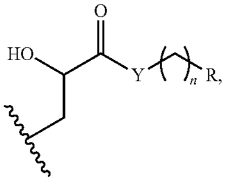

, or

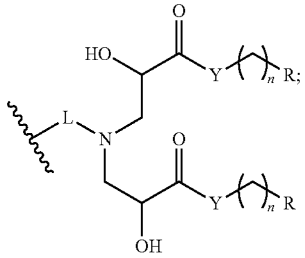

$R^2$ is

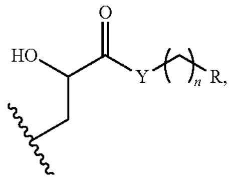

, or

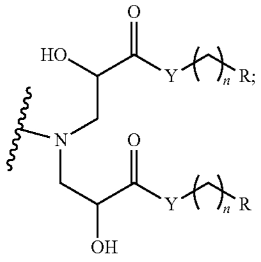

L is $C_{1-10}$ alkylene or $C_{3-10}$ heteroalkylene;

each $R^4$ is independently hydrogen, $C_{1-12}$ alkyl, $C_{2-12}$ alkenyl, or $C_{2-12}$ alkynyl;

each Y is independently —O— or —$NR^7$—;

each n is independently an integer from 1-20;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —$NH(C_{1-6}$ alkyl), —$N(C_{1-6}$ alkyl$)_2$, —$N(C_{1-6}$ alkyl$)_3^+$, oxo, $C_{1-6}$ alkoxy, or $C_{1-6}$ haloalkoxy;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—; and each $Z^1$ is independently —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—;

provided that each

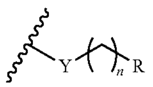

moiety comprises at least 6 linear atoms.

In some embodiments, provided is a compound of Formula IA:

IA

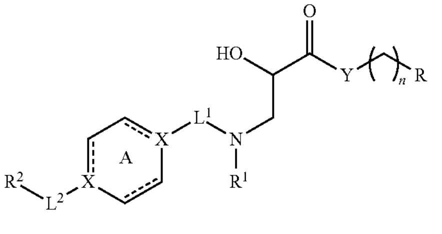

or a pharmaceutically acceptable salt, stereoisomer, or mixture of stereoisomers thereof, wherein:

Ring A is an aromatic or non-aromatic ring;

each X is independently CH or N, and each ⋰ bond represents a single bond; or each X is C, and each ⋰ bond represents a double bond;

$R^1$ is hydrogen, $C_{1-20}$ alkyl, $C_{2-20}$ alkenyl, $C_{2-20}$ alkynyl, $C_{2-20}$ heteroalkyl,

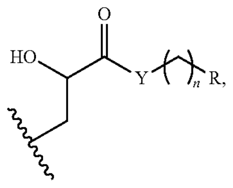

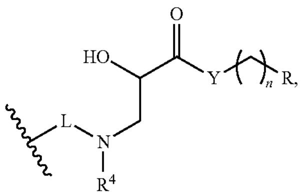

or

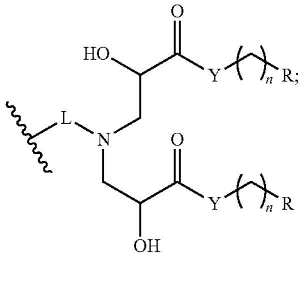

wherein the $C_{1-20}$ alkyl, $C_{2-20}$ alkenyl, $C_{2-20}$ alkynyl, or $C_{2-20}$ heteroalkyl is independently optionally substituted with one to five halo, cyano, —$OR^4$, —$SR^4$, —$NR^4_2$, —$N(R^4)_3^+$, oxo, $C_{1-6}$ alkyl, $C_{2-6}$ alkenyl, $C_{2-6}$ alkynyl, or $C_{1-6}$haloalkyl;

$R^2$ is

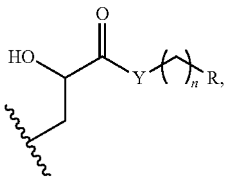

or

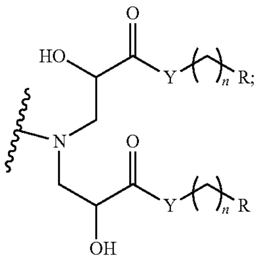

L is $C_{1-10}$ alkylene or $C_{3-10}$ heteroalkylene;

$L^1$ is a bond, $C_{1-10}$ alkylene, or $C_{2-10}$ heteroalkylene; provided that when $L^1$ is a bond, then the X bonded thereto is a carbon atom;

$L^2$ is a bond, $C_{1-10}$ alkylene, or $C_{2-10}$ heteroalkylene; provided that when $L^2$ is a bond, then the X—$R^2$ bond is not a N—N bond;

each $R^4$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —$SR^5$, —$NR^5_2$, —$N(R^5)_3^+$, or oxo; each $R^5$ is independently hydrogen, $C_{1-12}$ alkyl, $C_{2-12}$ alkenyl, or $C_{2-12}$ alkynyl;

wherein each $C_{1-12}$ alkyl, $C_{2-12}$ alkenyl, or $C_{2-12}$ alkynyl is independently optionally substituted with one to five halo, cyano, —OH, —SH, —$NH_2$, —NH($C_{1-6}$ alkyl), —N($C_{1-6}$ alkyl$)_2$, —N($C_{1-6}$ alkyl$)_3^+$, or oxo;

each Y is independently —O— or —$NR^7$—;

each n is independently an integer from 1-20;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —NH($C_{1-6}$ alkyl), —N($C_{1-6}$ alkyl$)_2$, —N($C_{1-6}$ alkyl$)_3^+$, oxo, $C_{1-6}$ alkoxy, or $C_{1-6}$ haloalkoxy;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—; and each $Z^1$ is independently —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—;

provided that each

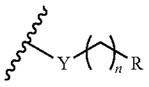

moiety comprises at least 6 linear atoms.

In some embodiments, provided is a compound of Formula IA:

IA

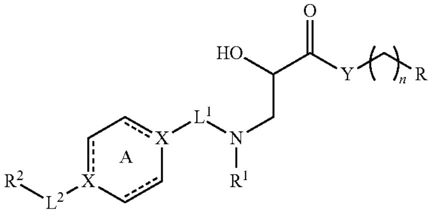

or a pharmaceutically acceptable salt, stereoisomer, or mixture of stereoisomers thereof, wherein:

Ring A is an aromatic or non-aromatic ring;

each X is independently CH or N, and each

bond represents a single bond; or each X is C, and each

bond represents a double bond;

$R^1$ is hydrogen,

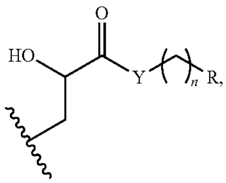

or

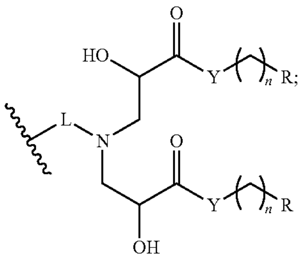

$R^2$ is

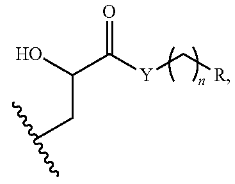

or

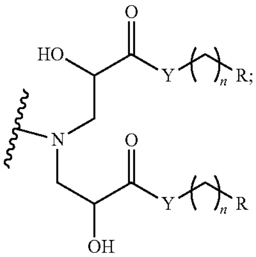

L is $C_{1-10}$ alkylene or $C_{3-10}$ heteroalkylene;

$L^1$ is a bond, $C_{1-10}$ alkylene, or $C_{2-10}$ heteroalkylene; provided that when $L^1$ is a bond, then the X bonded thereto is a carbon atom;

$L^2$ is a bond, $C_{1-10}$ alkylene, or $C_{2-10}$ heteroalkylene; provided that when $L^2$ is a bond, then the X—$R^2$ bond is not a N—N bond;

each $R^4$ is independently hydrogen, $C_{1-12}$ alkyl, $C_{2-12}$ alkenyl, or $C_{2-12}$ alkynyl;

each Y is independently —O— or —$NR^7$—;

each n is independently an integer from 1-20;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —NH($C_{1-6}$ alkyl), —N($C_{1-6}$ alkyl)$_2$, —N($C_{1-6}$ alkyl)$_3$f, oxo, $C_{1-6}$ alkoxy, or $C_{1-6}$ haloalkoxy;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2$$NR^4$—; and each $Z^1$ is independently —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2$$NR^4$—;

provided that each

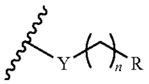

moiety comprises at least 6 linear atoms.

In some embodiments, X is CH. In some embodiments, X is N.

In some embodiments, Ring A is an aromatic ring. In some embodiments, Ring A is a non-aromatic ring.

In some embodiments, Ring A is $C_{3-10}$ cycloalkyl. In some embodiments, Ring A is cyclopropyl, cyclobutyl, cyclopentyl, cyclohexyl, cycloheptyl, or cyclooctyl.

In some embodiments, Ring A is a 5-6 membered heterocyclyl containing one or two heteroatoms selected from O, N, and S. In some embodiments, Ring A is pyrrolidinyl, imidazonlinyl, imidazolidinyl, piperidinyl, piperazinyl, or morpholinyl.

In some embodiments, Ring A is $C_{6-10}$ aryl. In some embodiments, Ring A is phenyl or naphthyl.

In some embodiments, Ring A is a 5-6 membered heteroaryl containing one to three heteroatoms selected from O, N, and S. In some embodiments, Ring A is pyrrolyl, imidazolyl, pyrazolyl, pyridinyl, pyrimidinyl, pyridazinyl, oxazolyl, or thiazolyl.

In some embodiments, Ring A is cyclopropyl, cyclobutyl, cyclopentyl, cyclohexyl, cycloheptyl, cyclooctyl, pyrrolidinyl, imidazonlinyl, piperidinyl, piperazinyl, morpholinyl, phenyl, naphthyl, pyrrolyl, imidazolyl, pyrazolyl, pyridinyl, pyrimidinyl, pyridazinyl, oxazolyl, or thiazolyl. In some embodiments, Ring A is cyclohexyl, piperidinyl, piperazinyl, pyridinyl, pyrimidinyl, or pyridazinyl.

In some embodiments, Ring A is

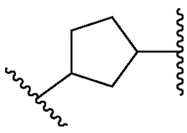

,

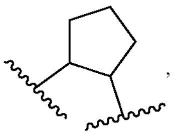

,

-continued
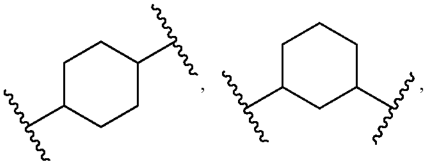
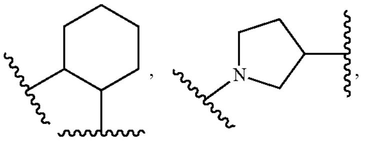
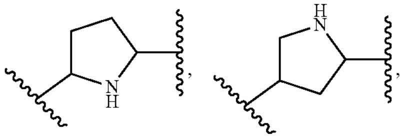
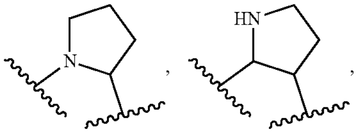
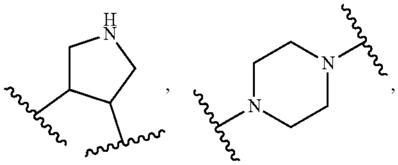
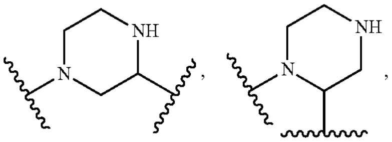
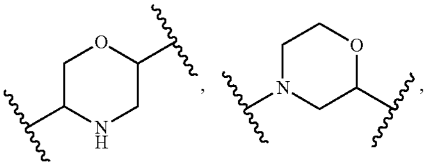
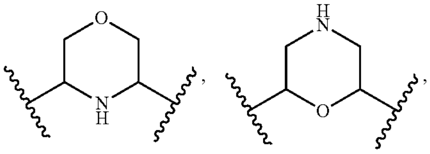
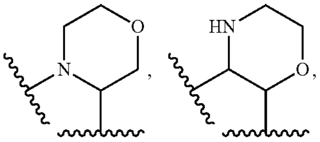
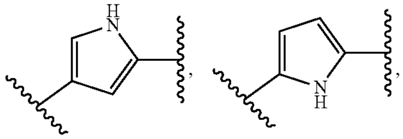
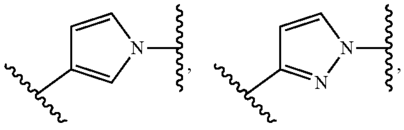
-continued
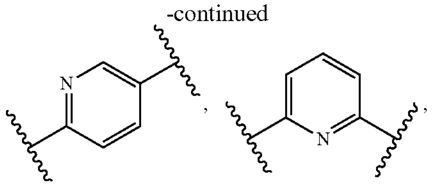
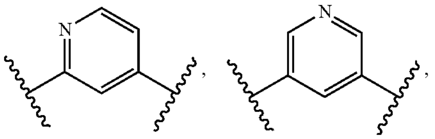
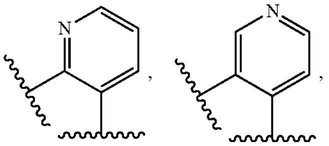
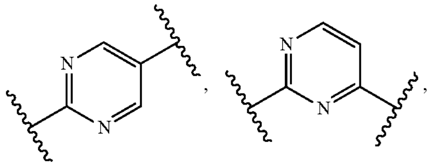
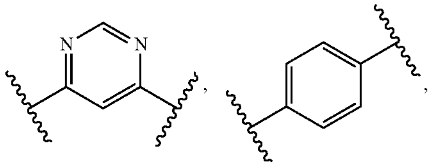
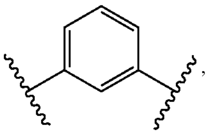
or
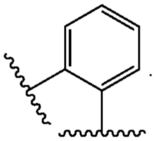
In some embodiments, Ring A is
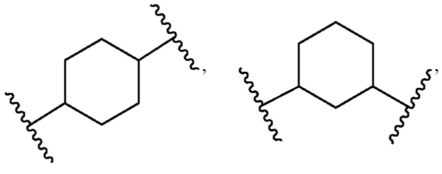
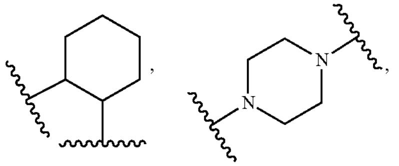
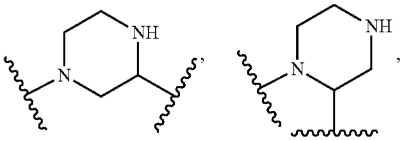
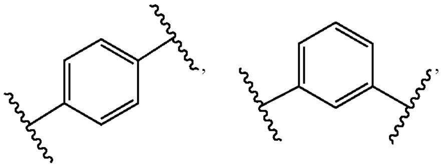
or -continued

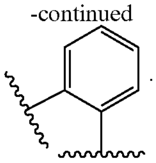.

In some embodiments, Ring A is

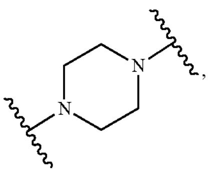, 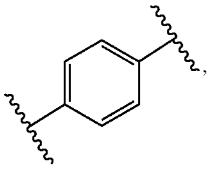, or

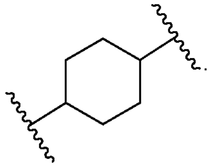.

In some embodiments, Ring A is

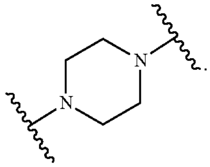 [SMILES: *N1CCN(*)CC1].

In some embodiments, Ring A is:

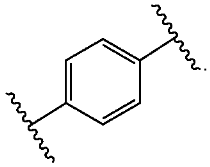 [SMILES: *c1ccc(*)cc1].

In some embodiments, Ring A is

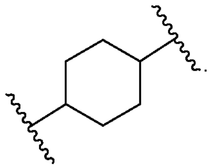 [SMILES: *C1CCC(*)CC1].

In some embodiments, each n is independently an integer from 2-12. In some embodiments, each n is independently 4-12. In some embodiments, each n is independently 4, 6, 8, 10, or 12. In some embodiments, n is 4. In some embodiments, n is 6. In some embodiments, n is 8. In some embodiments, n is 10. In some embodiments, n is 12.

In some embodiments, Y is O. In some embodiments, Y is NH.

In some embodiments, $L^1$ is a bond, $C_{1-10}$ alkylene, or $C_{2-10}$ heteroalkylene.

In some embodiments, $L^1$ is a bond.

In some embodiments, $L^1$ is $C_{1-10}$ alkylene. In some embodiments, $L^1$ is $C_{2-6}$ alkylene. In some embodiments, $L^1$ is ethylene, propylene, or butylene. In some embodiments, $L^1$ is ethylene. In some embodiments, $L^1$ is propylene.

In some embodiments, $L^1$ is $C_{2-10}$ heteroalkylene. In some embodiments, $L^1$ is $C_{2-6}$ heteroalkylene. In some embodiments, $L^1$ is $C_{2-6}$ heteroalkylene containing one or two 0, N, or S.

In some embodiments, $L^2$ is a bond, $C_{1-10}$ alkylene, or $C_{2-10}$ heteroalkylene.

In some embodiments, $L^2$ is a bond.

In some embodiments, $L^2$ is $C_{1-10}$ alkylene. In some embodiments, $L^2$ is $C_{2-6}$ alkylene. In some embodiments, $L^2$ is ethylene, propylene, or butylene. In some embodiments, $L^2$ is ethylene. In some embodiments, $L^2$ is propylene.

In some embodiments, $L^2$ is $C_{2-10}$ heteroalkylene. In some embodiments, $L^2$ is $C_{2-6}$ heteroalkylene. In some embodiments, $L^2$ is $C_{2-6}$ heteroalkylene containing one or two 0, N, or S.

In some embodiments, $L^1$ is a bond and $L^2$ is a bond. In some embodiments, $L^1$ is $C_{1-10}$ alkylene and $L^2$ is $C_{1-10}$ alkylene. In some embodiments, $L^1$ is $C_{2-6}$ alkylene and $L^2$ is $C_2$-6 alkylene. In some embodiments, $L^1$ is ethylene and $L^2$ is ethylene. In some embodiments, $L^1$ is propylene and $L^2$ is propylene. In some embodiments, $L^1$ is ethylene and $L^2$ is propylene. In some embodiments, $L^1$ is propylene and $L^2$ is ethylene.

In some embodiments, $R^1$ is hydrogen, $C_{1-20}$ alkyl, $C_{2-20}$ alkenyl, $C_{2-20}$ alkynyl, or $C_{2-20}$ heteroalkyl, wherein the $C_{1-20}$ alkyl, $C_{2-20}$ alkenyl, $C_{2-20}$ alkynyl, or $C_{2-20}$ heteroalkyl is independently optionally substituted with one to five halo, cyano, $—OR^4$, $—SR^4$, $—NR^4_2$, $—N(R^4)_3^+$, oxo, $C_{1-6}$ alkyl, $C_{2-6}$ alkenyl, $C_{2-6}$ alkynyl, or $C_{1-6}$ haloalkyl;

In some embodiments, $R^1$ is hydrogen.

In some embodiments, $R^1$ is $C_{1-20}$ alkyl. In some embodiments, $R^1$ is $C_{2-20}$ alkenyl. In some embodiments, $R^1$ is $C_{2-20}$ alkynyl. In some embodiments, $R^1$ is $C_{2-20}$ heteroalkyl.

In some embodiments, $R^1$ is

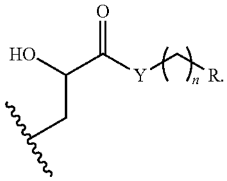.

In some embodiments, $R^1$ is

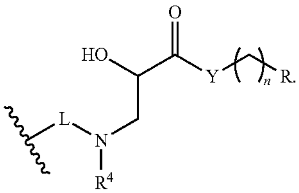.

In some embodiments, $R^1$ is

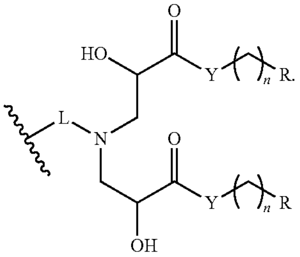

In some embodiments, L is $C_{1-10}$ alkylene. In some embodiments, L is $C_{3-10}$ heteroalkylene. In some embodiments, L is In some embodiments, L is $C_{2-6}$ alkylene. In some embodiments, L is ethylene, propylene, or butylene. In some embodiments, L is ethylene. In some embodiments, L is propylene.

In some embodiments, $R^2$ is

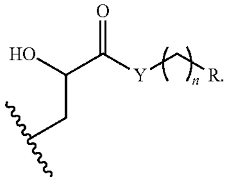

In some embodiments, $R^2$ is

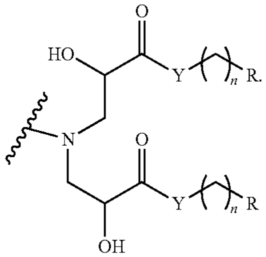

In some embodiments, provided is a compound of Formula II:

II

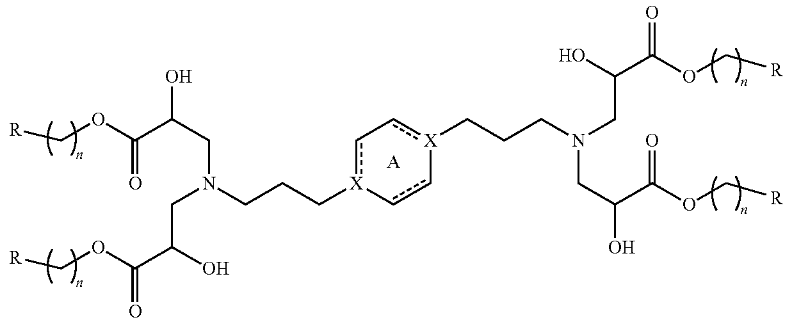

or a pharmaceutically acceptable salt, stereoisomer, or mixture of stereoisomers thereof wherein each X, n, and R are independently as defined herein.

In some embodiments, provided is a compound of Formula IIA:

IIA

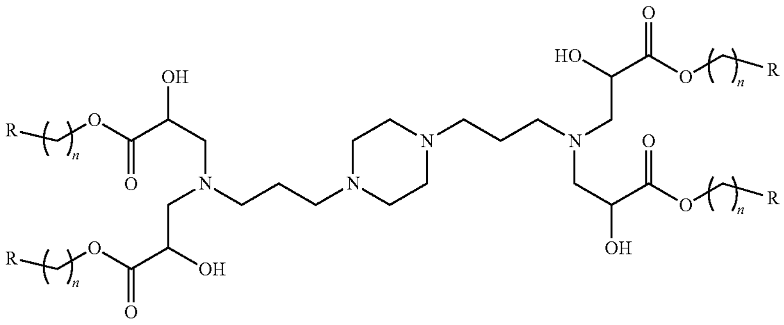

or a pharmaceutically acceptable salt, stereoisomer, or mixture of stereoisomers thereof wherein each n and R are independently as defined herein.

In some embodiments, provided is a compound of Formula IIB:

IIB

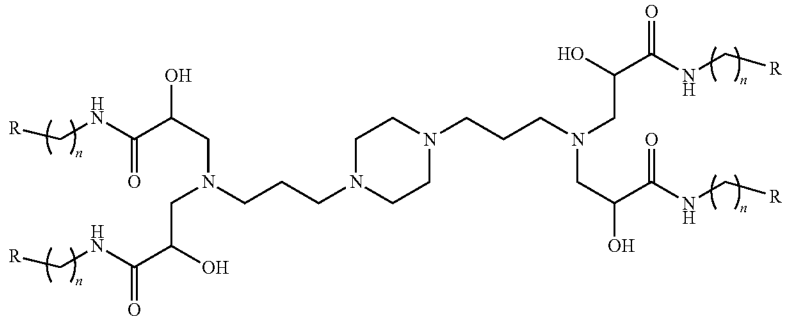

or a pharmaceutically acceptable salt, stereoisomer, or mixture of stereoisomers thereof wherein each n and R are independently as defined herein.

In some embodiments, provided is a compound of Formula IIC:

IIC

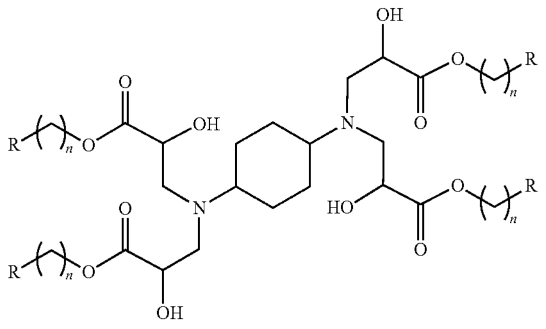

or a pharmaceutically acceptable salt, stereoisomer, or mixture of stereoisomers thereof wherein each n and R are independently as defined herein.

In some embodiments, provided is a compound of Formula IID:

IID

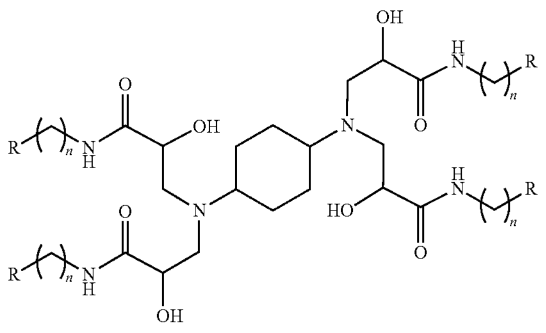

or a pharmaceutically acceptable salt, stereoisomer, or mixture of stereoisomers thereof wherein each n and R are independently as defined herein.

In some embodiments, provided is a compound of Formula IIE:

IIE

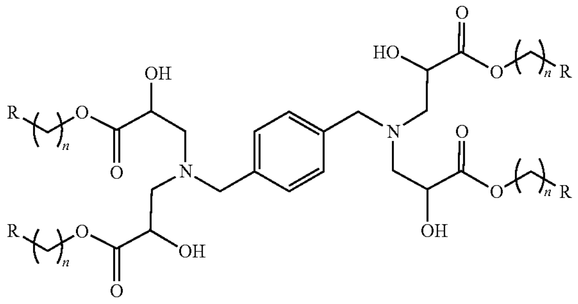

or a pharmaceutically acceptable salt, stereoisomer, or mixture of stereoisomers thereof wherein each n and R are independently as defined herein.

In some embodiments, provided is a compound of Formula IIF:

IIF

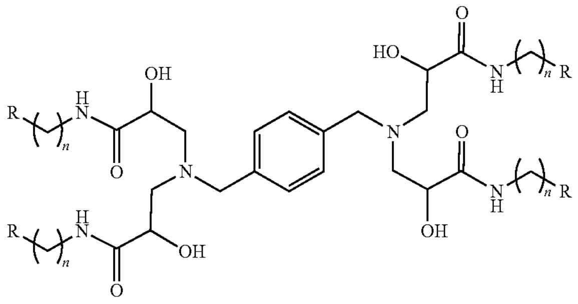

or a pharmaceutically acceptable salt, stereoisomer, or mixture of stereoisomers thereof wherein each n and R are independently as defined herein.

In some embodiments, provided is a compound of Formula III:

III

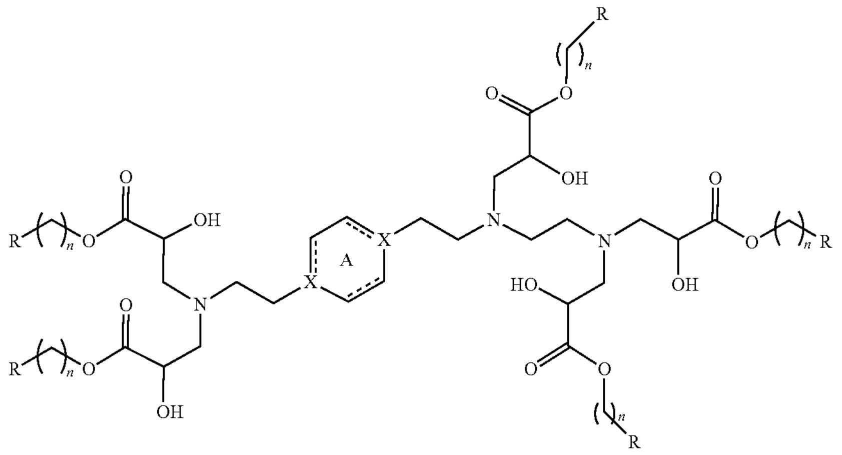

or a pharmaceutically acceptable salt, stereoisomer, or mixture of stereoisomers thereof wherein each n and R are independently as defined herein.

In some embodiments, provided is a compound of Formula IIIA:

IIIA

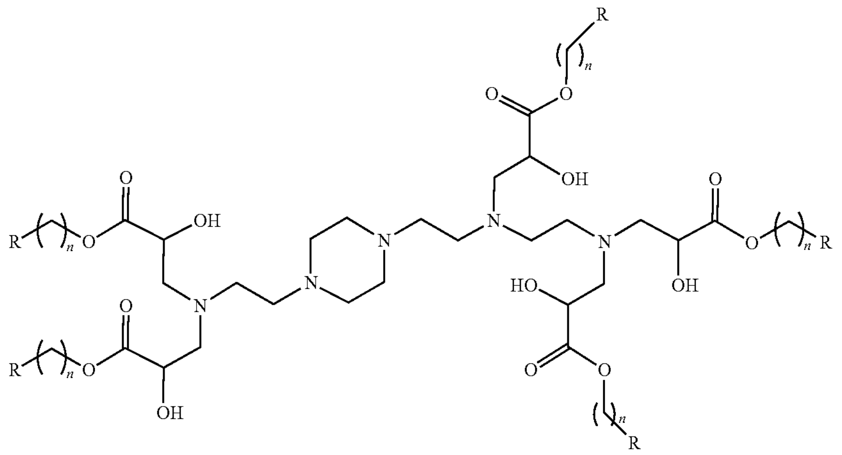

or a pharmaceutically acceptable salt, stereoisomer, or mixture of stereoisomers thereof wherein each n and R are independently as defined herein.

In some embodiments, provided is a compound of Formula IIIB:

IIIB

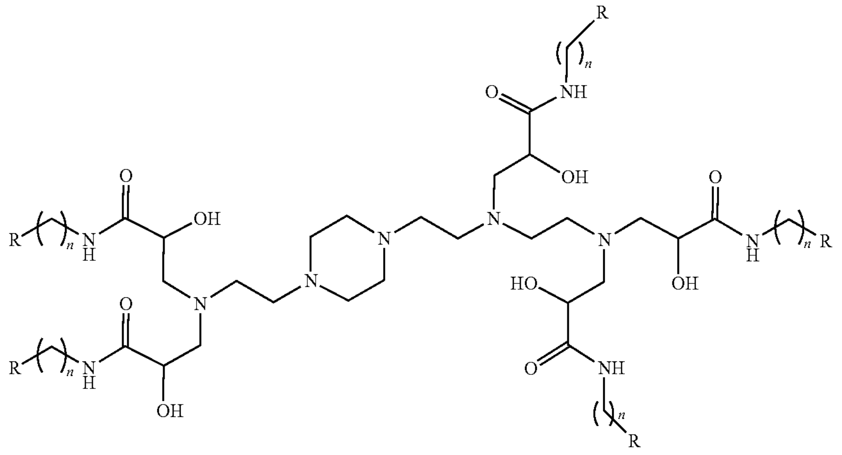

or a pharmaceutically acceptable salt, stereoisomer, or mixture of stereoisomers thereof wherein each n and R are independently as defined herein.

In some embodiments, provided is a compound of Formula IV:

IV

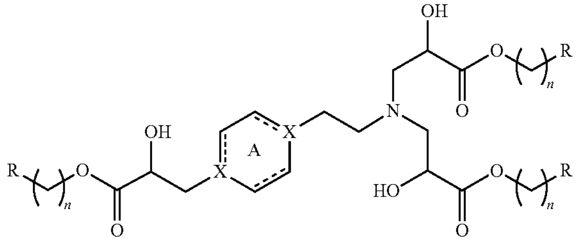

or a pharmaceutically acceptable salt, stereoisomer, or mixture of stereoisomers thereof wherein each X, n, and R are independently as defined herein.

In some embodiments, provided is a compound of Formula IVA:

IVA

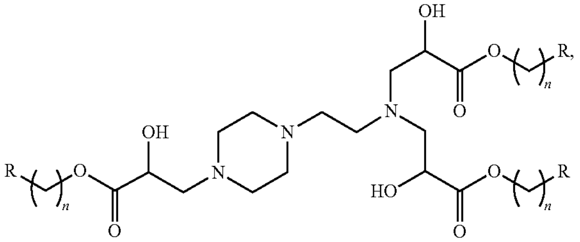

or a pharmaceutically acceptable salt, stereoisomer, or mixture of stereoisomers thereof wherein each n and R are independently as defined herein.

In some embodiments provided is a compound of Formula IVB:

IVB

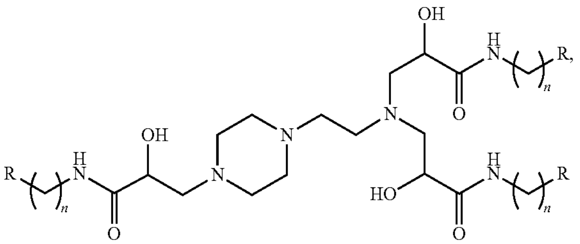

or a pharmaceutically acceptable salt, stereoisomer, or mixture of stereoisomers thereof wherein each n and R are independently as defined herein.

In some embodiments, provided is a compound of Formula IVC:

IVC

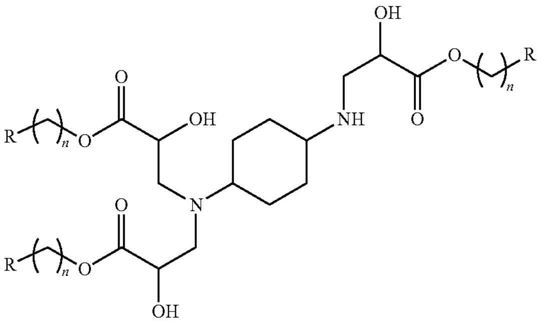

or a pharmaceutically acceptable salt, stereoisomer, or mixture of stereoisomers thereof wherein each n and R are independently as defined herein.

In some embodiments, provided is a compound of Formula IVD:

IVD

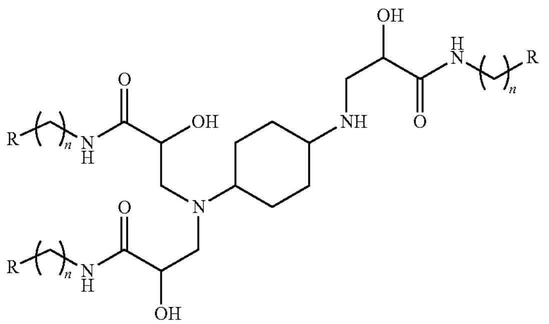

or a pharmaceutically acceptable salt, stereoisomer, or mixture of stereoisomers thereof wherein each n and R are independently as defined herein.

In some embodiments, provided is a compound of Formula IVE:

IVE

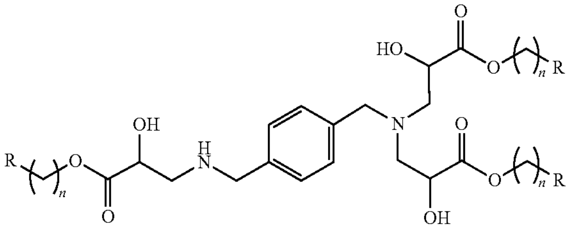

or a pharmaceutically acceptable salt, stereoisomer, or mixture of stereoisomers thereof wherein each n and R are independently as defined herein.

In some embodiments, provided is a compound of Formula IVF:

IVF

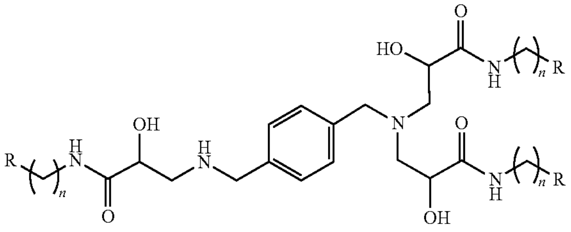

or a pharmaceutically acceptable salt, stereoisomer, or mixture of stereoisomers thereof wherein each n and R are independently as defined herein.

In some embodiments, each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl.

In some embodiments, each R is independently hydrogen, —Z—$C_{1-20}$ alkyl, —Z—$C_{2-20}$ alkenyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{2-6}$ alkenyl-Z—$C_{1-20}$ alkyl, or —$Z^1$—$C_{2-6}$ alkenyl-Z—$C_{2-20}$ alkenyl.

In some embodiments, each Z is independently a bond, —O—, —$NR^4$—, —S—, —S—S—, —C(O)—, —OC(O)—, —C(O)O—, —C(O)$NR^4$—, —S(O)—, —$S(O)_2$—, —$NR^4$C(O)—, —$NR^4$C(O)O—, —$NR^4$C(O)$NR^4$—, —$NR^4$S(O)—, or —$S(O)_2NR^4$—. In some embodiments, $R^4$ is independently hydrogen, $C_{1-12}$ alkyl, $C_{2-12}$ alkenyl, or $C_{2-12}$ alkynyl.

In some embodiments, each Z is independently —O—, —$NR^4$, —S—, —S—S—, —C(O)—, —OC(O)—, —C(O)O—, —C(O)$NR^4$, or —$NR^4$C(O)—, wherein each $R^4$ is independently hydrogen or $C_{1-12}$ alkyl. In some embodiments, each Z is independently —O—, NH—, —S—, —S—S—, —C(O)—, —OC(O)—, —C(O)O—, —C(O)NH—, or —NHC(O)—.

In some embodiments, each Z is independently —O—, —S—S—, or —OC(O)—. In some embodiments, Z is —O—. In some embodiments, Z is —S—S—. In some embodiments, Z is —OC(O)—.

In some embodiments, each R is independently —Z—$C_{1-20}$ alkyl wherein Z is —OC(O)—. In some embodiments, each R is independently —OC(O)—$C_{10-20}$ alkyl. In some embodiments, each R is independently —OC(O)—$C_{12-16}$ alkyl. In some embodiments, each R is independently —OC(O)—$C_{12-16}$ alkyl wherein the $C_{12-16}$ alkyl is branched.

In some embodiments, n is 2 and R is —OC(O)—$C_{10-20}$ alkyl. In some embodiments, n is 2 and R is —OC(O)—$C_{12-16}$ alkyl. In some embodiments, n is 2 and R is —OC(O)—$C_{12-16}$ alkyl wherein the $C_{12-16}$ alkyl is branched. In some embodiments, n is 4 and R is —OC(O)—$C_{10-20}$ alkyl. In some embodiments, n is 4 and R is —OC(O)—$C_{12-16}$ alkyl. In some embodiments, n is 4 and R is —OC(O)—$C_{12-16}$ alkyl wherein the $C_{12-16}$ alkyl is branched. In some embodiments, n is 6 and R is —OC(O)—$C_{10-20}$ alkyl. In some embodiments, n is 6 and R is —OC(O)—$C_{12-16}$ alkyl. In some embodiments, n is 6 and R is —OC(O)—$C_{12-16}$ alkyl wherein the $C_{12-16}$ alkyl is branched. In some embodiments, n is 8 and R is —OC(O)—$C_{10-20}$ alkyl. In some embodiments, n is 8 and R is —OC(O)—$C_{12-16}$ alkyl. In some embodiments, n is 8 and R is —OC(O)—$C_{12-16}$ alkyl wherein the $C_{12-16}$ alkyl is branched.

In some embodiments, R is —Z—$C_{1-20}$ alkyl wherein Z is —O—. In some embodiments, R is —O—$C_{1-12}$ alkyl. In some embodiments, R is —O—$C_{6-12}$ alkyl.

In some embodiments, n is 2 and R is —O—$C_{1-12}$ alkyl. In some embodiments, n is 2 and R is —O—$C_{6-12}$ alkyl. In some embodiments, n is 4 and R is —O—$C_{1-12}$ alkyl. In some embodiments, n is 4 and R is —O—$C_{6-12}$ alkyl. In some embodiments, n is 6 and R is —O—$C_{1-12}$ alkyl. In some embodiments, n is 6 and R is —O—$C_{6-12}$ alkyl. In some embodiments, n is 8 and R is —O—$C_{1-12}$ alkyl. In some embodiments, n is 8 and R is —O—$C_{6-12}$ alkyl.

In some embodiments, R is —Z—$C_{1-20}$ alkyl wherein Z is —S—S—. In some embodiments, R is —S—S—$C_{1-12}$ alkyl. In some embodiments, R is —S—S—$C_{6-12}$ alkyl.

In some embodiments, n is 2 and R is —S—S—$C_{1-12}$ alkyl. In some embodiments, n is 2 and R is —S—S—$C_{6-12}$ alkyl. In some embodiments, n is 4 and R is —S—S—$C_{1-12}$ alkyl. In some embodiments, n is 4 and R is —S—S—$C_{6-12}$ alkyl. In some embodiments, n is 6 and R is —S—S—$C_{1-12}$ alkyl. In some embodiments, n is 6 and R is —S—S—$C_{6-12}$ alkyl. In some embodiments, n is 8 and R is —S—S—$C_{1-12}$ alkyl. In some embodiments, n is 8 and R is —S—S—$C_{6-12}$ alkyl.

In some embodiments, R is —Z—$C_{2-20}$ alkenyl wherein each Z is independently —O—, —S—S—, or —OC(O)—. In some embodiments, R is —O—$C_{6-12}$ alkenyl. In some embodiments, R is —S—S—$C_{6-12}$ alkenyl. In some embodiments, R is —OC(O)—$C_{6-12}$ alkenyl. In some embodiments, n is 4 and R is —O—$C_{6-12}$ alkenyl. In some embodiments, n is 4 and R is —S—S—$C_{6-12}$ alkenyl. In some embodiments, n is 4 and R is —OC(O)—$C_{6-12}$ alkenyl. In some embodiments, n is 6 and R is —O—$C_{6-12}$ alkenyl. In some embodiments, n is 6 and R is —S—S—$C_{6-12}$ alkenyl. In some embodiments, n is 6 and R is —OC(O)—$C_{6-12}$ alkenyl.

In some embodiments, R is —Z—$C_{2-20}$ alkynyl wherein each Z is independently —O—, —S—S—, or —OC(O)—. In some embodiments, R is —O—$C_{6-12}$ alkynyl. In some embodiments, R is —S—S—$C_{6-12}$ alkynyl. In some embodiments, R is —OC(O)—$C_{6-12}$ alkynyl. In some embodiments, n is 4 and R is —O—$C_{6-12}$ alkynyl. In some embodiments, n is 4 and R is —S—S—$C_{6-12}$ alkynyl. In some embodiments, n is 4 and R is —OC(O)—$C_{6-12}$ alkynyl. In some embodiments, n is 6 and R is —O—$C_{6-12}$ alkynyl. In some embodiments, n is 6 and R is —S—S—$C_{6-12}$ alkynyl. In some embodiments, n is 6 and R is —OC(O)—$C_{6-12}$ alkynyl.

In some embodiments, each R independently is —$Z^1$—$C_{1-6}$ alkylene-Z—$C_{1-20}$ alkyl or —$Z^1$—$C_{1-6}$ alkylene-Z—$C_{2-20}$ alkenyl, wherein each $Z^1$ is independently —O—, —S—S—, or —OC(O)— and each Z is independently —O—, —S—S—, or —OC(O)—. In some embodiments, $Z^1$ is —O— and Z is —O—. In some embodiments, $Z^1$ is —O— and Z is —S—S—. In some embodiments, $Z^1$ is —O— and Z is —OC(O)—. In some embodiments, $Z^1$ is —OC(O)— and Z is —O—.

In some embodiments, R is —O—$C_{1-6}$ alkylene-O—$C_{1-20}$ alkyl. In some embodiments, R is —O—$C_{1-4}$ alkylene-O—$C_{1-12}$ alkyl. In some embodiments, R is —O—$CH_2$—O—$C_{6-12}$ alkyl. In some embodiments, R is —O—CH($CH_3$)—O—$C_{6-12}$ alkyl. In some embodiments, n is 2 and R is —O—$C_{1-4}$ alkylene-O—$C_{1-12}$ alkyl. In some embodiments, n is 2 and R is —O—$CH_2$—O—$C_{6-12}$ alkyl. In some embodiments, n is 2 and R is —O—CH($CH_3$)—O—$C_{6-12}$ alkyl. In some embodiments, n is 4 and R is —O—$C_{1-4}$ alkylene-O—$C_{1-12}$alkyl. In some embodiments, n is 4 and R is —O—$CH_2$—O—$C_{6-12}$alkyl. In some embodiments, n is 4 and R is —O—CH($CH_3$)—O—$C_{6-12}$ alkyl. In some embodiments, n is 6 and R is —O—$C_{1-4}$ alkylene-O—$C_{1-12}$ alkyl. In some embodiments, n is 6 and R is —O—$CH_2$—O—$C_{6-12}$ alkyl. In some embodiments, n is 6 and R is —O—CH($CH_3$)—O—$C_{6-12}$ alkyl.

In some embodiments, R is —O—$C_{1-6}$ alkylene-O—$C_{1-20}$ alkenyl. In some embodiments, R is —O—$C_{1-4}$ alkylene-O—$C_{1-12}$ alkenyl. In some embodiments, R is —O—$CH_2$—O—$C_{6-12}$alkenyl. In some embodiments, R is —O—CH($CH_3$)—O—$C_{6-12}$ alkenyl. In some embodiments, n is 2 and R is —O—$C_{1-4}$ alkylene-O—$C_{1-12}$ alkenyl. In some embodiments, n is 2 and R is —O—$CH_2$—O—$C_{6-12}$ alkenyl. In some embodiments, n is 2 and R is —O—CH($CH_3$)—O—$C_{6-12}$alkenyl. In some embodiments, n is 4 and R is —O—$C_{1-4}$ alkylene-O—$C_{1-12}$ alkenyl. In some embodiments, n is 4 and R is —O—$CH_2$—O—$C_{6-12}$ alkenyl. In some embodiments, n is 4 and R is —O—CH($CH_3$)—O—$C_{6-12}$ alkenyl. In some embodiments, n is 6 and R is —O—$C_{1-4}$ alkylene-O—$C_{1-12}$ alkenyl. In some embodiments, n is 6 and R is —O—$CH_2$—O—$C_{6-12}$ alkenyl. In some embodiments, n is 6 and R is —O—CH($CH_3$)—O—$C_{6-12}$ alkenyl.

In some embodiments, when R is hydrogen, n is 6-20. In some embodiments, when R is hydrogen, n is 6-14. In some embodiments, when R is hydrogen, n is 10-14. In some embodiments, n is 6 and R is hydrogen. In some embodiments, n is 8 and R is hydrogen. In some embodiments, n is 10 and R is hydrogen. In some embodiments, n is 12 and R is hydrogen. In some embodiments, n is 14 and R is hydrogen.

In some embodiments, the moiety

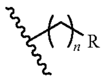

is selected from:

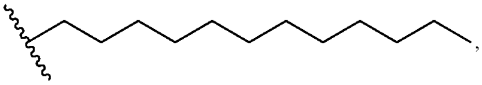
,

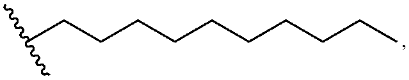
,

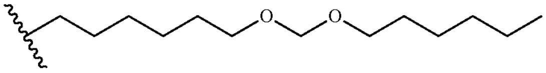
,

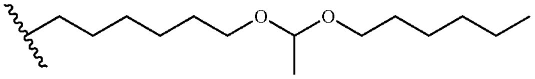
,

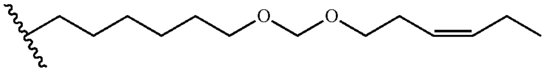
,

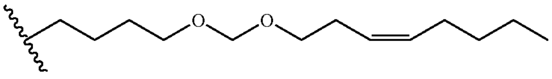
,

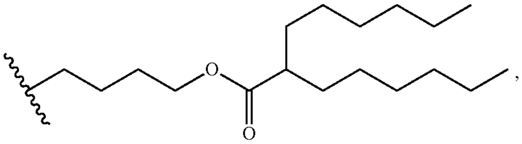
,

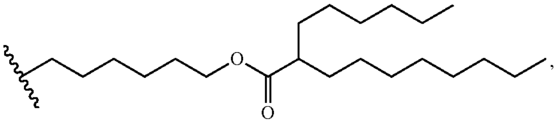
,

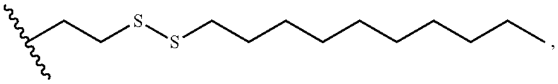
,

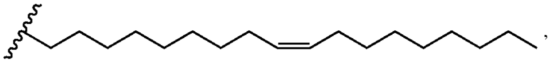
,

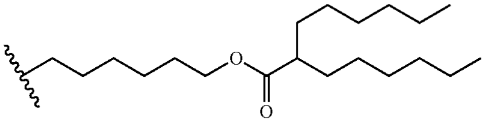
, and

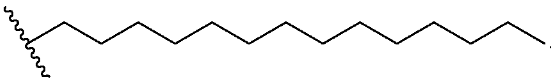
.

In some embodiments, the moiety
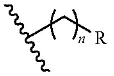
is selected from:
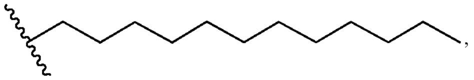,
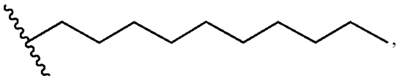,
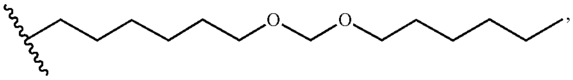,
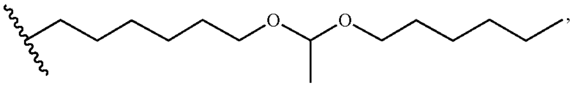,
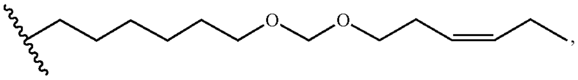,
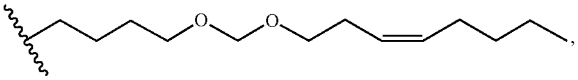,
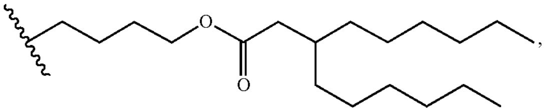,
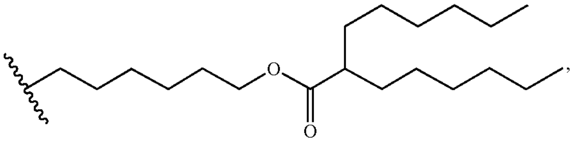,
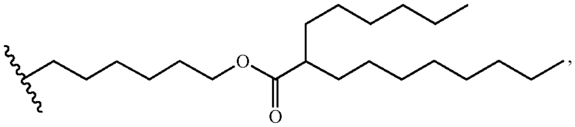,
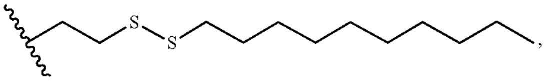,
and
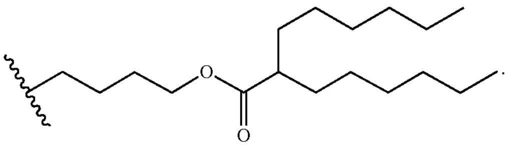.
In some embodiments, the moiety
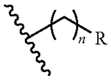
is selected from:
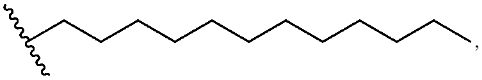,
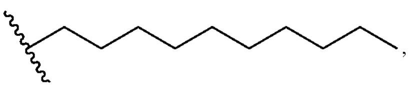,
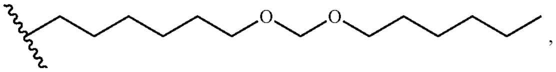,
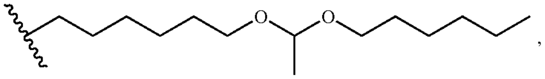,
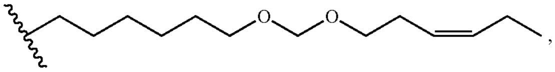,
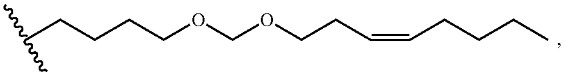,
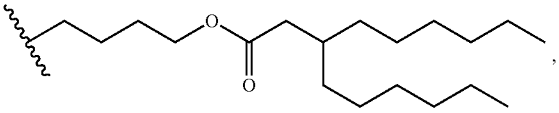,
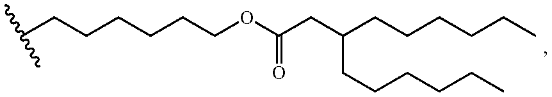,
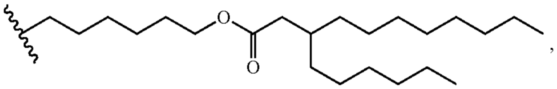,
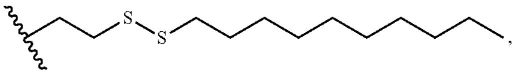, and
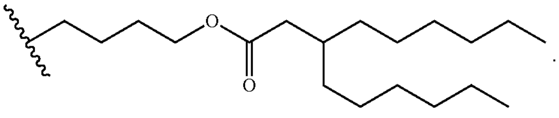.
In some embodiments, provided is a compound selected from Table 1A, or a pharmaceutically acceptable salt, stereoisomer, or mixture of stereoisomers thereof.

TABLE 1A
| Compounds | |
|---|---|
| Comp No. | Structure |
| L0180 | 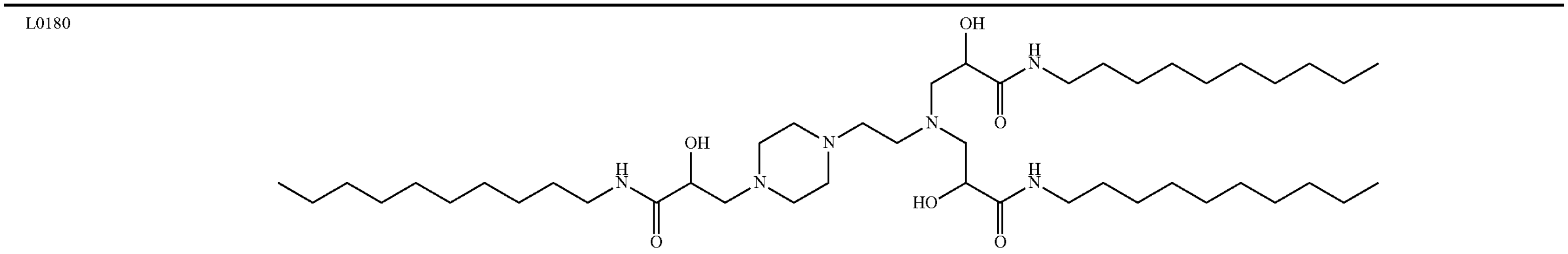 |
| L0181 | 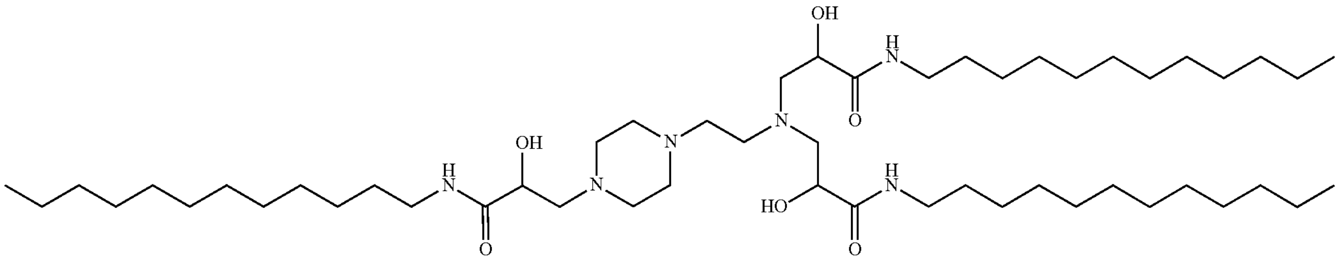 [SMILES: CCCCCCCCCCCCNC(=O)C(O)CN1CCN(CCN(CC(O)C(=O)NCCCCCCCCCCCC)CC(O)C(=O)NCCCCCCCCCCCC)CC1] |
| L0182 | 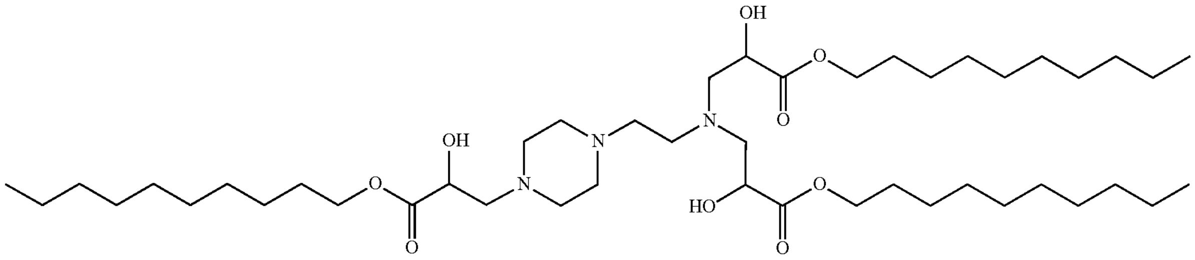 [SMILES: CCCCCCCCCCOC(=O)C(O)CN1CCN(CCN(CC(O)C(=O)OCCCCCCCCCC)CC(O)C(=O)OCCCCCCCCCC)CC1] |

TABLE 1A-continued
| Compounds | |
|---|---|
| Comp No. | Structure |
| L0183 | 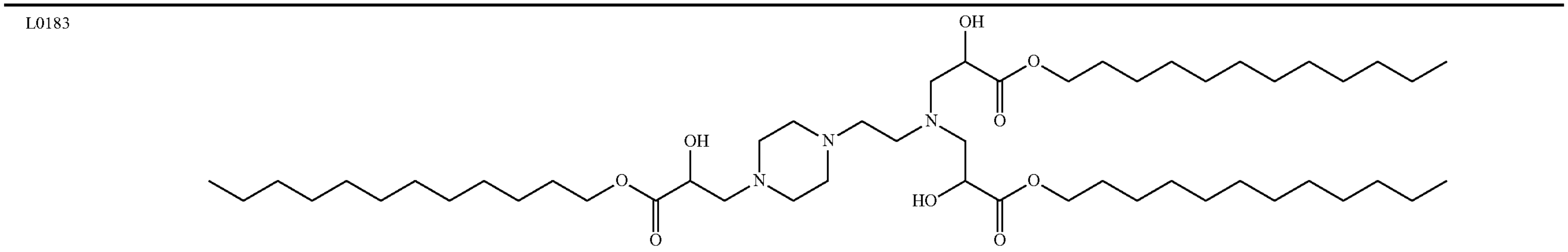 |
| L0184 | 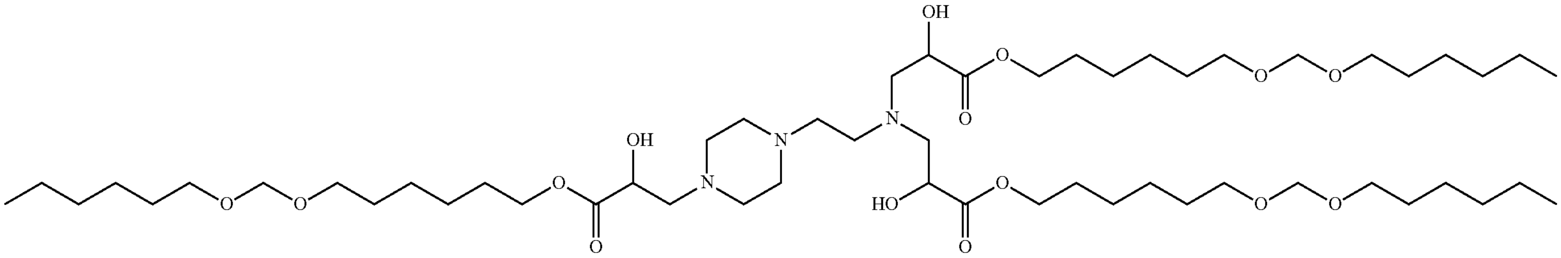 [SMILES: CCCCCCOCOCCCCCCOC(=O)C(O)CN1CCN(CCN(CC(O)C(=O)OCCCCCCOCOCCCCCC)CC(O)C(=O)OCCCCCCOCOCCCCCC)CC1] |
| L0185 | 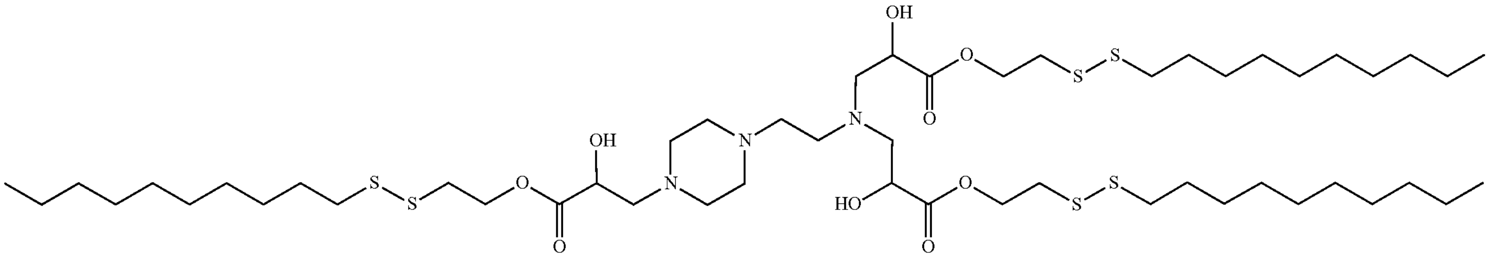 [SMILES: CCCCCCCCCCSSCCOC(=O)C(O)CN1CCN(CCN(CC(O)C(=O)OCCSSCCCCCCCCCC)CC(O)C(=O)OCCSSCCCCCCCCCC)CC1] |

TABLE 1A-continued
Compounds
| Comp No. | Structure |
| --- | --- |
| L0186 | 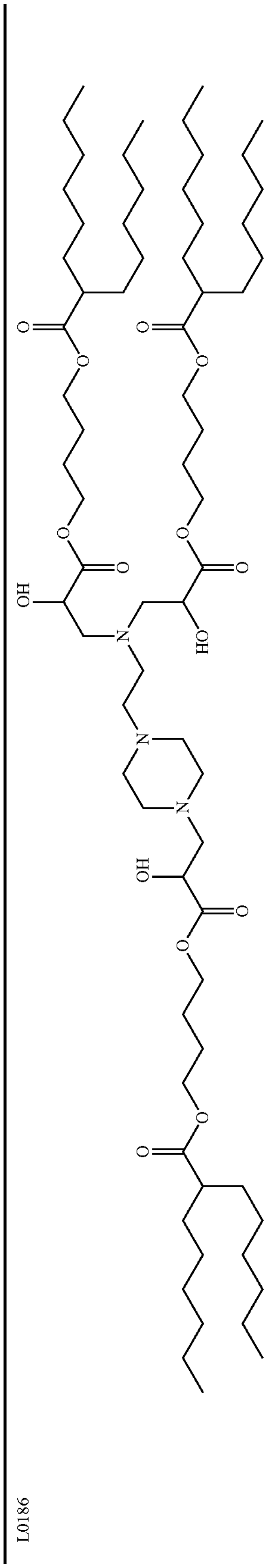 |
| L0187 | 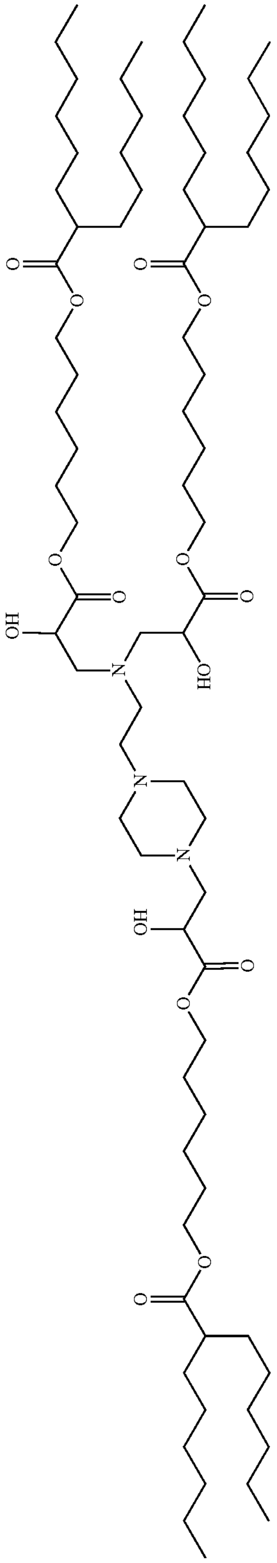 |
| L0188 | 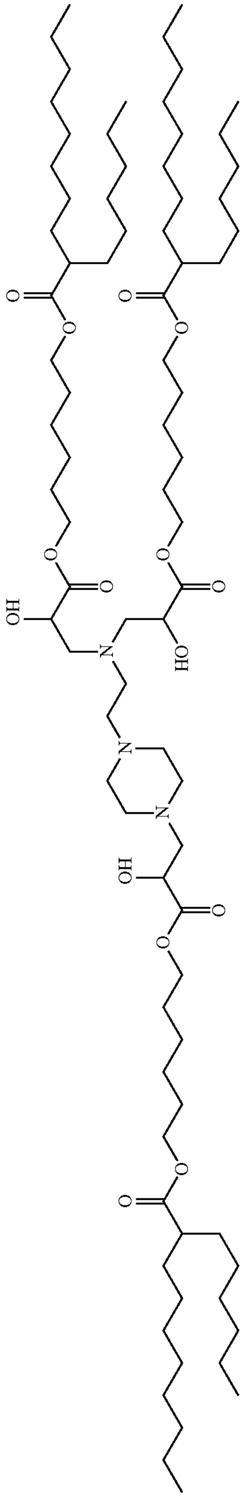 |

TABLE 1A-continued
| Compounds | |
|---|---|
| Comp No. | Structure |
| L0189 | 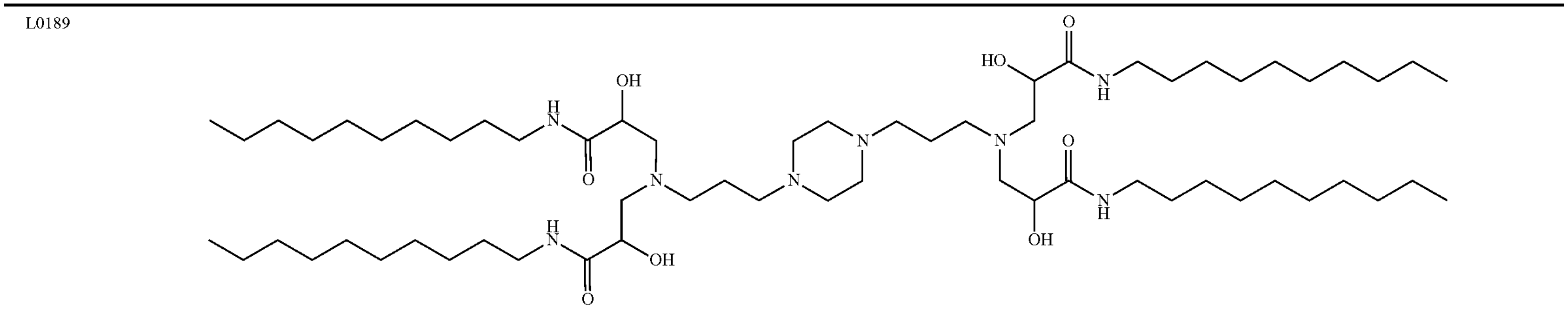 |
| L0190 | 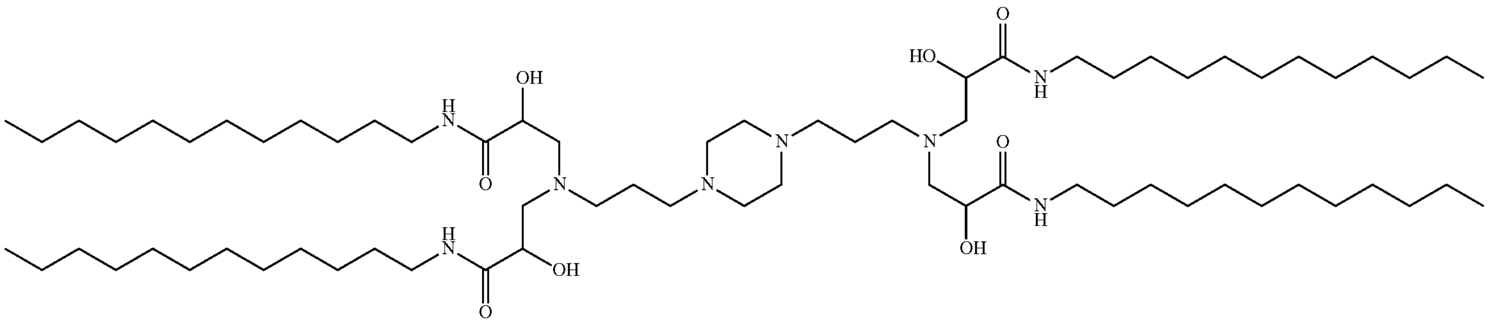 [SMILES: CCCCCCCCCCCCNC(=O)C(O)CN(CCCN1CCN(CCCN(CC(O)C(=O)NCCCCCCCCCCCC)CC(O)C(=O)NCCCCCCCCCCCC)CC1)CC(O)C(=O)NCCCCCCCCCCCC] |
| L0191 | 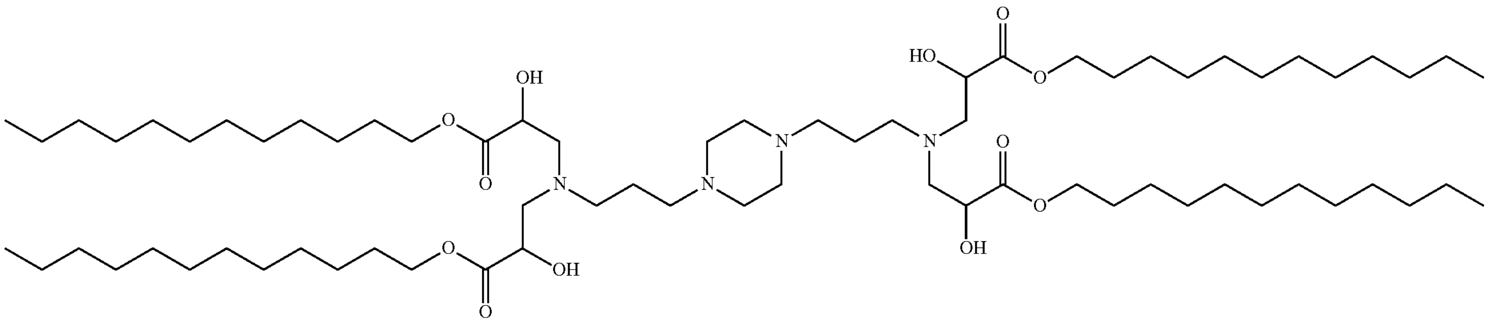 [SMILES: CCCCCCCCCCCCOC(=O)C(O)CN(CCCN1CCN(CCCN(CC(O)C(=O)OCCCCCCCCCCCC)CC(O)C(=O)OCCCCCCCCCCCC)CC1)CC(O)C(=O)OCCCCCCCCCCCC] |

TABLE 1A-continued
| Compounds | |
|---|---|
| Comp No. | Structure |
| L0192 | 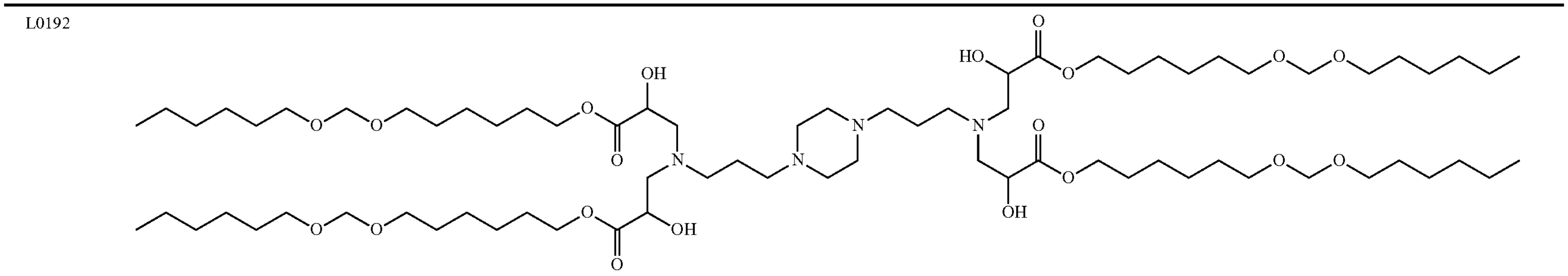 |
| L0193 | 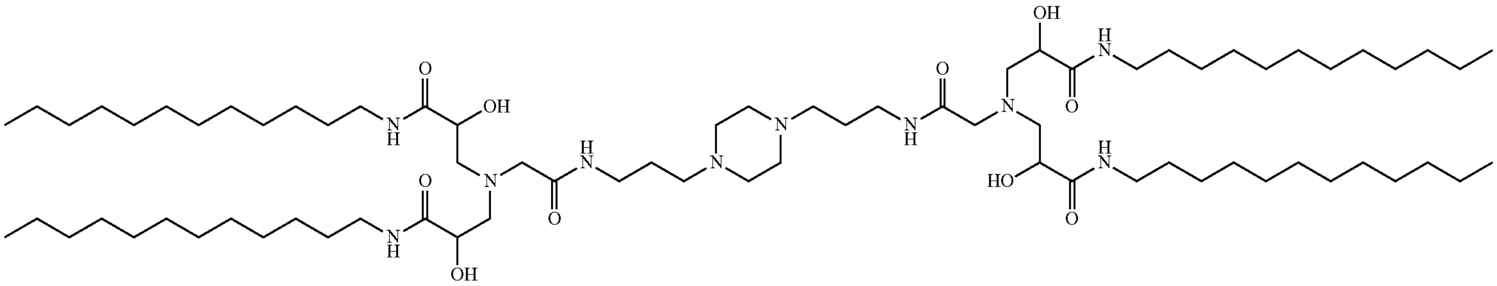 [SMILES: CCCCCCCCCCCCNC(=O)C(O)CN(CC(=O)NCCCN1CCN(CCCNC(=O)CN(CC(O)C(=O)NCCCCCCCCCCCC)CC(O)C(=O)NCCCCCCCCCCCC)CC1)CC(O)C(=O)NCCCCCCCCCCCC] |
| L0194 | 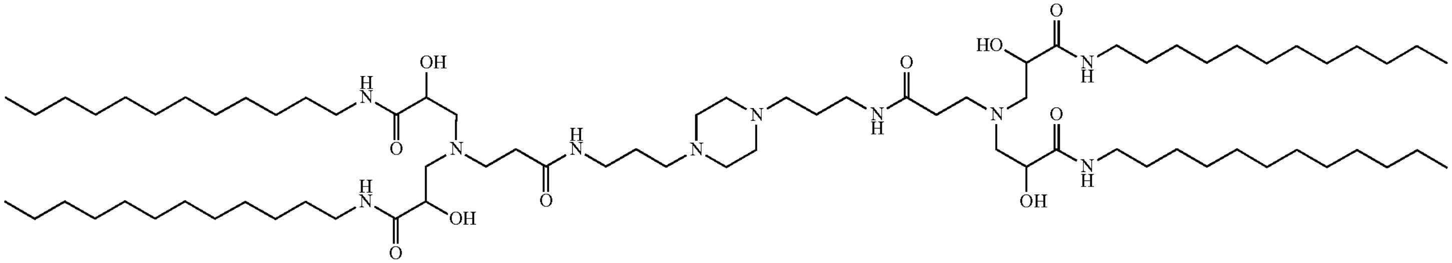 [SMILES: CCCCCCCCCCCCNC(=O)C(O)CN(CCC(=O)NCCCN1CCN(CCCNC(=O)CCN(CC(O)C(=O)NCCCCCCCCCCCC)CC(O)C(=O)NCCCCCCCCCCCC)CC1)CC(O)C(=O)NCCCCCCCCCCCC] |

TABLE 1A-continued
| Compounds | |
| --- | --- |
| Comp No. | Structure |
| L0195 | 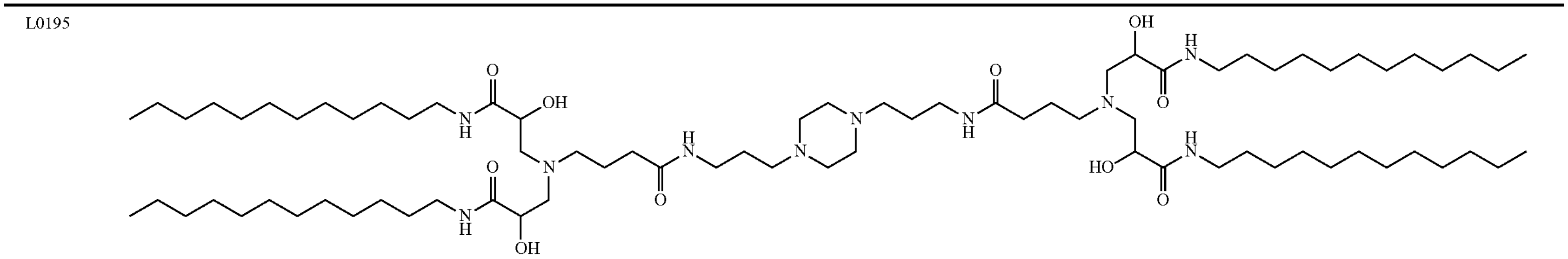 |
| L0196 | 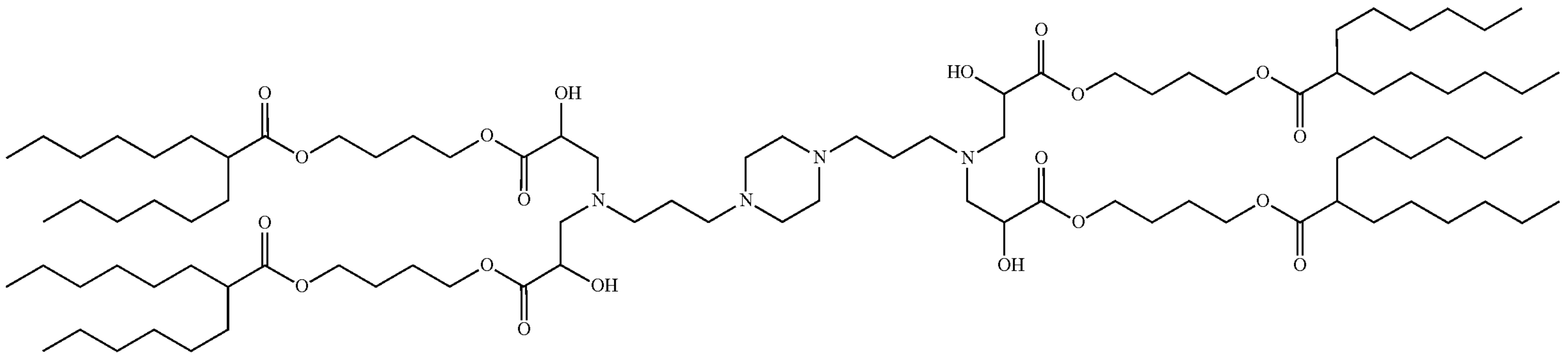 [SMILES: CCCCCCC(CCCCCC)C(=O)OCCCCOC(=O)C(O)CN(CCCN1CCN(CCCN(CC(O)C(=O)OCCCCOC(=O)C(CCCCCC)CCCCCC)CC(O)C(=O)OCCCCOC(=O)C(CCCCCC)CCCCCC)CC1)CC(O)C(=O)OCCCCOC(=O)C(CCCCCC)CCCCCC] |
| L0197 | 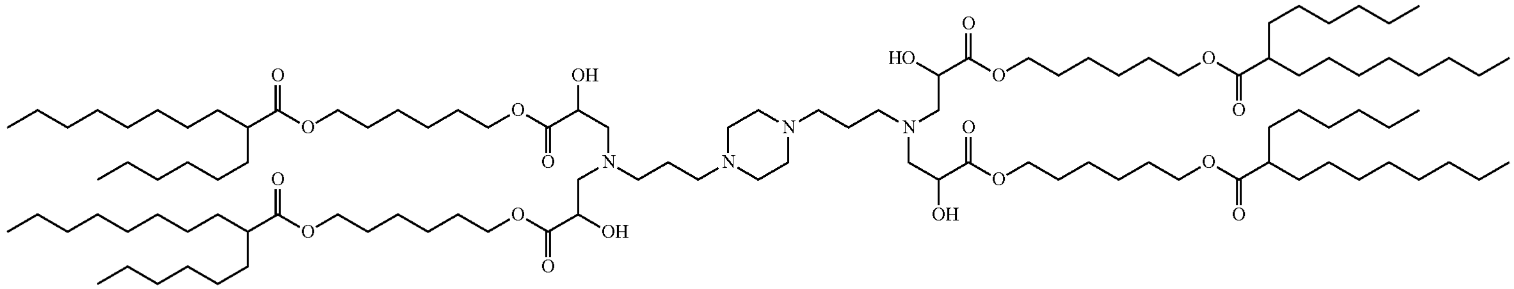 [SMILES: CCCCCCCCC(CCCCCC)C(=O)OCCCCCCOC(=O)C(O)CN(CCCN1CCN(CCCN(CC(O)C(=O)OCCCCCCOC(=O)C(CCCCCC)CCCCCCCC)CC(O)C(=O)OCCCCCCOC(=O)C(CCCCCC)CCCCCCCC)CC1)CC(O)C(=O)OCCCCCCOC(=O)C(CCCCCC)CCCCCCCC] |

TABLE 1A-continued
| Compounds | |
|---|---|
| Comp No. | Structure |
| L0198 | 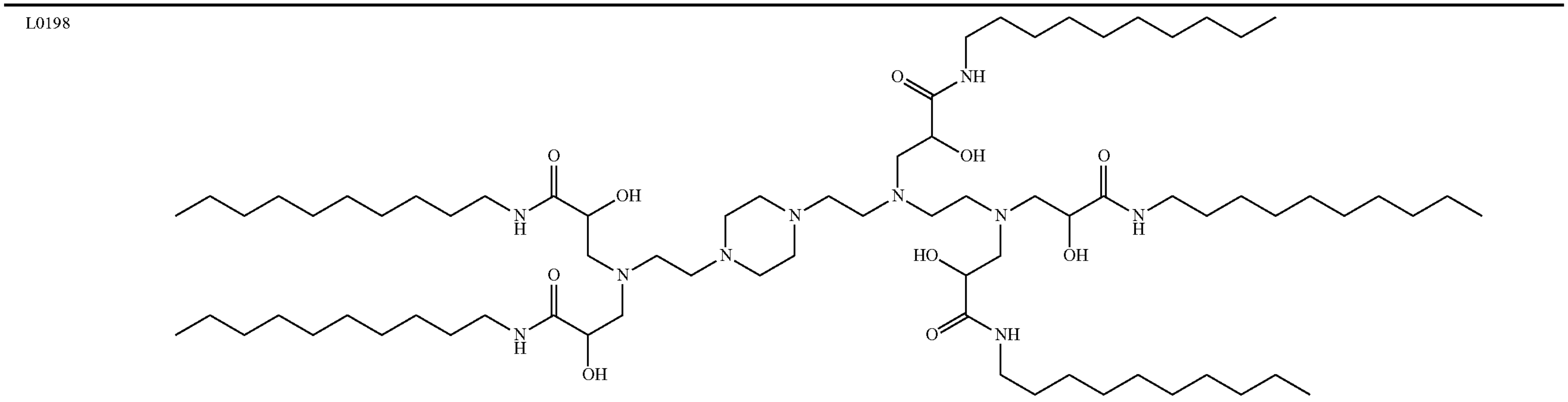 |
| L0199 | 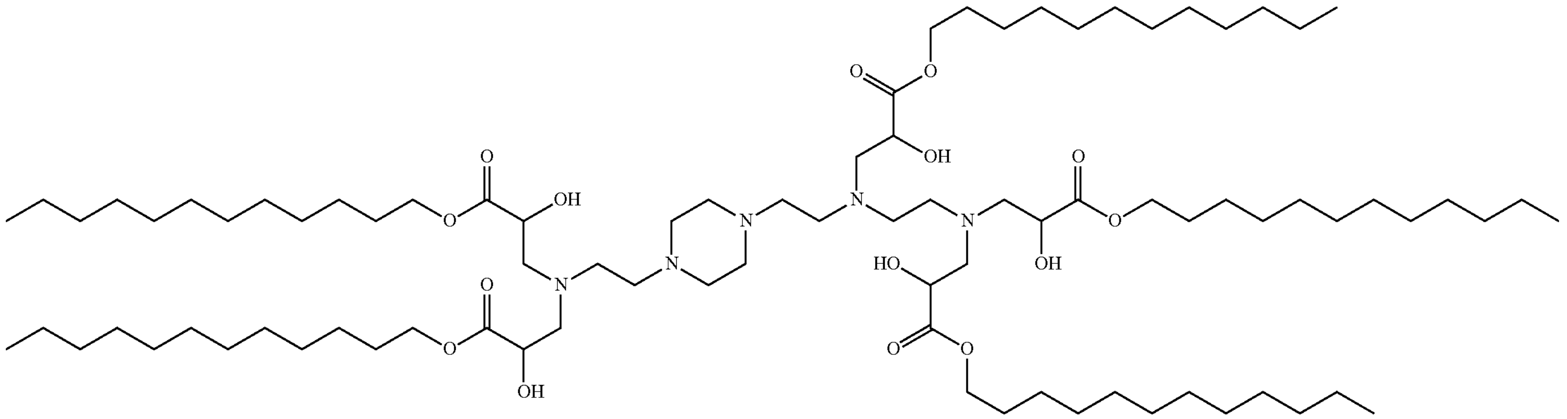 [SMILES: CCCCCCCCCCCCOC(=O)C(O)CN(CCN1CCN(CCN(CC(O)C(=O)OCCCCCCCCCCCC)CC(O)C(=O)OCCCCCCCCCCCC)CC1)CCN(CC(O)C(=O)OCCCCCCCCCCCC)CC(O)C(=O)OCCCCCCCCCCCC] |

TABLE 1A-continued
| Compounds | |
|---|---|
| Comp No. | Structure |
| L0200 | 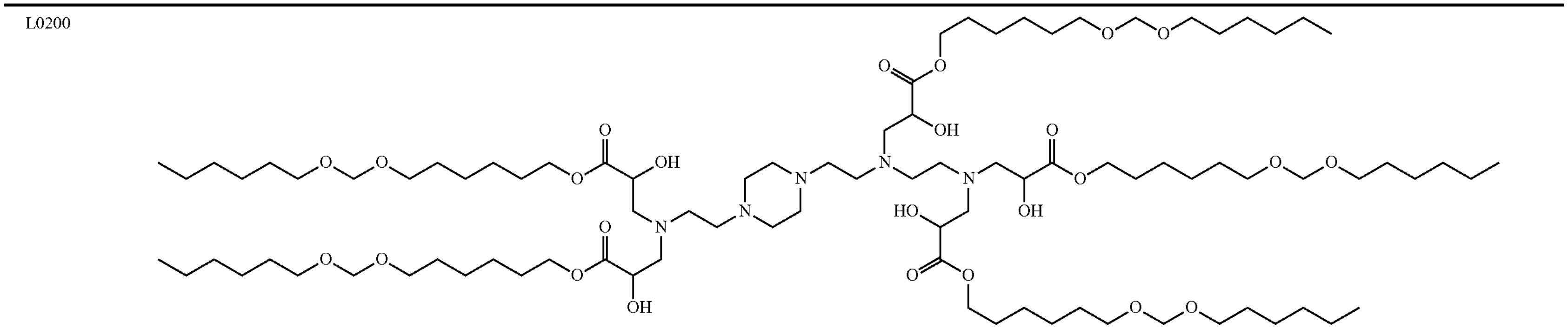 |
| L0201 | 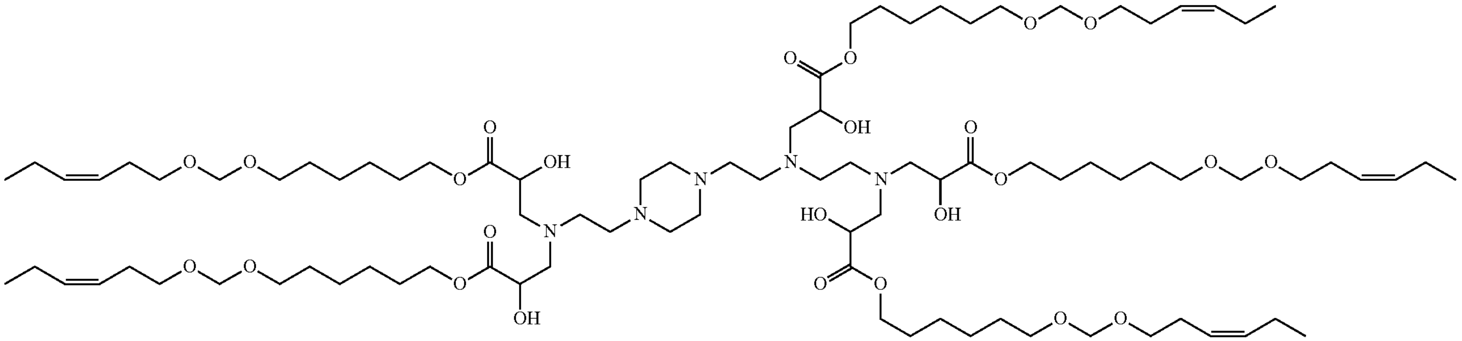 [SMILES: CC/C=C\CCOCOCCCCCCOC(=O)C(O)CN(CCN1CCN(CCN(CC(O)C(=O)OCCCCCCOCOCC/C=C\CC)CC(O)C(=O)OCCCCCCOCOCC/C=C\CC)CC1)CCN(CC(O)C(=O)OCCCCCCOCOCC/C=C\CC)CC(O)C(=O)OCCCCCCOCOCC/C=C\CC] |

TABLE 1A-continued
| Compounds | |
|---|---|
| Comp No. | Structure |
| L0202 | 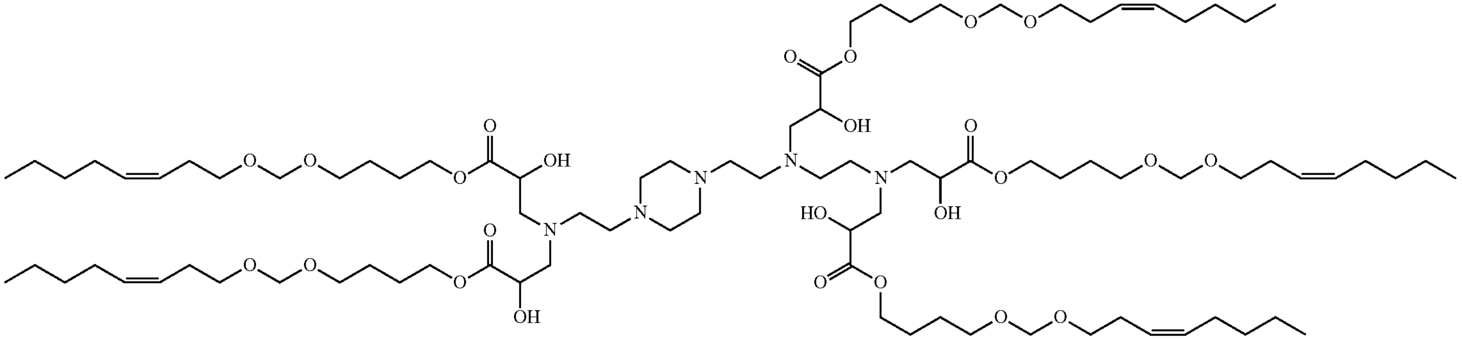 [SMILES: CCCC/C=C\CCOCOCCCCOC(=O)C(O)CN(CCN1CCN(CCN(CC(O)C(=O)OCCCCOCOCC/C=C\CCCC)CC(O)C(=O)OCCCCOCOCC/C=C\CCCC)CC1)CCN(CC(O)C(=O)OCCCCOCOCC/C=C\CCCC)CC(O)C(=O)OCCCCOCOCC/C=C\CCCC] |
| L0203 | 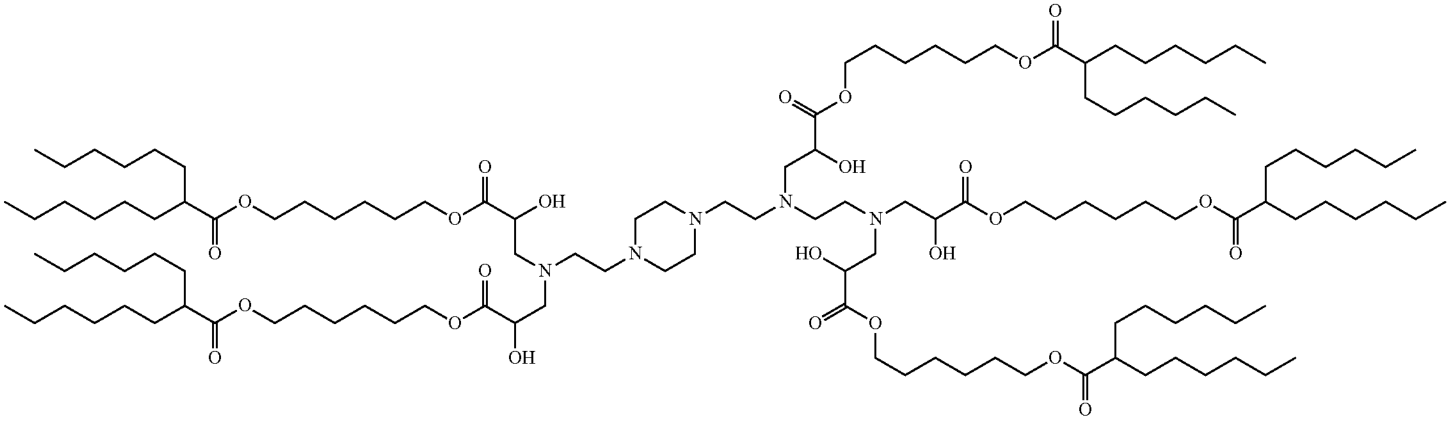 [SMILES: CCCCCCC(CCCCCC)C(=O)OCCCCCCOC(=O)C(O)CN(CCN1CCN(CCN(CC(O)C(=O)OCCCCCCOC(=O)C(CCCCCC)CCCCCC)CC(O)C(=O)OCCCCCCOC(=O)C(CCCCCC)CCCCCC)CC1)CCN(CC(O)C(=O)OCCCCCCOC(=O)C(CCCCCC)CCCCCC)CC(O)C(=O)OCCCCCCOC(=O)C(CCCCCC)CCCCCC] |

TABLE 1A-continued
| Compounds | |
|---|---|
| Comp No. | Structure |
| L0207 | 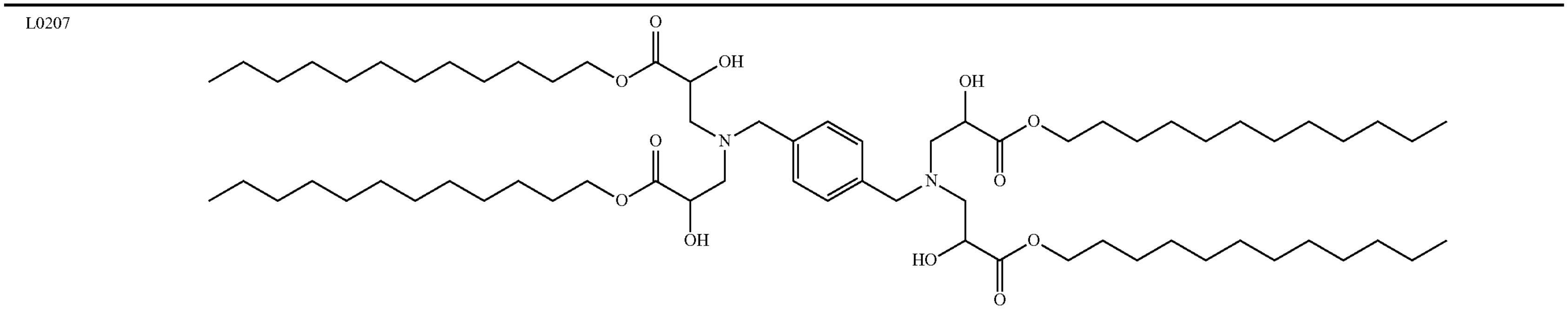 |
| L0208 | 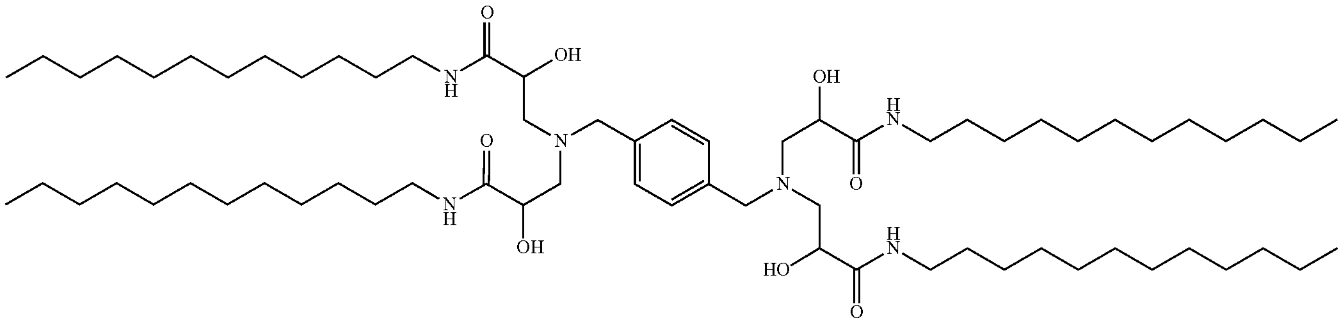 [SMILES: CCCCCCCCCCCCNC(=O)C(O)CN(Cc1ccc(CN(CC(O)C(=O)NCCCCCCCCCCCC)CC(O)C(=O)NCCCCCCCCCCCC)cc1)CC(O)C(=O)NCCCCCCCCCCCC] |
| L0209 | 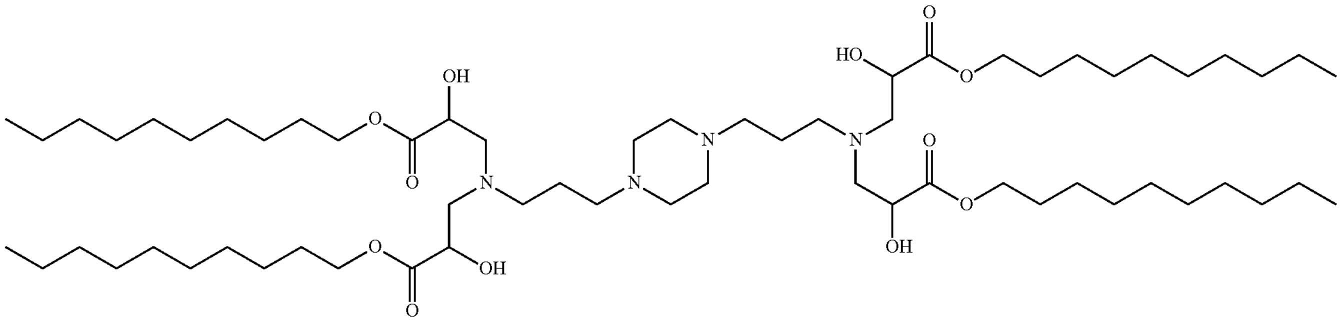 [SMILES: CCCCCCCCCCOC(=O)C(O)CN(CCCN1CCN(CCCN(CC(O)C(=O)OCCCCCCCCCC)CC(O)C(=O)OCCCCCCCCCC)CC1)CC(O)C(=O)OCCCCCCCCCC] |

TABLE 1A-continued
| Compounds | |
|---|---|
| Comp No. | Structure |
| L0210 | 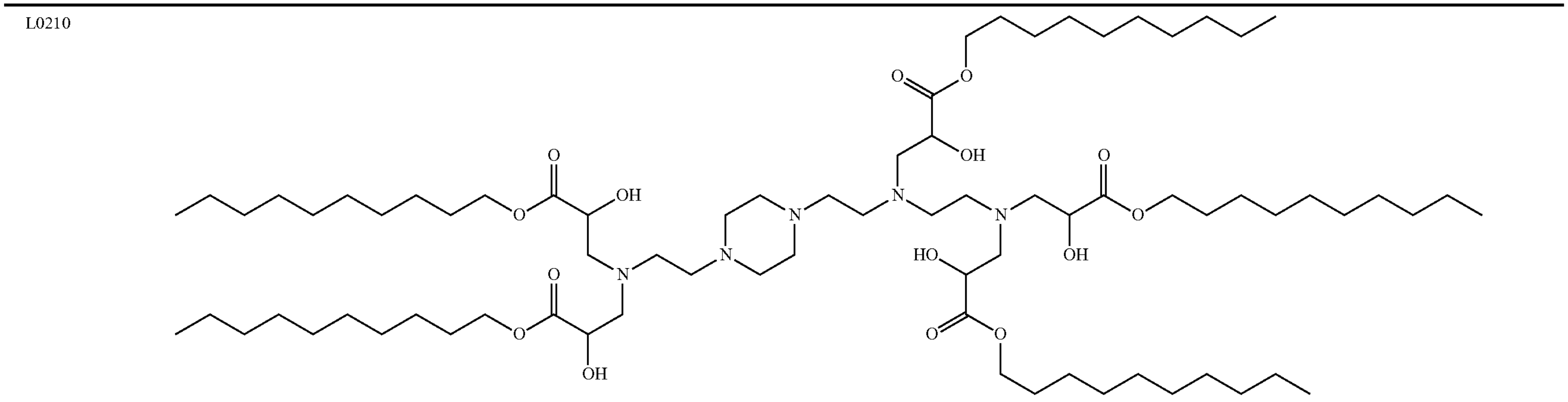 |
| L0211 | 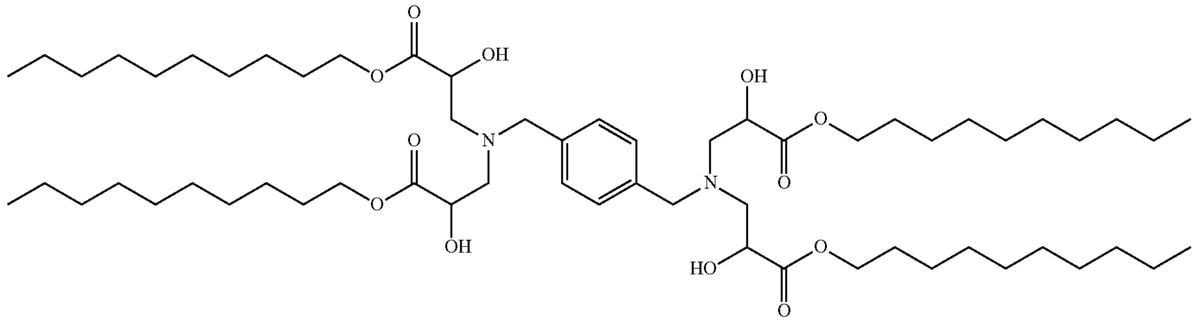 [SMILES: CCCCCCCCCCOC(=O)C(O)CN(Cc1ccc(CN(CC(O)C(=O)OCCCCCCCCCC)CC(O)C(=O)OCCCCCCCCCC)cc1)CC(O)C(=O)OCCCCCCCCCC] |

TABLE 1A-continued
| Compounds | |
|---|---|
| Comp No. | Structure |
| L0212 | 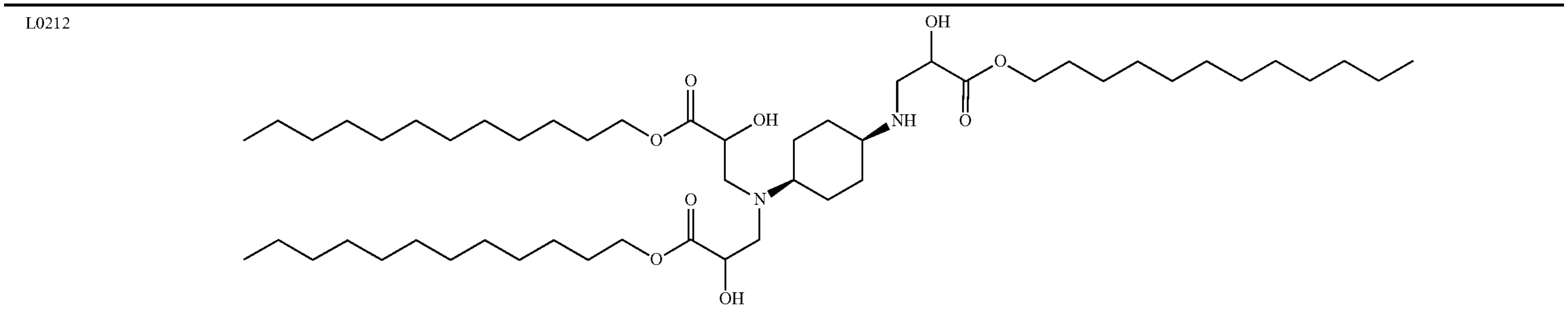 |
| L0213 | 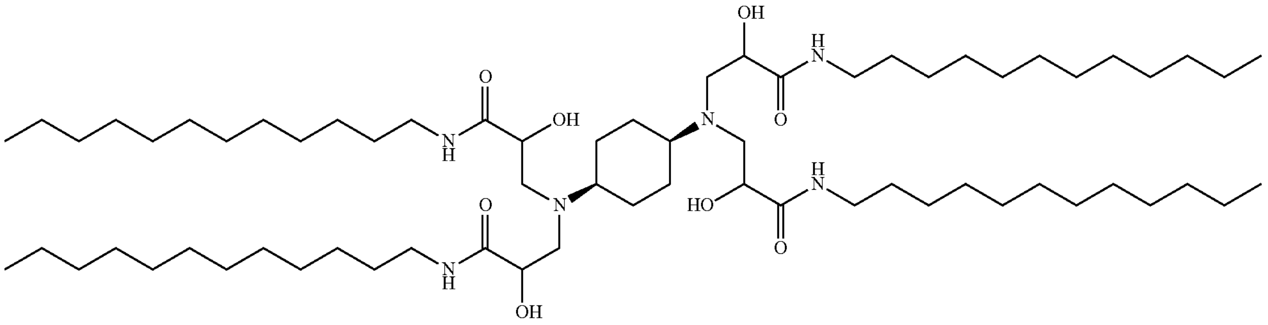 [SMILES: CCCCCCCCCCCCNC(=O)C(O)CN(CC(O)C(=O)NCCCCCCCCCCCC)[C@H]1CC[C@@H](N(CC(O)C(=O)NCCCCCCCCCCCC)CC(O)C(=O)NCCCCCCCCCCCC)CC1] |
| L0214 | 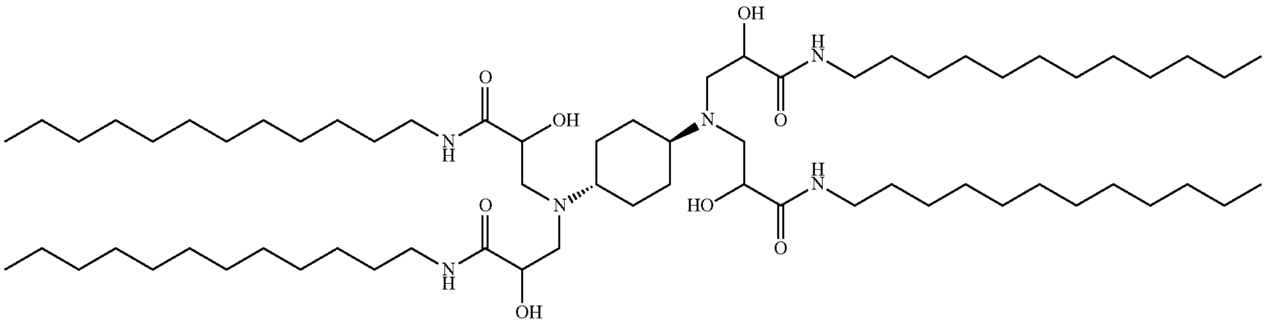 [SMILES: CCCCCCCCCCCCNC(=O)C(O)CN(CC(O)C(=O)NCCCCCCCCCCCC)[C@H]1CC[C@H](N(CC(O)C(=O)NCCCCCCCCCCCC)CC(O)C(=O)NCCCCCCCCCCCC)CC1] |

TABLE 1A-continued
| Compounds | |
|---|---|
| Comp No. | Structure |
| L0215 | 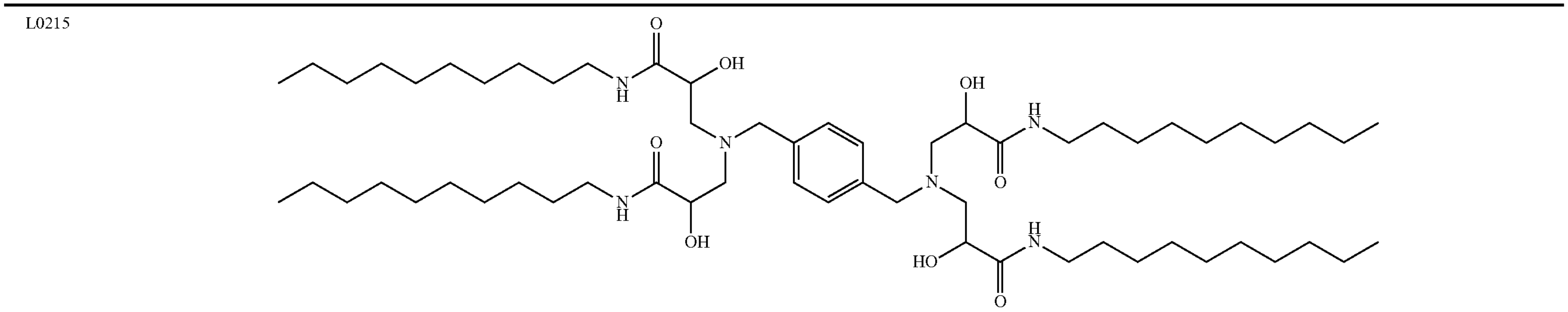 |
| L0216 | 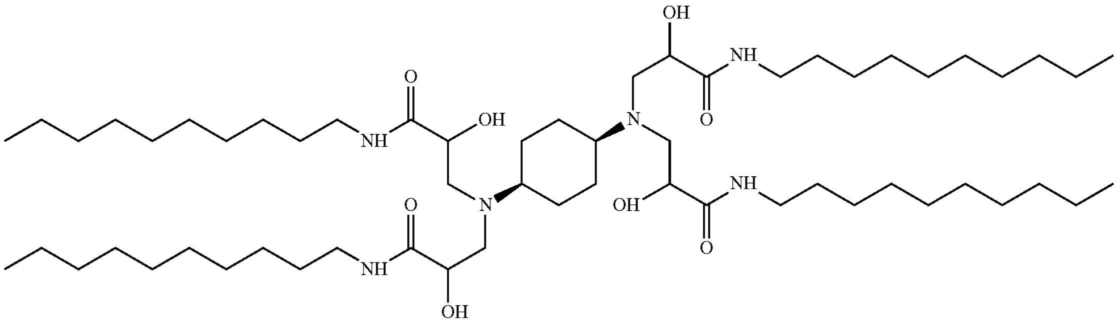 [SMILES: CCCCCCCCCCNC(=O)C(O)CN(CC(O)C(=O)NCCCCCCCCCC)[C@H]1CC[C@@H](N(CC(O)C(=O)NCCCCCCCCCC)CC(O)C(=O)NCCCCCCCCCC)CC1] |
| L0217 | 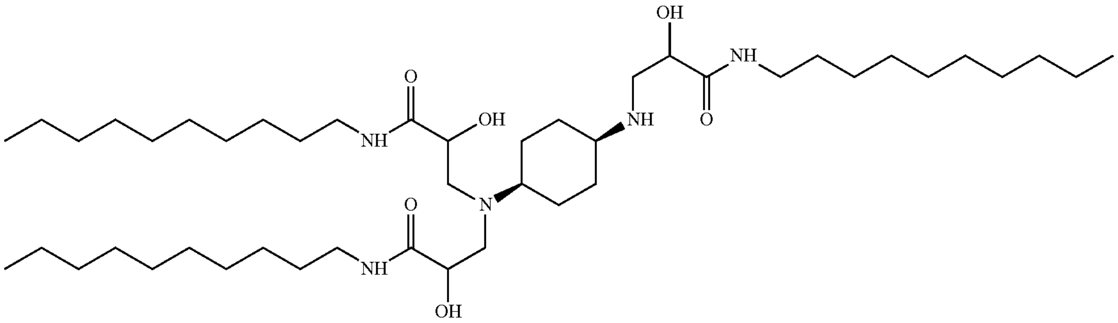 [SMILES: CCCCCCCCCCNC(=O)C(O)CN[C@H]1CC[C@@H](N(CC(O)C(=O)NCCCCCCCCCC)CC(O)C(=O)NCCCCCCCCCC)CC1] |

TABLE 1A-continued
| Compounds | |
|---|---|
| Comp No. | Structure |
| L0218 | 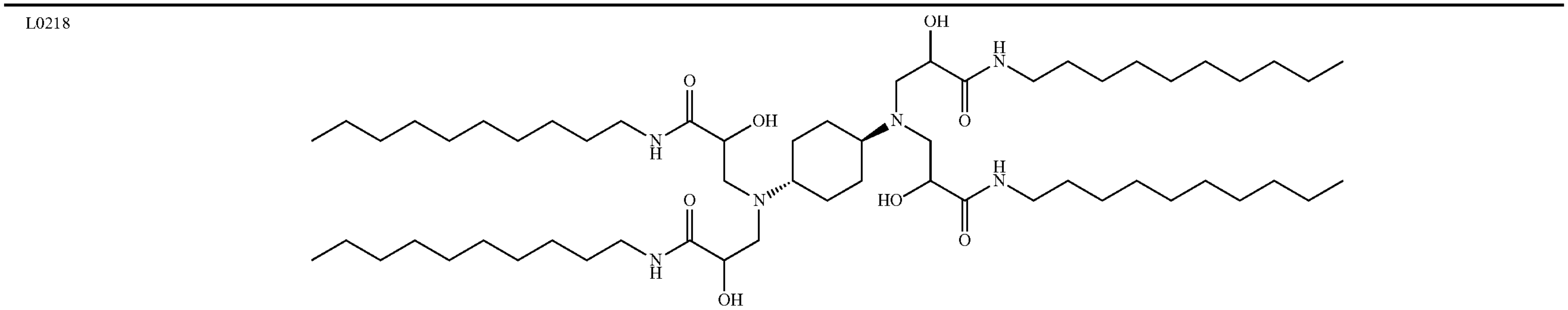 |
| L0219 | 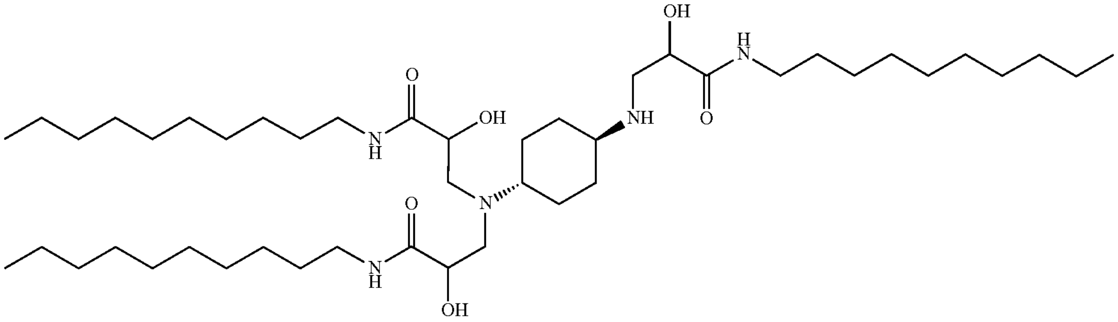 [SMILES: CCCCCCCCCCNC(=O)C(O)CN[C@H]1CC[C@H](N(CC(O)C(=O)NCCCCCCCCCC)CC(O)C(=O)NCCCCCCCCCC)CC1] |
| L0220 | 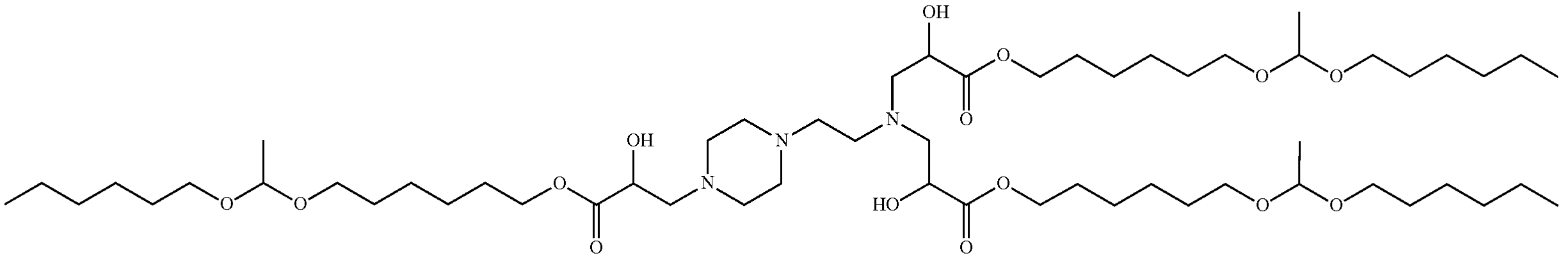 [SMILES: CCCCCCOC(C)OCCCCCCOC(=O)C(O)CN1CCN(CCN(CC(O)C(=O)OCCCCCCOC(C)OCCCCCC)CC(O)C(=O)OCCCCCCOC(C)OCCCCCC)CC1] |

TABLE 1A-continued
| Compounds | |
|---|---|
| Comp No. | Structure |
| L0221 | 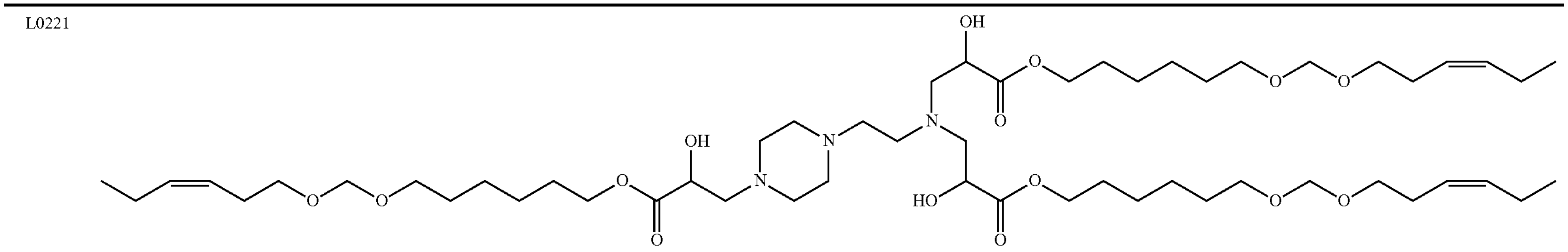 |
| L0222 | 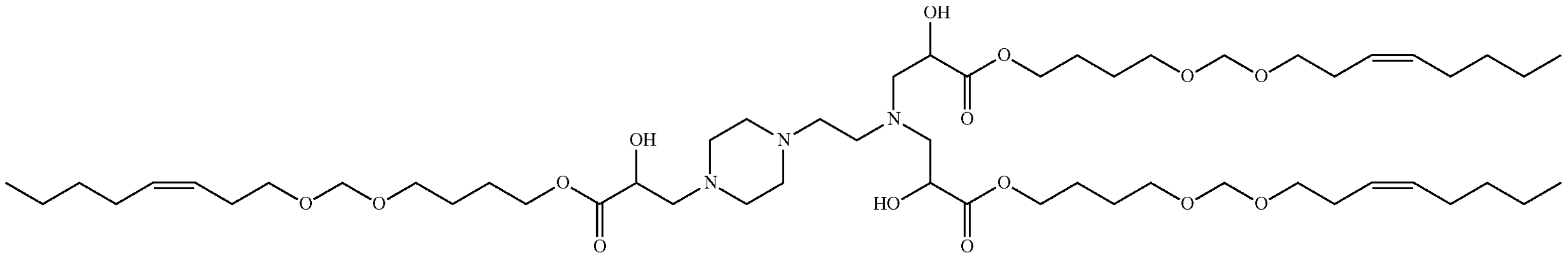 [SMILES: CCCC/C=C\CCOCOCCCCOC(=O)C(O)CN1CCN(CCN(CC(O)C(=O)OCCCCOCOCC/C=C\CCCC)CC(O)C(=O)OCCCCOCOCC/C=C\CCCC)CC1] |
| L0223 | 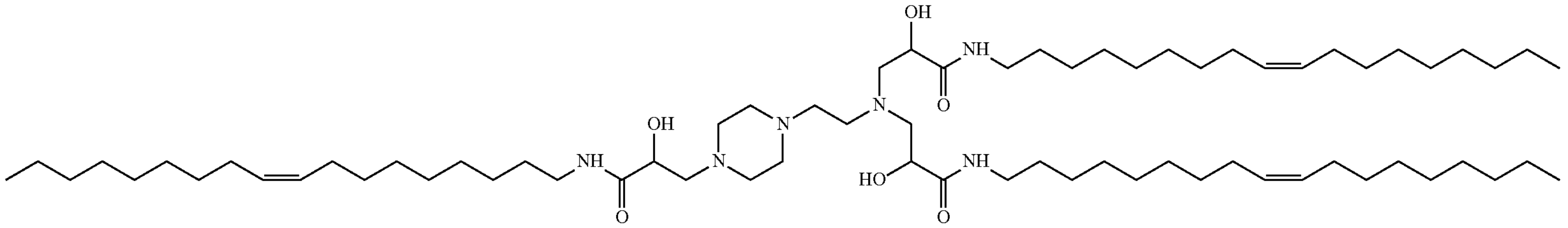 [SMILES: CCCCCCCC/C=C\CCCCCCCCNC(=O)C(O)CN1CCN(CCN(CC(O)C(=O)NCCCCCCCC/C=C\CCCCCCCC)CC(O)C(=O)NCCCCCCCC/C=C\CCCCCCCC)CC1] |

TABLE 1A-continued
| Compounds | |
| --- | --- |
| Comp No. | Structure |
| L0224 | 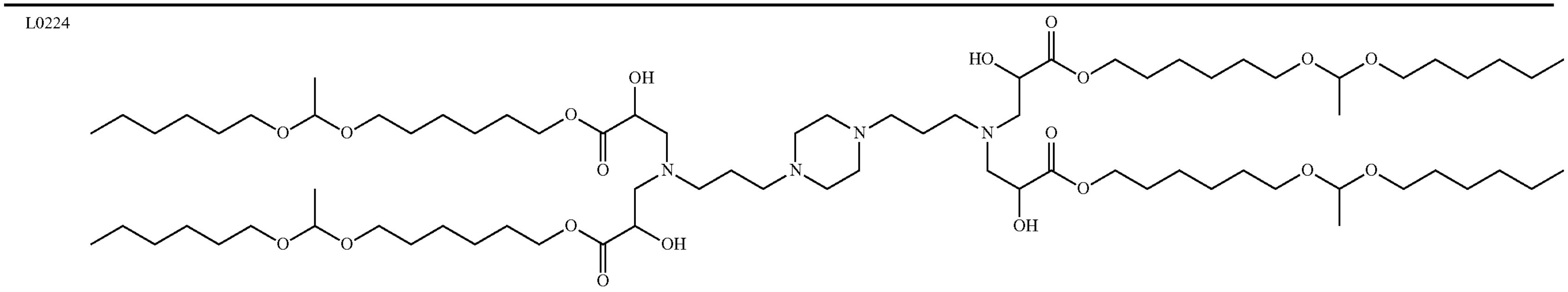 |
| L0225 | 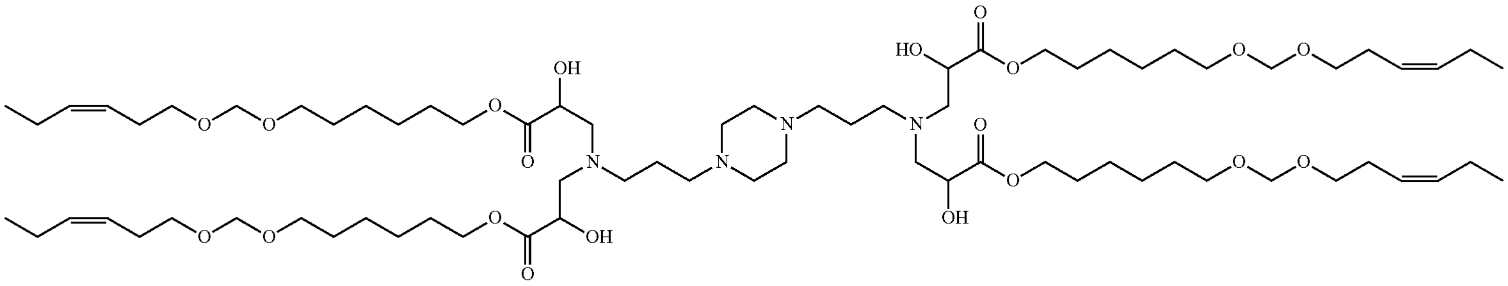 [SMILES: CC/C=C\CCOCOCCCCCCOC(=O)C(O)CN(CCCN1CCN(CCCN(CC(O)C(=O)OCCCCCCOCOCC/C=C\CC)CC(O)C(=O)OCCCCCCOCOCC/C=C\CC)CC1)CC(O)C(=O)OCCCCCCOCOCC/C=C\CC] |
| L0226 | 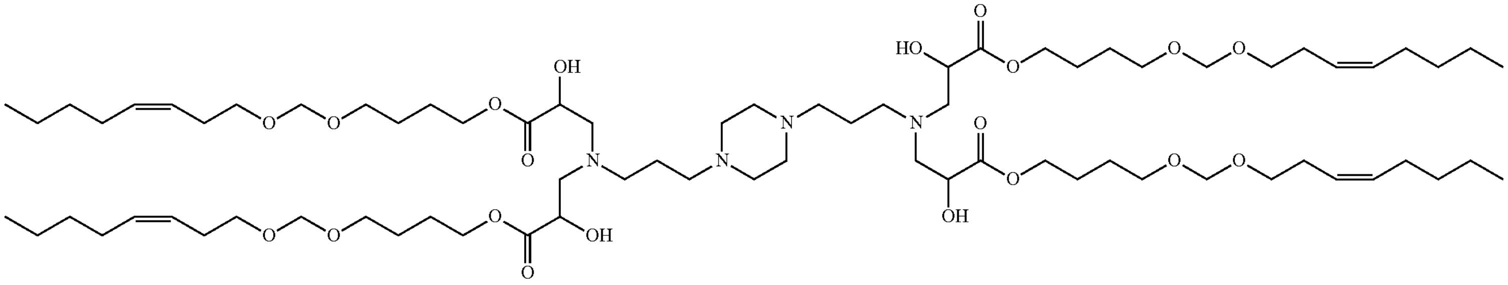 [SMILES: CCCC/C=C\CCOCOCCCCOC(=O)C(O)CN(CCCN1CCN(CCCN(CC(O)C(=O)OCCCCOCOCC/C=C\CCCC)CC(O)C(=O)OCCCCOCOCC/C=C\CCCC)CC1)CC(O)C(=O)OCCCCOCOCC/C=C\CCCC] |

TABLE 1A-continued
| Compounds | |
| --- | --- |
| Comp No. | Structure |
| L0227 | 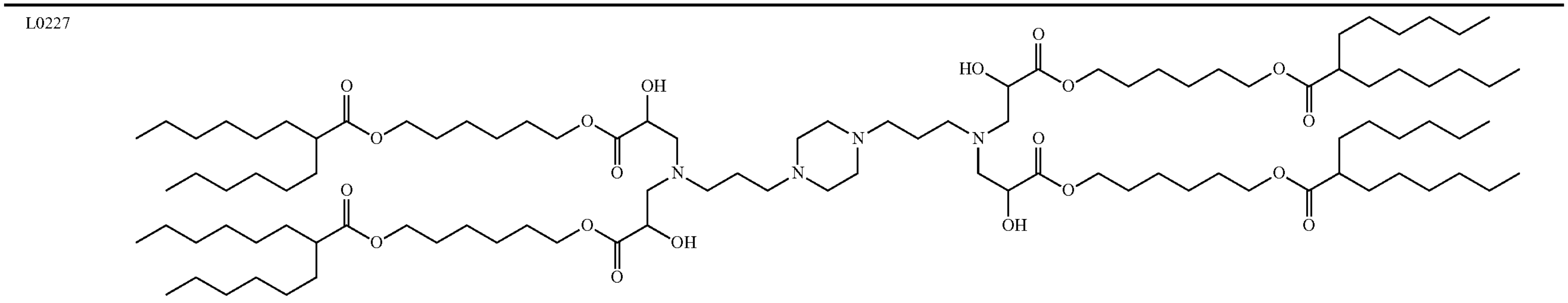 |
| L0228 | 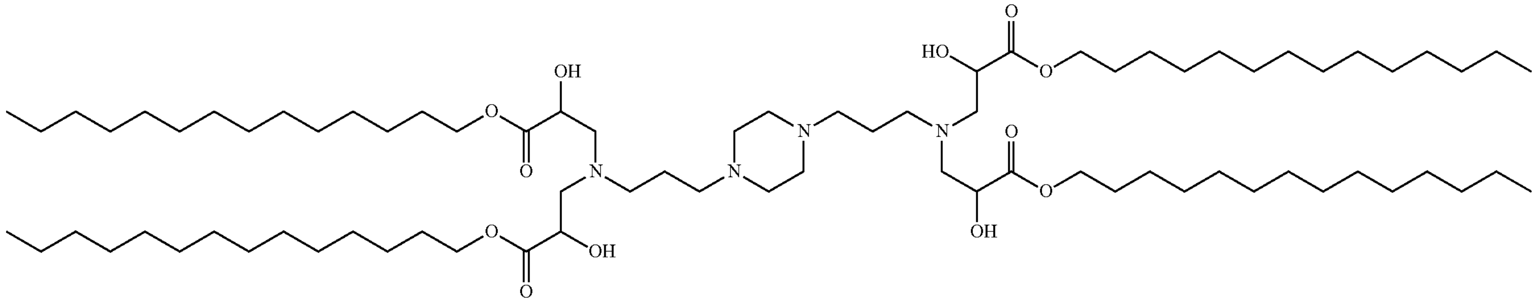 [SMILES: CCCCCCCCCCCCCCOC(=O)C(O)CN(CCCN1CCN(CCCN(CC(O)C(=O)OCCCCCCCCCCCCCC)CC(O)C(=O)OCCCCCCCCCCCCCC)CC1)CC(O)C(=O)OCCCCCCCCCCCCCC] |
| L0229 | 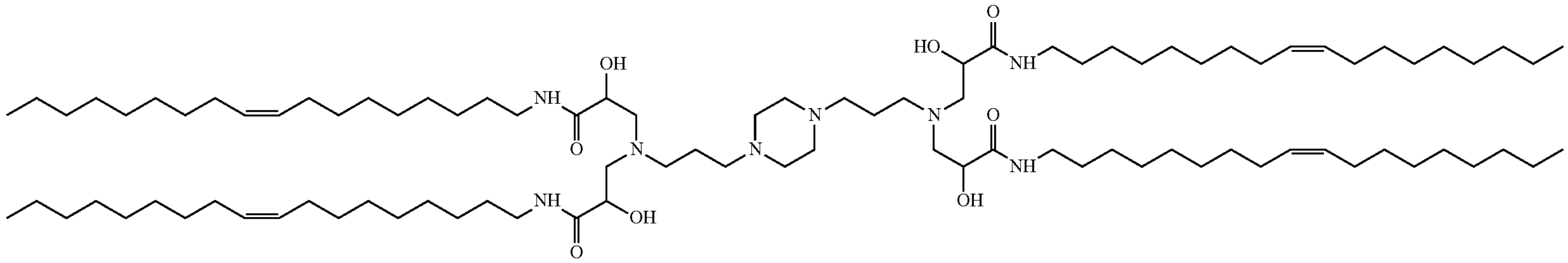 [SMILES: CCCCCCCC/C=C\CCCCCCCCNC(=O)C(O)CN(CCCN1CCN(CCCN(CC(O)C(=O)NCCCCCCCC/C=C\CCCCCCCC)CC(O)C(=O)NCCCCCCCC/C=C\CCCCCCCC)CC1)CC(O)C(=O)NCCCCCCCC/C=C\CCCCCCCC] |

TABLE 1B
| Comparator Compounds | |
|---|---|
| Comp No. | Structure |
| L0191-Control | 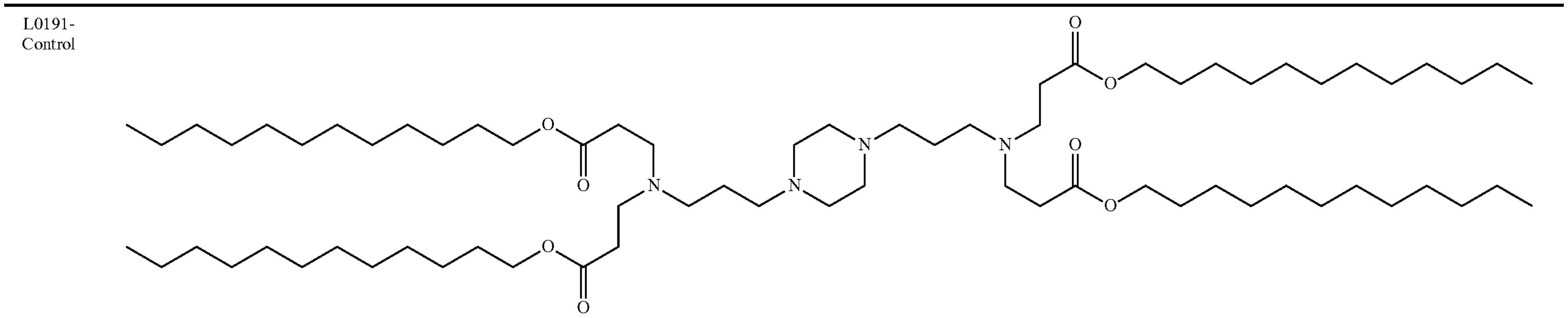 |
| L0199-Control | 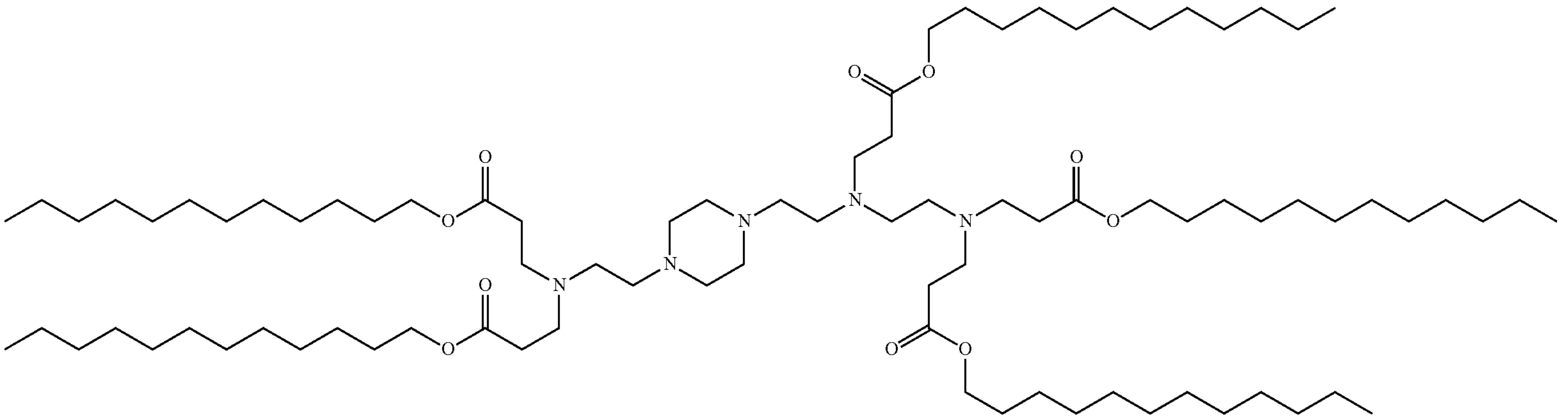 [SMILES: CCCCCCCCCCCCOC(=O)CCN(CCC(=O)OCCCCCCCCCCCC)CCN(CCC(=O)OCCCCCCCCCCCC)CCN1CCN(CCN(CCC(=O)OCCCCCCCCCCCC)CCC(=O)OCCCCCCCCCCCC)CC1] |

Lipid Nanoparticles and Compositions

The term "lipid nanoparticle" refers to particles having at least one dimension on the order of nanometers (e.g., 1-1,000 nm) which include one or more of the compounds of Formula I, or a pharmaceutically acceptable salt, stereoisomer, or mixture of stereoisomers thereof (e.g., a compound of Table IA, or a pharmaceutically acceptable salt, stereoisomer, or mixture of stereoisomers thereof). Nanoparticle compositions include, for example, lipid nanoparticles (LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or crosslinked to one another. Lipid bilayers may include one or more ligands, proteins, or channels.

In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticle comprises a nucleic acid. Such lipid nanoparticles typically comprise a compound of Formula I, or a pharmaceutically acceptable salt, stereoisomer, or mixture of stereoisomers thereof (e.g., a compound of Table TA, or a pharmaceutically acceptable salt, stereoisomer, or mixture of stereoisomers thereof) and one or more excipient, such as a steroid or lipid, e.g., a neutral lipid, charged lipid (e.g., cationic lipids, steroid, or polymer conjugated lipid.

A "cationic lipid" refers to a lipid capable of being positively charged. Exemplary cationic lipids include one or more amine group(s) which bear the positive charge. Exemplary cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form endosomolytic non-bilayer structures (Hafez, I. M., et al., Gene Ther 8:1188-1196 (2001)) critical to the intracellular delivery of nucleic acids.

In a particular embodiment, the present disclosure provides a nanoparticle composition or formulation that includes a compound of the present disclosure, a phospholipid, a structural lipid, a polyethylene glycol (PEG) lipid, or a combination thereof.

As used herein, a "phospholipid" is a lipid that includes a phosphate moiety and one or more carbon chains, such as unsaturated fatty acid chains. A phospholipid may include one or more multiple (e.g., double or triple) bonds. Non-limiting examples of phospholipid include 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-OT-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanol amine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and combinations thereof.

In some embodiments, the phospholipid is DOPE. In some embodiments, the phospholipid is DSPC.

In some embodiments, the composition includes a structural lipid. Non-limiting examples of structural lipid include cholesterol, fecosterol, sitosterol, ergosterol, campesterol, stigmasterol, brassicasterol, tomatidine, ursolic acid, alpha-tocopherol, and combinations thereof. In one embodiment, the structural lipid is cholesterol.

In some embodiments, the composition includes a PEG lipid. Non-limiting examples of PEG lipid include a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and combinations thereof.

In a particular embodiment, a nanoparticle composition of the present disclosure includes a compound of Formula I, 1,2-distearoyl-sn-glycero-3-phosphocholine (DSPC), cholesterol and myristoyl diglyceride-$PEG_{2000}$ (DMG-PEG2K).

Ingredients of the nanoparticle composition (e.g., DMG-PEG2K, DSPC, cholesterol and the compound) can be combined to yield certain molar ratios or mass ratios (see, for example Table 2). In one embodiment, the DMG-PEG2K, DSPC, cholesterol and the compound of Formula I have a molar ratio of (0.5 to 5):(1 to 30):(10 to 70):(15 to 75). In another embodiments, the DMG-PEG2K, DSPC, cholesterol and the compound of Formula I have a molar ratio of (0.8 to 3):(3 to 25):(15 to 65):(20 to 70). In another embodiments, the DMG-PEG2K, DSPC, cholesterol and the compound of Formula I have a molar ratio of (0.95 to 2.5):(4 to 20):(17.50 to 59.50):(25 to 65).

As provided, the nanoparticle composition can optionally include a therapeutic or prophylactic agent. The therapeutic or prophylactic agent may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g., an adverse immune response.

The term "therapeutic agent" or "prophylactic agent" refers to any agent that, when administered to a subject, has a therapeutic, diagnostic, and/or prophylactic effect and/or elicits a desired biological and/or pharmacological effect. Examples of the therapeutic or prophylactic agent include, without limitation, a small molecule drug, a protein, a cell or a nucleic acid.

In some embodiments, the therapeutic or prophylactic agent is a nucleic acid, such as deoxyribonucleic acid (DNA) or ribonucleic acid (RNA). Examples of RNA include, without limitation, a small interfering RNA (siRNA), an asymmetrical interfering RNA (aiRNA), a microRNA (miRNA), a Dicer-substrate RNA (dsRNA), a small hairpin RNA (shRNA), a circular RNA (circRNA), a messenger RNA (mRNA), and combinations thereof.

In some embodiments, the therapeutic or prophylactic agent is an mRNA, which optionally includes one or more of a stem loop, a chain terminating nucleoside, a poly(A) sequence, a polyadenylation signal, and a 5' cap.

In some embodiments, the nanoparticle composition has a desired N:P ratio. As used herein, the "N:P ratio" is the molar ratio of ionizable (in the physiological pH range) nitrogen atoms in a lipid to phosphate groups in an RNA, e.g., in a nanoparticle composition including a lipid component and an RNA.

In some embodiments, the N:P ratio is from 5 to 100. In some embodiments, the N:P ratio is from 10 to 60.

mRNAs may be synthesized according to any of a variety of known methods. For example, the mRNAs may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of an mRNA, a DNA template is transcribed in vitro. A suitable DNA template typically has a promoter, for example a T3, T7 or SP6 promoter, for in vitro transcription, followed by desired nucleotide sequence for the mRNA and a termination signal.

The mRNA may be synthesized as unmodified or modified mRNA. Typically, mRNAs are modified to enhance stability. Modifications of mRNA can include, for example, modifications of the nucleotides of the RNA. A modified mRNA can thus include, for example, backbone modifications, sugar modifications or base modifications. In some embodiments, protein encoding mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, 13-D-mannosyl-queosine, wybutoxosine, and phosphoramidates, phosphorothioates, peptide nucleotides, methylphosphonates, 7-deazaguanosine, 5-methylcytosine and inosine.

In some embodiments, the mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, the mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, the mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, the mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5)A and G(5)ppp(5')G.

In some embodiments, the mRNAs include a 3' poly(A) tail structure. A poly-A tail on the 3' terminus of mRNA typically includes about 10 to 300 adenosine nucleotides (e.g., about 10 to 200 adenosine nucleotides, about 10 to 175 adenosine nucleotides, about 10 to 150 adenosine nucleotides, about 10 to 125 adenosine nucleotides, 10 to 100 adenosine nucleotides, about 10 to 75 adenosine nucleotides, about 20 to 70 adenosine nucleotides, or about 20 to 60 adenosine nucleotides). In some embodiments, antibody encoding mRNAs (e.g., heavy chain and light chain encoding mRNAs) include a 3' poly(C) tail structure. A suitable poly-C tail on the 3' terminus of mRNA typically includes about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length (e.g., about 50 and 400 nucleotides in length, about 50 and 300 nucleotides in length, about 50 and 200 nucleotides in length, or about 50 and 100 nucleotides in length).

In some embodiments, a 5' region of an mRNA includes a sequence encoding a signal peptide, such as those described herein. In particular embodiments, a signal peptide derived from human growth hormone (hGH) is incorporated in the 5' region. Typically, a signal peptide encoding sequence is linked, directly or indirectly, to the heavy chain or light chain encoding sequence at the N-terminus.

In various embodiments, the lipid nanoparticles in the composition have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease.

The characteristics of a nanoparticle composition may depend on the components thereof. For example, a nanoparticle composition including cholesterol as a structural lipid may have different characteristics than a nanoparticle composition that includes a different structural lipid. Similarly, the characteristics of a nanoparticle composition may depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes.

A nanoparticle composition may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition of the present disclosure may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition of the present disclosure may be from about−10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic describes the amount of therapeutic and/or prophylactic that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic and/or prophylactic in a solution containing the nanoparticle composition before and after breaking up the nanoparticle composition with one or more organic solvents or detergents. Fluorescence may be used to measure the amount of free therapeutic and/or prophylactic (e.g., RNA) in a solution. For the nanoparticle compositions described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis or infection) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

In certain embodiments, the compounds provided herein can be used in the preparation of lipid nanoparticles for the administration of a vaccine, such as an mRNA vaccine. As such, provided herein is a method for preventing a disease or disorder, comprising administering a lipid nanoparticle as disclosed herein to a subject in need thereof, wherein the lipid nanoparticle comprises one or more small molecule drug, protein, cell and/or nucleic acid (e.g., DNA and mRNA).

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

In accordance with one embodiment of the present disclosure, provided is a method of delivering a therapeutic or prophylactic agent to a mammalian cell, the method entailing contacting the cell with a nanoparticle composition of the present disclosure that includes the therapeutic or prophylactic agent.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modem Pharmaceutics, Marcel Dekker, Inc. 3rd Ed. (G. S. Banker & C. T. Rhodes, Eds.).

For the purposes of administration, the compounds of the present invention (typically in the form of lipid nanoparticles in combination with a therapeutic agent) may be administered as a raw chemical or may be formulated as pharmaceutical compositions. Pharmaceutical compositions of the present invention comprise a compound of Formula I and one or more pharmaceutically acceptable carrier, diluent or excipient. The compound of Formula I is present in the composition in an amount which is effective to form a lipid nanoparticle and deliver the therapeutic agent, e.g., for treating a particular disease or condition of interest. Appropriate concentrations and dosages can be readily determined by one skilled in the art.

In some embodiments, the lipid nanoparticle further comprises a phospholipid, a polyethylene glycol lipid, cholesterol, or a combination thereof. In some embodiments, the phospholipid is 1,2-distearoyl-sn-glycero-3-phosphocholine. In some embodiments, the polyethylene glycol lipid is myristoyl diglyceride-$PEG_{2000}$ (DMG-$PEG_{2000}$).

The lipid nanoparticles as disclosed herein are typically administered via parenteral administration. The term parenteral as used herein includes subcutaneous injections, intravenous, intramuscular, intradermal, intravaginal, intranasal, intrastemal injection or infusion techniques.

Pharmaceutical compositions for parenteral administration are typically formulated so as to allow the active ingredients contained therein to be bioavailable upon administration of the composition to a subject. Compositions that will be administered to a subject or patient take the form of one or more dosage units.

Dosing

The specific dose level of a therapeutic agent (e.g., a nucleic acid such as mRNA) of the present application for any particular subject will depend upon a variety of factors including the activity of the specific compound employed, the age, body weight, general health, sex, diet, time of administration, route of administration, and rate of excretion, and the severity of the particular disease in the subject undergoing therapy. For example, a dosage may be expressed as a number of milligrams of a therapeutic agent (e.g., a nucleic acid such as mRNA) per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of therapeutic agent (e.g., a nucleic acid such as mRNA) administered per dose or per day. Daily dosage may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The compounds of the present application or the compositions thereof may be administered once, twice, three, or four times daily, using any suitable mode described above. Also, administration or treatment with the therapeutic agent (e.g., a nucleic acid such as mRNA) may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a therapeutic agent (e.g., a nucleic acid such as mRNA) and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

It will be appreciated that where typical process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

General Synthesis Method I

The following Schemes illustrate general methods which can be employed for the synthesis of compounds disclosed herein. In Scheme I, each $L^1$, $L^2$, ring A, Y, n, R, $R^1$, $R^2$, and L, are independently as defined herein, $R^{21}$ is $R^1$ (e.g., H) or a precursor thereto, such as -L-$NH_2$, and $R^{20}$ is $R^2$ or a precursor thereto, such as when $R^{20}$ is —H in compound I-1, then $R^{22}$ is —$CH_2$—CH(OH)C(O)OH in compounds I-3, I-5, I-6, or I; or when $R^{20}$ is $NH_2$ in compound I-1, then $R^{22}$ is —NH—$CH_2$—CH(OH)C(O)OH or —N($CH_2$—CH(OH)C(O)OH$)_2$ in compounds I-3, I-5, I-6, or I).

Scheme I

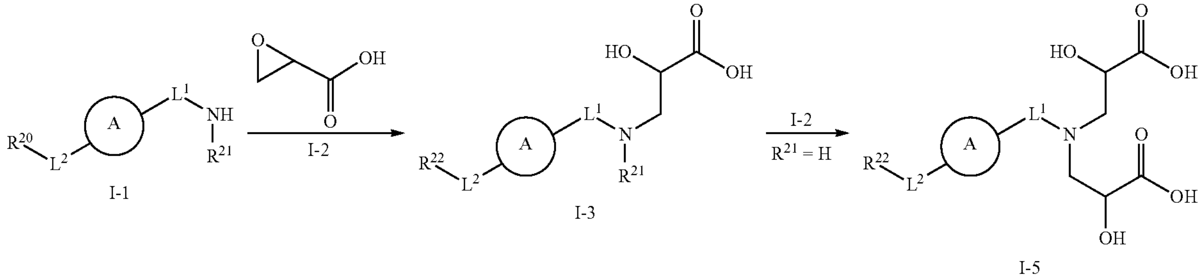

I-1
I-3
I-5

-continued

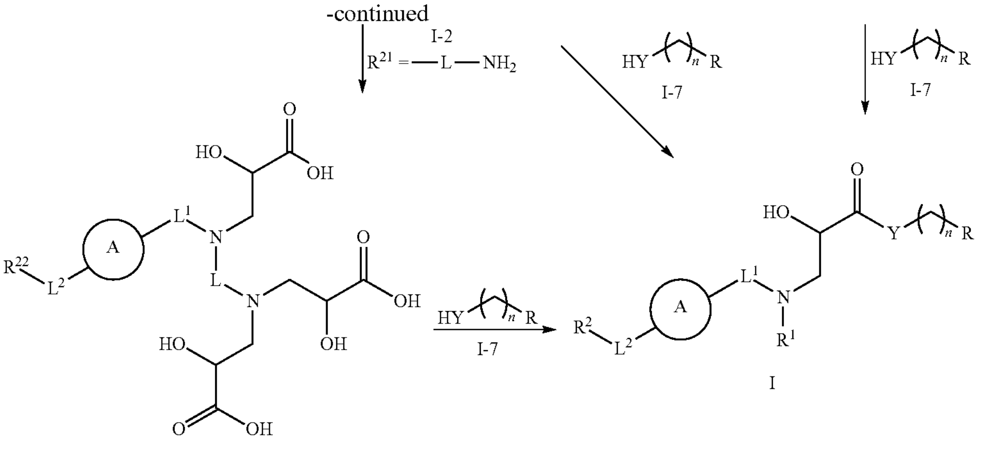

I-6

Appropriate starting materials and reagents can be purchased or prepared by methods known to one of skill in the art. For any compound shown in Scheme I, it should be understood that various derivatives can be provided by functional group interconversion at any step. In some embodiments, the various substituents of Formula I, I-1, I-2, I-3, I-5, I-6, and I-7 are as defined herein. However, derivatization of compounds I, I-1, I-2, I-3, I-5, I-6, and I-7 prior to reacting in any step, and/or further derivatization of the resulting reaction product, provides various compounds of Formula I, or a pharmaceutically acceptable salt, stereoisomer, or mixture of stereoisomers thereof. Appropriate starting materials and reagents can be purchased or prepared by methods known to one of skill in the art. Upon each reaction completion, each of the intermediate or final compounds can be recovered, and optionally purified, by conventional techniques such as neutralization, extraction, precipitation, chromatography, filtration, and the like. Other modifications to arrive at compounds of this disclosure are within the skill of the art.

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like. It should be appreciated that various isomers of Formula I can be separated as well.

General Synthesis

Typical embodiments of compounds described herein may be synthesized using the general reaction schemes described herein. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Examples

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

DCC N,N-dicyclohexylcarbodiimide

DCM dichloromethane

DMAP 4-dimethylaminopyridine

DMF N,N-dimethylformamide

HCTU 2-(6-chloro-TH-benzotriazole-1-yl)-1,1,3,3-tetramethylaminium hexafluorophosphate HRMS high resolution mass spectrometry NMM N-methylmorpholine 1. Preparation of Ionizable Lipids Scheme 1. Synthesis of ionizable lipids

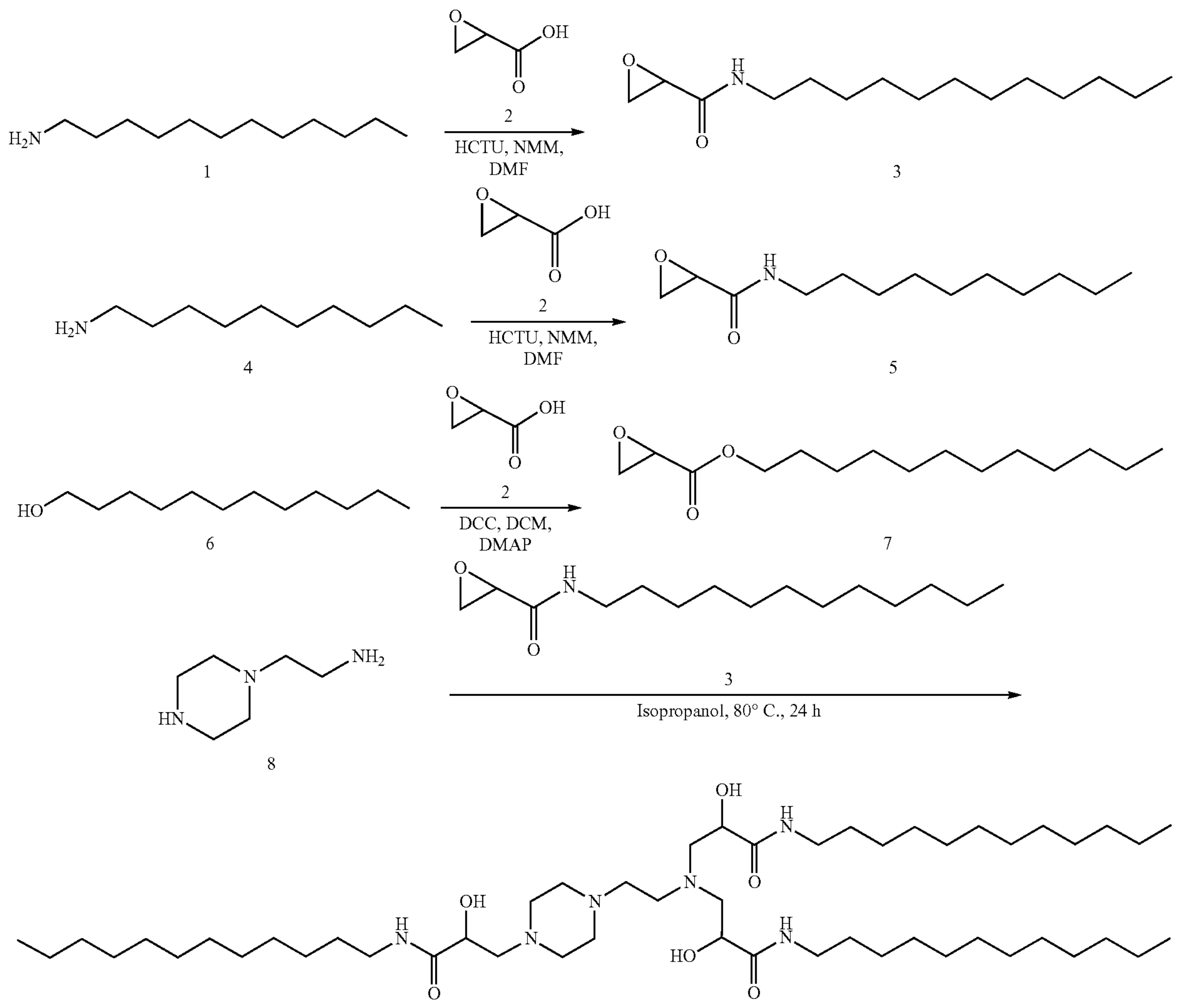

Scheme 2. Synthesis of Epoxypropionamide 3

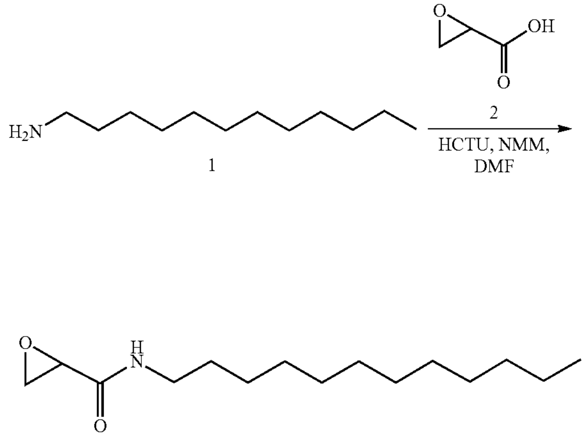

HCTU (6.83 g, 16.5 mmol, 1.1 eq.) was added in portions to a mixed solution of dodecylamine (2.78 g, 15.0 mmol, 1.0 eq.), epoxypropionic acid (1.32 g, 15.0 mmol, 1.0 eq) and NMM (1.82 mL, 15.0 mmol 1.0 eq.) in 60 mL DMF solution and stirred overnight. The reaction system was diluted using 150 mL ethyl acetate, and the resulting solution was washed with saturated sodium chloride solution (50 mL*3). The organic phase was dried with anhydrous sodium sulfate, filtered, the solvent was removed under reduced pressure and the residue was purified by silica gel column chromatography (eluent: petroleum ether:ethyl acetate=5:1) to give epoxypropionamide 3 (3.1 g, 80.9%) as a pale yellow powder. $^1$H NMR (400 MHz, Chloroform-d) δ 6.15 (s, 1H), 3.40 (dd, J=4.8, 2.8 Hz, 1H), 3.20 (dp, J=16.8, 6.4 Hz, 2H), 2.95 (t, J=5.2 Hz, 1H), 2.71 (dd, J=5.6, 2.8 Hz, 1H), 1.45 (p, J=6.8 Hz, 2H), 1.34-1.16 (m, 18H), 0.85 (t, J=6.8 Hz, 3H); HRMS (ESI, m/z) $[M+H]^+$ calculated for C15H30NO2: 256.22711; found: 256.22806.

Scheme 3. Synthesis of epoxypropionate 5

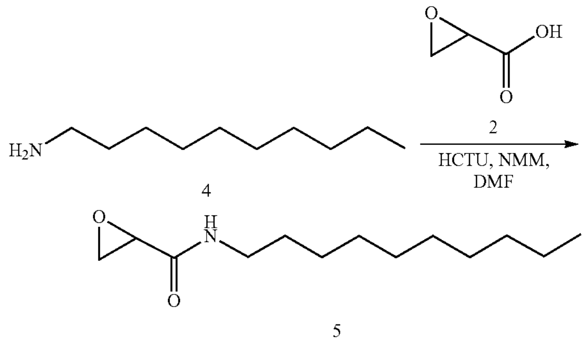

HCTU (9.10 g, 22.0 mmol. 0.1 eq.) was added in portions to a mixed solution of decylamine (3.46 g, 22.0 mmol, 1.1 eq), epoxypropionic acid (1.76 g, 20.0 mmol, 1.0 eq.) and NMM (2.42 mL, 22.0 mmol, 1.1 eq.) in 60 mL DMF solution and was stirred overnight. The reaction system was diluted using 150 mL ethyl acetate, and the resulting solution was washed with saturated sodium chloride solution (50 mL*3). The organic phase was dried using anhydrous sodium sulfate, filtered, the solvent was removed under reduced pressure and the residue was purified by silica gel column chromatography (eluent: petroleum ether; ethyl acetate=5:1) to give epoxypropionate 5 (3.2 g, 70.2%) as a pale yellow powder. $^1$H NMR (400 MHz, Chloroform-d) δ 6.10 (s, 1H), 3.43 (dd, J=4.8, 2.8 Hz, 1H), 3.23 (dp, J=19.6, 6.4 Hz, 2H), 2.98 (t, J=5.2 Hz, 1H), 2.73 (dd, J=5.6, 2.4 Hz, 1H), 1.47 (p, J=6.8 Hz, 2H), 1.33-1.19 (m, 14H), 0.87 (t, J=6.8 Hz, 3H); HRMS (ESI, m/z) $[M+H]^+$ calcd for C13H26NO2$^+$: 228.19581; found: 228.19937.

Scheme 4. Synthesis of epoxypropionate 7

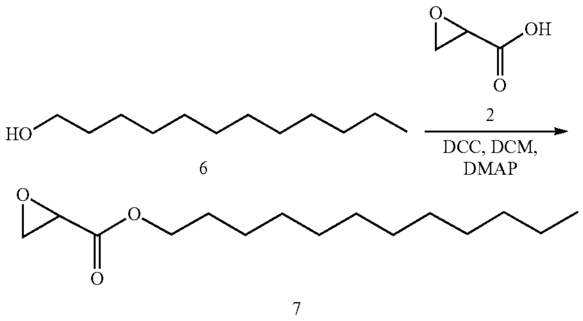

Under ice bath conditions, DCC (4.47 g, 22.0 mmol, 1.1 eq.) was added to the mixed solution of dodecanol (4.10 g, 22.0 mmol, 1.0 eq.), epoxypropionic acid (1.76 g, 20.0 mmol, 1.0 eq.) and DMAP (244.4 mg, 2.0 mmol, 0.1 eq.) in 60 mL DCM. The resulting mixture was continued stirring in the ice bath for half an hour and then moved to room temperature and stirred overnight. The reaction solution was quenched with 100 mL of saturated ammonium chloride and extracted with dichloromethane (50 mL*3). The organic phases were combined and dried using anhydrous sodium sulfate, filtered, the solvent was removed under reduced pressure and the residue was purified by silica gel column chromatography (eluent: petroleum ether:ethyl acetate=20:1) to give epoxypropionate 7 (3.0 g, 58.6%) as a pale yellow powder. $^1$H NMR (400 MHz, Chloroform-d) δ 4.16 (qt, J=10.8, 6.8 Hz, 2H), 3.41 (dd, J=4.0, 2.4 Hz, 1H), 2.93 (qd, J=6.4, 3.2 Hz, 2H), 1-64 (p, J=6.8 Hz, 2H), 1.34-1.17 (m, 18H), 0.86 (t, J=6.8 Hz, 3H); HRMS (ESI, m/z) $[M+H]^+$ calcd for C15H29O3$^+$: 257.21112; found: 257.21190.

Example Procedure 1: Exemplary Synthesis of Lipid Compound L0181

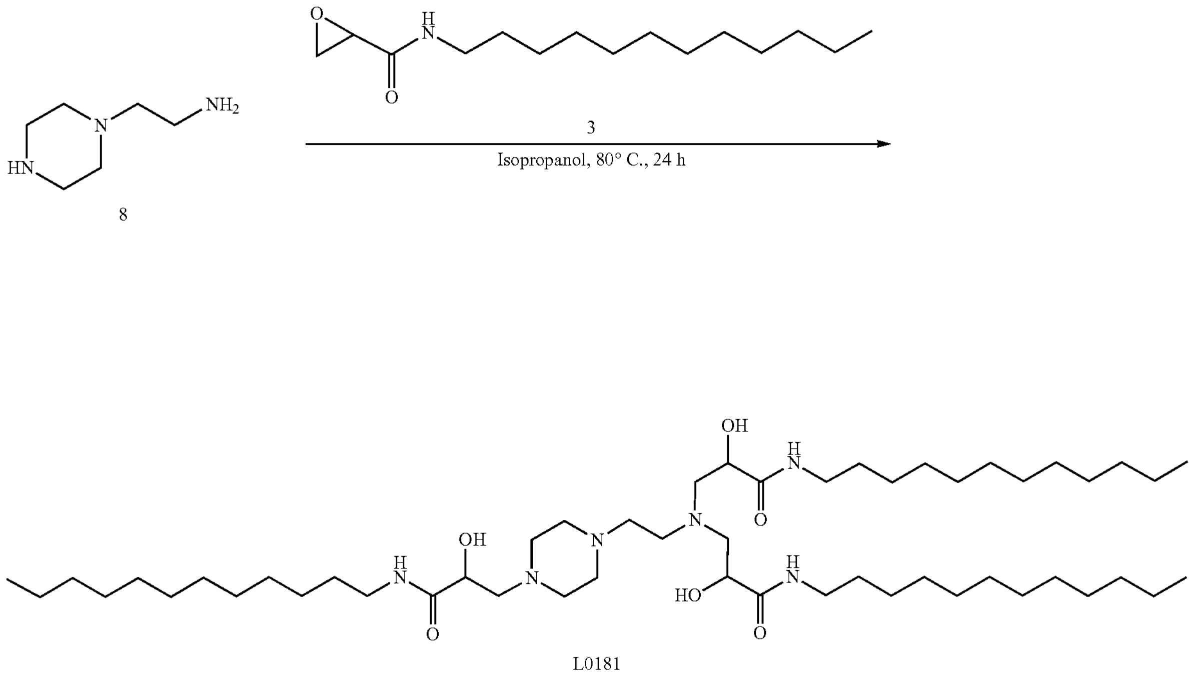

L0181

The lipids are obtained via the epoxy ring-opening reaction between amines and epoxypropionate or propionamide epoxy. The common reaction protocol for the epoxy ring-opening reaction between amines and epoxypropionate/amides is to dissolve 0.1 mmol amine in 2.0 mL of isopropanol, and add 0.1*(2a+b)*1.3 mmol epoxypropionate/amide substrate (where a is the number of primary amines in the amine molecule and b is the number of secondary amines in the amine molecule). The solution was heated up to 80° C. and stirred for 24 h. The isopropanol was removed by concentration under reduced pressure, and the residue DCM/Ultra, was used as eluent and purified by silica gel column chromatography to obtain the target product.

The following compounds of Table 1A and 1B were prepared according to the procedures and schemes shown above using the appropriate starting material. Characterization data for the compounds is provided below.

TABLE 1C

Yield and Characterization of Compounds

| Compound No. | Yield and Characterization Data |
|---|---|
| L0180 | Yield: 100%. $^1$H NMR (400 MHZ, Chloroform-d) δ 7.11 (t, J = 6.0 Hz, 1H), 6.98 (t, J = 6.0 Hz, 2H), 4.21-3.89 (m, 4H), 3.32-3.12 (m, 6H), 3.07 (dd, J = 14.0, 2.8 Hz, 2H), 2.91-2.32 (m, 17H), 1.48 (q, J = 7.2 Hz, 6H), 1.33-1.19 (m, 42H), 0.85 (t, J = 6.8 Hz, 9H); HRMS (ESI, m/z): [M + H]$^+$ calcd. For $C_{45}H_{91}N_6O_6$, 811.69946; found 811.69934. |
| L0181 | Yield: 74.8%. $^1$H NMR (400 MHZ, Chloroform-d) δ 7.11 (t, J = 6.0 Hz, 1H), 6.97 (t, J = 6.0 Hz, 2H), 4.01 (ddd, J = 12.4, 8.0, 4.4 Hz, 3H), 3.33-3.14 (m, 6H), 3.09 (dd, J = 14.0, 3.2 Hz, 2H), 2.89-2.34 (m, 16H), 1.59-1.42 (m, 7H), 1.42-1.15 (m, 54H), 0.86 (t, J = 6.8 Hz, 9H); HRMS (ESI, m/z) [M + H]$^+$ calcd for $C_{51}H_{103}N_6O_6^+$: 895.79336; found: 895.79380. |
| L0182 | Yield: 31.9%. $^1$H NMR (400 MHZ, Chloroform-d) δ 4.33-3.99 (m, 9H), 3.02 (dd, J = 14.0, 3.2 Hz, 2H), 2.96-2.27 (m, 16H), 1.63 (p, J = 6.8 Hz, 6H), 1.36-1.22 (m, 42H), 0.87 (t, J = 6.8 Hz, 9H); HRMS (ESI, m/z): [M + H]$^+$ calcd. For $C_{45}H_{88}N_3O_9$, 814.65151; found 814.65159. |
| L0183 | Yield: 56.8%. $^1$H NMR (400 MHZ, Chloroform-d) δ 4.32-3.98 (m, 9H), 3.01 (dd, J = 14.0, 3.2 Hz, 2H), 2.93-2.29 (m, 16H), 1.63 (p, J = 6.8 Hz, 6H), 1.35-1.20 (m, 54H), 0.86 (t, J = 6.8 Hz, 9H); HRMS (ESI, m/z): [M + H]$^+$ calcd. For $C_{51}H_{100}N_3O_9$, 898.74541; found 898.74576. |
| L0184 | Yield: 54.3%. $^1$H NMR (400 MHZ, Chloroform-d) δ 4.63 (s, 6H), 4.28-4.02 (m, 9H), 3.49 (t, J = 6.8 Hz, 12H), 2.99 (dd, J = 14.0, 3.2 Hz, 2H), 2.94-2.41 (m, 15H), 2.39-2.30 (m, 1H), 1.76-1.42 (m, 18H), 1.41-1.24 (m, 30H), 0.86 (t, J = 6.8 Hz, 9H). HRMS (ESI, m/z): [M + H]$^+$ calcd. For $C_{54}H_{106}N_3O_{15}$, 1036.76185; found 1036.76235. |
| L0185 | Yield: 24.1%. $^1$H NMR (400 MHZ, Chloroform-d) δ 4.52-4.33 (m, 6H), 4.32-4.15 (m, 3H), 3.09-3.01 (m, 2H), 2.96-2.78 (m, 10H), 2.78-2.66 (m, 10H), 2.66-2.34 (m, 8H), 1.66 (p, J = 7.2 Hz, 6H), 1.43-1.24 (m, 42H), 0.87 (t, J = 6.8 Hz, 9H). HRMS (ESI, m/z): [M + H]$^+$ calcd. For $C_{51}H_{100}N_3O_9S_6$, 1090.57783; found 1090.57566. |
| L0186 | Yield: 47.3%. $^1$H NMR (400 MHZ, Chloroform-d) 8 4.28-4.12 (m, 9H), 4.09 (td, J = 6.0, 2.4 Hz, 6H), 3.03 (dd, J = 14.0, 3.2 Hz, 2H), 2.96-2.52 (m, 15H), 2.36-2.25 (m, 4H), 1.77-1.66 (m, 12H), 1.62-1.53 (m, 6H), 1.47-1.39 (m, 6H), 1.33-1.20 (m, 48H), 0.87 (t, J = 6.8 Hz, 18H). HRMS (ESI, m/z): [M + H]$^+$ calcd. For $C_{69}H_{130}N_3O_{15}$, 1240.94965; found: 1240.95611. |
| L0187 | Yield: 26.8%. $^1$H NMR (400 MHZ, Chloroform-d) δ 4.29-4.08 (m, 9H), 4.05 (t, J = 6.8 Hz, 6H), 3.02 (dd, J = 14.0, 3.2 Hz, 2H), 2.96-2.43 (m, 15H), 2.38-2.25 (m, 4H), 1.71-1.51 (m, 18H), 1.48-1.33 (m, 18H), 1.33-1.16 (m, 48H), 0.86 (t, J = 6.8 Hz, 18H). HRMS (ESI, m/z): [M + H]$^+$ calcd. For $C_{75}H_{142}N_3O_{15}$, 1325.04355; found: 1325.05203. |
| L0188 | Yield: 54.2%. $^1$H NMR (400 MHZ, Chloroform-d) δ 4.32-4.08 (m, 9H), 4.06 (td, J = 6.8, 2.0 Hz, 6H), 3.03 (dd, J = 14.0, 3.2 Hz, 2H), 2.96-2.46 (m, 15H), 2.36-2.23 (m, 4H), 1.70-1.53 (m, 18H), 1.48-1.34 (m, 18H), 1.32-1.19 (m, 60H), 0.87 (t, J = 6.8 Hz, 18H). HRMS (ESI, m/z): [M + H]$^+$ calcd. For $C_{81}H_{154}N_3O_{15}$, 1409.13745; found: 1409.14525. |
| L0189 | Yield: 37.0%. $^1$H NMR (400 MHZ, Chloroform-d) δ 6.89 (t, J = 6.0 Hz, 4H), 4.12 (dd, J = 8.0, 3.6 Hz, 4H), 3.38-3.10 (m, 8H), 2.90 (dd, J = 13.6, 3.6 Hz, 4H), 2.77-2.32 (m, 20H), 1.68-1.59 (m, 4H), 1.55-1.45 (m, 8H), 1.39-1.17 (m, 56H), 0.88 (t, J = 6.8 Hz, 12H); HRMS (ESI, m/z) [M + H]$^+$ calcd for $C_{62}H_{125}N_8O_8^+$: 1109.96149; found: 1109.96256. |
| L0190 | Yield: 38.5%. $^1$H NMR (400 MHZ, Chloroform-d) δ 6.87 (t, J = 6.0 Hz, 4H), 4.11 (dd, J = 8.4, 3.6 Hz, 4H), 3.33-3.14 (m, 8H), 2.89 (dd, J = 13.6, 3.6 Hz, 4H), 2.81-2.29 (m, 20H), 1.69-1.57 (m, 4H), 1.50 (p, J = 7.2 Hz, 8H), 1.36-1.18 (m, 72H), 0.87 (t, J = 6.8 Hz, 12H); HRMS (ESI, m/z) [M + H]$^+$ calcd for $C_{70}H_{141}N_8O_8^+$: 1222.08669; found: 1222.09028. |
| L0191 | Yield: 23.7%. $^1$H NMR (400 MHZ, Chloroform-d) δ 4.27-3.99 (m, 12H), 3.07-2.60 (m, 16H), 2.59-2.29 (m, 6H), 2.28-2.11 (m, 2H), 1.61 (q, J = 7.5, 6.6 Hz, 12H), 1.34-1.18 (m, 72H), 0.86 (t, J = 6.8 Hz, 12H); HRMS (ESI, m/z) [M + H]$^+$ calcd for $C_{70}H_{137}N_4O_{12}^+$: 1226.02275; found: 1226.02440. |
| L0191-Control | Yield: 79.2%. $^1$H NMR (400 MHZ, Chloroform-d) δ 4.04 (t, J = 6.8 Hz, 8H), 2.75 (t, J = 7.2 Hz, 8H), 2.71-2.05 (m, 24H), 1.66-1.55 (m, 12H), 1.34-1.24 (m, 72H), 0.88 (t, J = 6.8 Hz, 12H). HRMS (ESI, m/z): [M + H]$^+$ calcd. For $C_{70}H_{137}N_4O_8$, 1162.04309; found: 1162.04745. |
| L0192 | Yield: 43.7%. $^1$H NMR (400 MHZ, Chloroform-d) δ 4.63 (s, 8H), 4.27-4.01 (m, 12H), 3.50 (t, J = 6.8 Hz, 16H), 3.00-2.34 (m, 22H), 2.29-2.10 (m, 3H), 2.07-1.93 (m, 1H), 1.77-1.42 (m, 28H), 1.41-1.25 (m, 40H), 0.87 (t, J = 6.8 Hz, 12H). HRMS (ESI, m/z): [M + H]$^+$ calcd. For $C_{74}H_{145}N_4O_{20}$, 1410.04467; found 1410.04455. |

TABLE 1C-continued

Yield and Characterization of Compounds

| Compound No. | Yield and Characterization Data |
| --- | --- |
| L0193 | Yield: 11.2%. $^{1}$H NMR (400 MHz, Chloroform-d) δ 8.05 (t, J = 5.6 Hz, 2H), 7.14 (t, J = 6.0 Hz, 4H), 4.10 (dd, J = 8.0, 4.0 Hz, 4H), 3.40-3.14 (m, 14H), 3.05 (dd, J = 13.6, 4.0 Hz, 4H), 2.78 (dd, J = 13.6, 8.0 Hz, 4H), 2.61-2.43 (m, 14H), 1.77-1.65 (m, 4H), 1.49 (p, J = 7.2 Hz, 8H), 1.34-1.23 (m, 72H), 0.87 (t, J = 6.8 Hz, 12H). HRMS (ESI, m/z): $[M + H]^+$ calcd. For $C_{74}H_{146}N_{10}O_{10}$, 1336.12962; found 1336.12023. |
| L0194 | Yield: 15.4%. $^{1}$H NMR (400 MHZ, Chloroform-d) δ 7.70 (t, J = 5.2 Hz, 2H), 7.03 (t, J = 6.0 Hz, 4H), 4.07 (dd, J = 8.4, 3.6 Hz, 4H), 3.42-3.09 (m, 12H), 3.00-2.88 (m, 6H), 2.83-2.66 (m, 6H), 2.61-2.23 (m, 16H), 1.74-1.61 (m, 4H), 1.57-1.41 (m, 8H), 1.36-1.19 (m, 72H), 0.86 (t, J = 6.8 Hz, 12H). HRMS (ESI, m/z): $[M+2H]^{2+}$ calcd. For $C_{76}H_{150}N_{10}O_{10}$, 682.58410; found 682.59124. |
| L0195 | Yield: 4.3%. $^{1}$H NMR (400 MHZ, Chloroform-d) δ 7.65-7.48 (m, 2H), 7.18-6.94 (m, 4H), 4.07 (dd, J = 8.8, 3.6 Hz, 4H), 3.44-3.08 (m, 12H), 2.88 (dd, J = 13.6, 3.6 Hz, 4H), 2.74-2.45 (m, 18H), 2.32-2.13 (m, 6H), 1.92-1.83 (m, 2H), 1.74-1.62 (m, 6H), 1.49 (p, J = 7.2 Hz, 8H), 1.36-1.22 (m, 72H), 0.87 (t, J = 6.8 Hz, 12H). HRMS (ESI, m/z): $[M + H]^+$ calcd. For $C_{78}H_{154}N_{10}O_{10}$, 1392.19222; found 1392.21626. |
| L0196 | Yield: 34.4%. $^{1}$H NMR (400 MHZ, Chloroform-d) δ 4.31-4.10 (m, 12H), 4.10-4.04 (m, 8H), 3.09-2.37 (m, 22H), 2.36-2.22 (m, 6H), 1.77-1.64 (m, 16H), 1.64-1.49 (m, 12H), 1.46-1.37 (m, 8H), 1.31-1.17 (m, 64H), 0.85 (t, J = 6.8 Hz, 24H). HRMS (ESI, m/z): $[M + H]^+$ calcd. For $C_{94}H_{177}N_4O_{20}$, 1683.29842; found: 1683.30720. |
| L0197 | Yield: 39.6%. $^{1}$H NMR (400 MHz, Chloroform-d) δ 4.29-4.14 (m, 8H), 4.14-4.08 (m, 4H), 4.05 (t, J = 6.7 Hz, 8H), 3.10-2.34 (m, 22H), 2.34-2.21 (m, 6H), 1.70-1.52 (m, 28H), 1.47-1.33 (m, 24H), 1.31-1.18 (m, 80H), 0.86 (t, J = 6.6 Hz, 24H). HRMS (ESI, m/z): $[M + H]^+$ calcd. For $C_{110}H_{209}N_4O_{20}$, 1907.54883; found: 1907.54969. |
| L0198 | Yield: 95.6%. $^{1}$H NMR (400 MHZ, Chloroform-d) δ 7.12 (dt, J = 16.8, 6.0 Hz, 3H), 6.97 (t, J = 6.0 Hz, 2H), 4.71 (s, 2H), 4.17-3.95 (m, 5H), 3.34-3.13 (m, 10H), 3.11-2.81 (m, 8H), 2.78-2.35 (m, 22H), 1.57-1.42 (m, 10H), 1.39-1.12 (m, 72H), 0.86 (t, J = 6.8 Hz, 15H). HRMS (ESI, m/z): $[M + H]^+$ calcd. For $C_{75}H_{151}N_{10}O_{10}$, 1352.16092; found 1352.15853. |
| L0199 | Yield: 39.2%. $^{1}$H NMR (400 MHZ, Chloroform-d) δ 4.31-4.00 (m, 15H), 3.05-2.35 (m, 30H), 1.63 (p, J = 6.8 Hz, 10H), 1.42-1.13 (m, 90H), 0.86 (t, J = 6.8 Hz, 15H). HRMS (ESI, m/z): $[M + H]^+$ calcd. For $C_{85}H_{166}N_5O_{15}$, 1497.23749; found 1497.23599. |
| L0199-Control | Yield: 39.4%. $^{1}$H NMR (400 MHZ, Chloroform-d) δ 4.04 (t, J = 6.8 Hz, 10H), 2.78 (q, J = 7.2 Hz, 10H), 2.65-2.39 (m, 24H), 1.61 (p, J = 6.8 Hz, 10H), 1.37-1.20 (m, 90H), 0.87 (t, J = 6.8 Hz, 15H). HRMS (ESI, m/z): $[M + H]^+$ calcd. For $C_{85}H_{166}N_5O_{10}$, 1417.26292; found: 1417.26784. |
| L0200 | Yield: 33.6%. $^{1}$H NMR (400 MHZ, Chloroform-d) δ 4.65 (s, 10H), 4.30-4.03 (m, 15H), 3.61-3.41 (m, 20H), 3.09-2.39 (m, 30H), 1.72-1.52 (m, 30H), 1.43-1.27 (m, 50H), 0.88 (t, J = 6.8 Hz, 15H). HRMS (ESI, m/z): $[M + 2H]^{2+}$ caled. For $C_{90}H_{177}N_5O_{25}$, 864.13609; found 864.13697. |
| L0201 | Yield: 16.0%. $^{1}$H NMR (400 MHZ, Chloroform-d) δ 5.54-5.41 (m, 5H), 5.40-5.31 (m, 5H), 4.65 (s, 10H), 4.27-4.04 (m, 15H), 3.52 (td, J = 6.8, 3.2 Hz, 20H), 3.07-2.46 (m, 30H), 2.32 (q, J = 7.2 Hz, 10H), 2.05 (p, J = 7.6 Hz, 10H), 1.70-1.54 (m, 20H), 1.43-1.33 (m, 20H), 0.96 (t, J = 7.6 Hz, 15H). HRMS (ESI, m/z): $[M + 2H]^{2+}$ calcd. For $C_{90}H_{167}N_5O_{25}$, 859.09696; found 859.09844. |
| L0202 | Yield: 16.0%. $^{1}$H NMR (400 MHZ, Chloroform-d) δ 5.54-5.42 (m, 5H), 5.41-5.31 (m, 5H), 4.65 (s, 10H), 4.32-4.05 (m, 15H), 3.53 (dt, J = 10.4, 6.8 Hz, 20H), 3.06-2.43 (m, 30H), 2.32 (q, J = 7.2 Hz, 10H), 2.09-1.98 (m, 10H), 1.81-1.69 (m, 10H), 1.69-1.59 (m, 10H), 1.37-1.29 (m, 20H), 0.88 (t, J = 6.8 Hz, 15H). HRMS (ESI, m/z): $[M + 2H]^{2+}$ calcd. For $C_{90}H_{167}N_5O_{25}$, 859.09696; found 859.09743. |
| L0203 | Yield: 28.2%. $^{1}$H NMR (400 MHZ, Chloroform-d) δ 4.31-4.07 (m, 15H), 4.05 (t, J = 6.8 Hz, 10H), 3.10-2.38 (m, 30H), 2.33-2.25 (m, 5H), 1.74-1.49 (m, 30H), 1.46-1.34 (m, 30H), 1.32-1.22 (m, 80H), 0.86 (t, J = 6.8 Hz, 30H). HRMS (ESI, m/z): $[M + H]^+$ calcd. For $C_{125}H_{236}N_5O_{25}$, 2208.73775; found 2208.73582. |
| L0207 | Yield: 51.6%. $^{1}$H NMR (400 MHz, Chloroform-d) δ 7.25-7.17 (m, 4H), 4.22-3.98 (m, 12H), 3.88 (d, J = 13.6 Hz, 2H), 3.64 (d, J = 13.6 Hz, 2H), 2.97 (dd, J = 14.0, 3.6 Hz, 4H), 2.88 (dd, J = 13.6, 7.6 Hz, 4H), 1.60 (p, J = 6.8 Hz, 8H), 1.33-1.20 (m, 72H), 0.87 (t, J = 6.8 Hz, 12H). HRMS (ESI, m/z): $[M + H]^+$ calcd. For $C_{68}H_{125}N_2O_{12}$, 1161.92270; found: 1161.92963. |
| L0208 | Yield: 77.6%. $^{1}$H NMR (400 MHz, Chloroform-d) δ 7.23-7.15 (m, 4H), 7.13-7.00 (m, 4H), 3.92 (dd, J = 7.6, 4.0 Hz, 4H), 3.73 (t, J = 13.2 Hz, 2H), 3.61 (d, J = 13.2 Hz, 2H), 3.26-3.06 (m, 8H), 2.90 (dd, J = 13.6, 4.4 Hz, 4H), 2.81-2.66 (m, 4H), 1.52-1.39 (m, 8H), 1.35-1.09 (m, 72H), 0.86 (t, J = 6.8 Hz, 12H). HRMS (ESI, m/z): $[M + 2H]^{2+}$ calcd. For $C_{68}H_{130}N_6O_8$, 579.49696; found: 579.50087. |
| L0209 | Yield: 34.8%. $^{1}$H NMR (400 MHz, Chloroform-d) δ 4.24-4.04 (m, 12H), 3.13-2.06 (m, 24H), 1.71-1.51 (m, 12H), 1.37-1.20 (m, 56H), 0.92-0.82 (m, 12H). HRMS (ESI, m/z): $[M + H]^+$ calcd. For $C_{62}H_{121}N_4O_{12}$, 1113.89755; found: 1113.90384. |
| L0210 | Yield: 29.5%. $^{1}$H NMR (400 MHz, Chloroform-d) δ 4.28-4.01 (m, 15H), 3.11-2.28 (m, 30H), 1.72-1.56 (m, 10H), 1.37-1.17 (m, 70H), 0.87 (t, J = 6.8 Hz, 15H). HRMS (ESI, m/z): $[M + H]^+$ calcd. For $C_{75}H_{146}N_5O_{15}$, 1357.08099; found: 1357.09089. |
| L0211 | Yield: 51.9%. $^{1}$H NMR (400 MHz, Chloroform-d) δ 7.25-7.18 (m, 4H), 4.25-3.99 (m, 12H), 3.89 (d, J = 13.6 Hz, 2H), 3.65 (d, J = 13.6 Hz, 2H), 2.97 (dd, J = 14.0, 3.6 Hz, 4H), 2.88 (dd, J = 13.6, 7.6 Hz, 4H), 1.61 (p, J = 6.8 Hz, 8H), 1.35-1.21 (m, 56H), 0.87 (t, J = 6.8 Hz, 12H). HRMS (ESI, m/z): $[M + H]^+$ calcd. For $C_{60}H_{109}N_2O_{12}$, 1049.79750; found: 1049.80274. |

TABLE 1C-continued

| Compound No. | Yield and Characterization Data |
|---|---|
| Yield and Characterization of Compounds | |
| L0212 | Yield: 14.4%. $^1$H NMR (400 MHZ, Chloroform-d) δ 4.38-3.99 (m, 9H), 3.63 (t, J = 6.6 Hz, 1H), 3.03-2.69 (m, 7H), 1.87-1.74 (m, 2H), 1.72-1.47 (m, 10H), 1.46-1.38 (m, 2H), 1.26 (d, J = 6.8 Hz, 54H), 0.87 (t, J = 6.8 Hz, 9H). HRMS (ESI, m/z): [M + H]$^+$ calcd. For $C_{66}H_{127}N_2O_{12}$, 883.73451, found: 883.73421. |
| L0213 | Yield: 73.7%. $^1$H NMR (400 MHZ, Chloroform-d) δ 7.15-6.98 (m, 4H), 4.11 (dd, J = 8.8, 3.6 Hz, 4H), 3.29-3.13 (m, 8H), 3.01 (dd, J = 14.4, 3.2 Hz, 4H), 2.81-2.54 (m, 6H), 2.08-1.79 (m, 4H), 1.48 (p, J = 6.8 Hz, 8H), 1.42-1.34 (m, 4H), 1.34-1.06 (m, 72H), 0.86 (t, J = 6.8 Hz, 12H). HRMS (ESI, m/z): [M + H]$^+$ calcd. For $C_{66}H_{131}NO_8$, 1136.00229; found: 1136.00720. |
| L0214 | Yield: 93.5%. $^1$H NMR (400 MHZ, Chloroform-d) δ 7.13-6.98 (m, 4H), 4.01 (dd, J = 8.0, 4.0 Hz, 4H), 3.30-3.07 (m, 8H), 3.00-2.80 (m, 4H), 2.60 (dd, J = 13.8, 7.9 Hz, 4H), 2.50-2.38 (m, 2H), 1.91-1.62 (m, 4H), 1.56-1.39 (m, 8H), 1.37-1.06 (m, 76H), 0.86 (t, J = 6.8 Hz, 12H). HRMS (ESI, m/z): [M + H]$^+$ calcd. For $C_{66}H_{131}N_6O_8$, 1136.00229; found: 1136.00786. |
| L0215 | Yield: 76.9%. $^1$H NMR (400 MHZ, Chloroform-d) δ 7.24-7.15 (m, 4H), 7.03 (t, J = 6.0 Hz, 4H), 3.91 (dd, J = 8.0, 4.0 Hz, 4H), 3.74 (t, J = 12.0 Hz, 2H), 3.63 (d, J = 13.2 Hz, 2H), 3.17 (q, J = 6.4 Hz, 8H), 2.92 (dd, J = 13.6, 4.0 Hz, 4H), 2.77 (dd, J = 13.6, 8.0 Hz, 4H), 1.46 (p, J = 6.8 Hz, 8H), 1.37-1.14 (m, 56H), 0.86 (t, J = 6.8 Hz, 12H). HRMS (ESI, m/z): [M + H]$^+$ calcd. For $C_{60}H_{113}N_6O_8$, 1045.86144; found: 1045.86287. |
| L0216 | Yield: 75.6%. $^1$H NMR (400 MHZ, Chloroform-d) 8 7.02 (t, J = 6.0 Hz, 4H), 4.13 (dd, J = 8.8, 3.6 Hz, 4H), 3.29-3.14 (m, 8H), 3.04 (dd, J = 14.4, 3.2 Hz, 4H), 2.81-2.55 (m, 6H), 2.05-1.85 (m, 4H), 1.54-1.34 (m, 12H), 1.34-1.17 (m, 56H), 0.87 (t, J = 6.8 Hz, 12H). HRMS (ESI, m/z): [M + H]$^+$ calcd. For $C_{58}H_{115}N_6O_8$, 1023.87709; found: 1023.87732. |
| L0217 | Yield: 15.9%. $^1$H NMR (400 MHZ, Chloroform-d) δ 7.14 (t, J = 6.0 Hz, 1H), 6.97 (t, J = 6.0 Hz, 2H), 4.14-3.97 (m, 3H), 3.30-3.16 (m, 6H), 3.07-2.89 (m, 4H), 2.87-2.69 (m, 4H), 1.82 (d, J = 12.8 Hz, 2H), 1.67-1.38 (m, 12H), 1.36-1.21 (m, 42H), 0.87 (t, J = 6.8 Hz, 9H). HRMS (ESI, m/z): [M + H]$^+$ calcd. For $C_{45}H_{90}N_5O_6$, 796.68856; found: 796.68955. |
| L0218 | Yield: 73.1%. $^1$H NMR (400 MHZ, Chloroform-d) δ 7.06 (t, J = 6.0 Hz, 4H), 4.01 (dd, J = 8.0, 4.0 Hz, 4H), 3.31-3.09 (m, 8H), 3.06-2.82 (m, 4H), 2.69-2.36 (m, 6H), 1.91-1.63 (m, 4H), 1.48 (p, J = 6.8 Hz, 8H), 1.35-1.06 (m, 60H), 0.86 (t, J = 6.8 Hz, 12H). HRMS (ESI, m/z): [M + H]$^+$ calcd. For $C_{58}H_{115}N_6O_8$, 1023.87709; found: 1023.87633. |
| L0219 | Yield: 30.3%. $^1$H NMR (400 MHZ, Chloroform-d) δ 7.14 (t, J = 6.0 Hz, 1H), 6.91 (t, J = 6.0 Hz, 2H), 4.07-3.90 (m, 3H), 3.30-3.15 (m, 6H), 2.99-2.81 (m, 4H), 2.70-2.59 (m, 2H), 2.57-2.47 (m, 1H), 2.41-2.29 (m, 1H), 2.04-1.92 (m, 2H), 1.85-1.66 (m, 2H), 1.49 (p, J = 7.2 Hz, 6H), 1.34-1.02 (m, 46H), 0.87 (t, J = 6.8 Hz, 9H). HRMS (ESI, m/z): [M + H]$^+$ calcd. For $C_{45}H_{90}N_5O_6$, 796.68856; found: 796.68955. |
| L0220 | Yield: 70.7%. $^1$H NMR (400 MHZ, Chloroform-d) δ 4.73-4.57 (m, 3H), 4.30-4.01 (m, 9H), 3.61-3.49 (m, 6H), 3.43-3.32 (m, 6H), 3.01 (dd, J = 14.0, 3.2 Hz, 2H), 2.93-2.30 (m, 16H), 1.72-1.60 (m, 6H), 1.60-1.45 (m, 12H), 1.41-1.24 (m, 39H), 0.87 (t, J = 6.8 Hz, 9H). HRMS (ESI, m/z): [M + H]$^+$ calcd. For $C_{57}H_{112}N_3O_{15}$, 1078.80879; found: 1078.80722. |
| L0221 | Yield: 65.2%. $^1$H NMR (400 MHZ, Chloroform-d) δ 5.54-5.39 (m, 3H), 5.37-5.25 (m, 3H), 4.63 (s, 6H), 4.25-4.04 (m, 9H), 3.50 (td, J = 6.8, 2.8 Hz, 12H), 3.00 (ddd, J = 14.0, 7.6, 3.6 Hz, 2H), 2.91-2.40 (m, 16H), 2.34-2.27 (m, 6H), 2.03 (pd, J = 7.6, 1.4 Hz, 6H), 1.68-1.51 (m, 12H), 1.42-1.29 (m, 12H), 0.94 (t, J = 7.6 Hz, 9H). HRMS (ESI, m/z): [M + H]$^+$ calcd. For $C_{54}H_{100}N_3O_{15}$, 1030.71489; found: 1030.71420. |
| L0222 | Yield: 60.2%. $^1$H NMR (400 MHZ, Chloroform-d) δ 5.54-5.39 (m, 3H), 5.39-5.27 (m, 3H), 4.64 (s, 6H), 4.33-4.02 (m, 9H), 3.51 (dt, J = 9.6, 6.8 Hz, 12H), 3.00 (dd, J = 14.0, 3.2 Hz, 2H), 2.95-2.38 (m, 16H), 2.31 (q, J = 7.2 Hz, 6H), 2.02 (q, J = 6.8 Hz, 6H), 1.79-1.67 (m, 6H), 1.67-1.57 (m, 6H), 1.36-1.24 (m, 12H), 0.92-0.81 (m, 9H). HRMS (ESI, m/z): [M + H]$^+$ calcd. For $C_{54}H_{100}N_3O_{15}$, 1030.71489; found: 1030.71424. |
| L0223 | Yield: 63.4%. $^1$H NMR (400 MHZ, Chloroform-d) δ 7.10 (t, J = 6.0 Hz, 1H), 6.97 (t, J = 6.0 Hz, 2H), 5.59-5.02 (m, 6H), 4.09-3.95 (m, 3H), 3.33-3.12 (m, 6H), 3.08 (dd, J = 14.0, 3.2 Hz, 2H), 2.95-2.30 (m, 16H), 2.13-1.78 (m, 12H), 1.57-1.38 (m, 6H), 1.37-1.16 (m, 66H), 0.85 (t, J = 6.8 Hz, 9H). HRMS (ESI, m/z): [M + H]$^+$ caled. For $C_{69}H_{133}N_6O_6$, 1142.02811; found: 1142.02720. |
| L0224 | Yield: 49.0%. $^1$H NMR (400 MHZ, Chloroform-d) δ 4.63 (q, J = 5.2 Hz, 4H), 4.24-4.01 (m, 12H), 3.58-3.47 (m, 8H), 3.37 (dt, J = 9.2, 6.8 Hz, 8H), 3.00-2.26 (m, 22H), 2.25-2.13 (m, 2H), 1.73-1.44 (m, 28H), 1.42-1.22 (m, 52H), 0.86 (t, J = 6.8 Hz, 12H). HRMS (ESI, m/z): [M + H]$^+$ calcd. For $C_{78}H_{153}N_4O_{20}$, 1466.10727; found: 1466.10311. |
| L0225 | Yield: 42.9%. $^1$H NMR (400 MHZ, Chloroform-d) δ 5.55-5.39 (m, 4H), 5.37-5.23 (m, 4H), 4.64 (s, 8H), 4.22-4.03 (m, 12H), 3.57-3.44 (m, 16H), 2.99-2.37 (m, 22H), 2.31 (qd, J = 7.2, 1.6 Hz, 8H), 2.27-2.11 (m, 2H), 2.04 (pd, J = 7.6, 1.6 Hz, 8H), 1.71-1.50 (m, 20H), 1.42-1.29 (m, 16H), 0.94 (t, J = 7.6 Hz, 12H). HRMS (ESI, m/z): [M + H]$^+$ calcd. For $C_{74}H_{137}N_4O_{20}$, 1401.98207; found: 1401.98188. |
| L0226 | Yield: 13.1%. $^1$H NMR (400 MHZ, Chloroform-d) δ 5.57-5.41 (m, 4H), 5.41-5.30 (m, 4H), 4.65 (s, 8H), 4.27-4.07 (m, 12H), 3.53 (dt, J = 9.6, 6.8 Hz, 16H), 2.99-2.46 (m, 22H), 2.32 (qd, J = 7.0, 1.6 Hz, 8H), 2.26-2.17 (m, 2H), 2.09-1.98 (m, 8H), 1.78-1.68 (m, 8H), 1.67-1.54 (m, 12H), 1.39-1.27 (m, 16H), 0.92-0.85 (m, 12H). HRMS (ESI, m/z): [M + H]$^+$ calcd. For $C_{74}H_{137}N_4O_{20}$, 1401.98207; found: 1401.98042. |

TABLE 1C-continued

| Yield and Characterization of Compounds | |
|---|---|
| Compound No. | Yield and Characterization Data |
| L0227 | Yield: 18.8%. $^{1}$H NMR (400 MHZ, Chloroform-d) δ 4.27-4.14 (m, 8H), 4.14-4.07 (m, 4H), 4.04 (t, J = 6.8 Hz, 8H), 3.02-2.37 (m, 21H), 2.37-2.13 (m, 7H), 1.71-1.49 (m, 28H), 1.47-1.33 (m, 24H), 1.30-1.20 (m, 64H), 0.85 (t, J = 6.8 Hz, 24H). HRMS (ESI, m/z): $[M + H]^+$ calcd. For $C_{102}H_{193}N_4O_{20}$, 1795.42362; found: 1795.43003. |
| L0228 | Yield: 49.9%. $^{1}$H NMR (400 MHZ, Chloroform-d) δ 4.22-4.03 (m, 12H), 3.03-2.26 (m, 21H), 2.27-1.99 (m, 3H), 1.70-1.46 (m, 12H), 1.37-1.13 (m, 88H), 0.85 (t, J = 6.8 Hz, 12H). HRMS (ESI, m/z): $[M + H]^+$ calcd. For $C_{78}H_{153}N_4O_{12}$, 1338.14795; found: 1338.15143. |
| L0229 | Yield: 28.9%. $^{1}$H NMR (400 MHZ, Chloroform-d) δ 6.89 (t, J = 6.0 Hz, 4H), 5.53-5.14 (m, 8H), 4.10 (dd, J = 8.4, 3.6 Hz, 4H), 3.35-3.12 (m, 8H), 2.88 (dd, J = 13.6, 3.6 Hz, 4H), 2.77-2.30 (m, 20H), 2.19-1.80 (m, 14H), 1.67-1.54 (m, 4H), 1.48 (p, J = 7.2 Hz, 8H), 1.39-1.16 (m, 88H), 0.86 (t, J = 6.8 Hz, 12H). HRMS (ESI, m/z): $[M + H]^+$ calcd. For $C_{94}H_{181}N_8O_8$, 1551.40304; found: 1551.40412. |

2. Preparation of the Lipid Nanoparticles Encapsulating Nucleic Acid Drugs 2.1. Lipid Solubilization The lipid nanoparticle formulations contained four lipid components: ionized lipids or cationic lipids, such as compound L0181; phospholipids, such as 1,2-distearoyl-sn-glycero-3-phosphocholine (DSPC) (Aladdin Reagent (Shanghai) Co., Ltd.); Cholesterol (Chol) (Sigma Aldrich (Shanghai) Trading Co., Ltd.); Polyethylene glycol lipids, such as DMG-$PEG_{2000}$ (Beijing JenKlem Technology Co., Ltd.).

Using a LNP encapsulation formulation for compound L0181 as an example, the organic solvent ethanol (Aladdin Reagent (Shanghai) Co., Ltd.) was used to dissolve the four lipids respectively, ultrasonic dispersion treatment was conducted until clarified and transparent, without obvious insoluble or flocculent. A 0.22 m filter head was used for filtration where needed. The four lipid stock solutions were prepared and obtained, respectively: 5 mg/mL DMG-$PEG_{2000}$, 5 mg/mL DSPC, 10 mg/mL Chol, and 10 mg/mL compound L0181.

2.2. Preparation of the Working Solution for the Nucleic Acid Drugs

With the above formulation as an example, 20.71 μL of 1 mg/mL FLuc-mRNA nucleic acid drug stock solution (Hongene Biotech Corporation, Shanghai) was taken from a biosafety cabinet and transferred into a ribozyme-free plastic centrifuge tube, added up to 497.04 μL 50 mM pH=4 citrate-sodium citrate buffer solution, and used a pipette tip to mix the two gently to obtain a FLuc-mRNA nucleic acid drug working solution at a concentration of 0.04 mg/mL and then sucked up all of the solution and transferred it to a KDL syringe with a needle (2 mL in size) for sparse use.

2.3. Preparation of Mixed Lipid Working Solution

With the above formulation as an example, 16.29 μL of 5 mg/mL DMG-$PEG_{2000}$ stock solution, 37.16 μL of 5 mg/mL DSPC stock solution, 31.73 μL of 10 mg/mL Chol stock solution, and 64.88 μL of 10 mg/mL compound L0181 stock solution were taken from clean preparation room into a ribozyme-free plastic centrifuge tube, supplemented with 49.19 μL organic solvent ethanol. Using a pipette tip to gently blow the above mixed lipid solution to obtain a mixed lipid working solution, wherein the concentration of compound L0181 was about 2.79 mM, the total lipid concentration was about 6.98 mM, the molar ratio of the four lipids was DMG-PEG2000:DSPC:Chol:compound L0181=1.71:12.98:45.31:40.00, the mass ratio of total lipids to nucleic acid drugs was about 51.58:1, and the N/P of ionizable lipids and nucleic acids was 10:1. Sucked up all of the mixed lipid working solution and transferred to a KDL syringe with a needle (1 mL in size) for sparse use.

2.4. Formation of Nucleic Acid Lipid Nanoparticle

With the above formulation as an example, the syringes containing the nucleic acid drug working solution and mixed lipid working solution were separately placed in different bayonets of an aqueous phase syringe pump and an organic phase syringe pump (Longer Precision Pump Co., Ltd., Baoding, dLSP-520). The two ends of the enzyme-free treated Y-mixer (tee) were connected to the syringe ports containing the nucleic acid drug working solution and the mixed lipid working solution, respectively. Set the aqueous syringe pump with the perfusion volume to 477.75 μL, the flow rate to 4.5 mL/min and the syringe size of a 2 mL KDL syringe. Set the organic phase syringe pump with the perfusion volume of 159.25 μL, the flow rate of 1.5 mL/min, and the syringe size of a 1 mL KDL syringe. After confirming that the installation and parameter settings of the synthesis device were correct, the syringe pump was started to control the mixing of the nucleic acid drug working solution and the mixed lipid working solution via being introduced into the Y-mixer at a flow rate ratio of 3:1 and through a certain angle. Liposomal nanoparticles encapsulating the nucleic acid drugs were instantaneously produced and collected at the end of the Y-mixer using a ribozyme-free plastic centrifuge tube. The appearance of the preparation was observed and accurately recorded.

2.5. Removal of Organic Solvent

With the above formulation as an example, the mixed solution of the lipid nanoparticles prepared by the Y-mixer contained about 25% (v/v) organic solvent ethanol. 552 μL lipid nanoparticle mixture solution obtained in step 4 was accurately pipetted and gently transferred to a clean heart-shaped flask (10 mL in size) treated by ultraviolet radiation. The ethanol was removed by spin-evaporation (Jinan Olabo Scientific Instrument Co., Ltd., RE-2000E) at room temperature under vacuum condition. During the spin-evaporation, solution boiling of solution, precipitation of the preparation, and change of appearance of the preparation was closely monitored and recorded, as well as the starting and ending time of spin-evaporation.

2.6. Standing Incubation of the Lipid Nanoparticle

With the above formulation as an example, after the completion of the spin-evaporation in step 5, gently transferred the lipid nanoparticle solution in the flask to a ribozyme-free plastic centrifuge tube, let it stand for about 15 minutes, and adjusted the lipid nanoparticles to 414 μL. The solvent used for the volume adjustment was ribozyme-free water (Millipore Corporation, Milli-Q Direct 8 purification system). Lipid nanoparticles encapsulating the nucleic acid drugs were obtained.

The obtained nucleic acid lipid nanoparticle preparation contained about 0.04 mg/mL FLuc-mRNA, about 1.09 mg/mL compound L0181, and a concentration of the total lipid of about 2.06 mg/mL, regardless of loss. 235 μL of the obtained lipid nucleic acid nanoparticle preparation was used to verify the in vivo transfection in small animals, 120 μL was used to verify the in vitro transfection effect and cytotoxicity, 20 μL was used to measure the surface potential of the nanoparticles, 7.5 μL was used to detect the nanoparticle size and dispersion index (PDI), 7.5 μL was used in the gel electrophoresis to analyze the degree of nucleic acid encapsulation, 5 μL was used to determine the nucleic acid encapsulation rate by fluorescence, and the remaining preparation solution was used for electron microscopy.

2.7. Dialysis and Replacement of Solvent

The nucleic acid lipid nanoparticle preparation obtained in step 6 can be dialyzed to further remove possible residual ethanol and replace the solvent with another solvent, such as isotonic phosphate buffer solution. In the clean preparation room, the nucleic acid lipid nanoparticle solution was loaded into a dialysis membrane with a molecular weight interception size of 8 kD and dialyzed against the isotonic phosphate buffer solution at room temperature for 3-4 hours. The volume ratio of the solution used for dialysis to the nucleic acid lipid nanoparticle solution is at least greater than 500:1. After dialysis, the lipid nanoparticle solution was gently transferred from the dialysis membrane to a ribozyme-free plastic centrifuge tube for sparse use.

2.8. Addition of Excipient and/or Cryoprotectant

Excipients and/or cryoprotectants, such as sucrose, can be added to the nucleic acid lipid nanoparticle preparation obtained in step 6 or to the nucleic acid lipid nanoparticle preparation obtained after dialysis in step 7. As an example, 40% sucrose (Aladdin Reagent (Shanghai) Co., Ltd.) was added to the nucleic acid lipid nanoparticle preparation with the volume ratio of 3:1, which is mixed homogeneously to obtain nucleic acid lipid nanoparticle preparation containing 10% sucrose, and further aliquoted into ribozyme-free centrifuge tubes and stored in an ice box, 4° C., −20° C., and/or −80° C. refrigerator for later use. Physicochemical property measurement and in vivo effect validation of the lipid nanoparticles were performed after thawing and returning to room temperature after storage for the indicated time.

2.9. Concentration of the Nucleic Acid Lipid Nanoparticle Solution

The nucleic acid lipid nanoparticle solution obtained in steps 6, 7 and 8 can be concentrated by spin distillation. Specifically, in the clean preparation room, the nucleic acid lipid nanoparticle solution is gently transferred to a UV radiation-treated clean heart-shaped flask, and the water in the solution is removed and the preparation is concentrated by spin-distillation under vacuum at room temperature or heat (not exceeding 40° C.). The time of concentration by spinning varies with different preparations, and optionally within 1 minute to 2 hours.

3. Encapsulation Degree of the Nucleic Acid Detected by Gel Electrophoresis 3.1. Gel preparation: Prepare 1% agarose solution. Weigh 0.8 g agarose powder (BioFroxx), transfer to a conical flask, add 80 mL of TAE buffer, shake well, and use a microwave oven to heat until agarose powder is completely dissolved. At the end of the heating process, place the hot agarose solution at room temperature, and slowly cool it down.

3.2. Snap the clean gel-making mold tightly onto the gel-making slot.

3.3. When the agarose solution cools down to 40 to 50° C., add 8 μL of SYBR Safe dye (Thermo Fisher Scientific), shake well, and then pour the agarose solution onto the gel-making mold in one go, taking care not to create air bubbles. Immediately afterwards, a clean gel-making comb was stuck onto the gel-making mold.

3.4. Allow the gel to stand at room temperature for 30 to 60 minutes, gently pull out the comb, and transfer the agarose gel to the electrophoresis tank with TAE buffer.

3.5. Add 5×loading buffer to the running sample, mix well, and add it to the gel wells, which are located at the negative end.

3.6. After the sample is loaded, cover the electrophoresis tank tightly, turn on the electrophoresis instrument (Bio-Rad Laboratories (Shanghai) Co., Ltd., PowerPac™ Basic), set the parameters to 80 V, 30 min, and press the start button.

3.7. Use the gel imager (Shanghai Tanon Life Science Co., Ltd., Tanon 1600) to image the results of agarose electrophoresis.

4. Encapsulation Efficiency of the Nucleic Acid Detected by Fluorescence

The nucleic acid encapsulation rate of the nucleic acids lipid nanoparticle formulations obtained in steps 6, 7, and 8 can be determined by fluorescence methods, such as using the Quant-iT™ RiboGreen RNA Quantification Kit (Thermo Fisher Scientific). Take the RiboGreen RNA Quantification Kit as an example: Configure the low-range working solution and mRNA standard solution according to the instructions. Take 3 μL of the nucleic acid lipid nanoparticle solution obtained in step 6, add 297 μL of the Tris-EDTA buffer (TE buffer) provided with the kit, mix well, and then suck up 100 μL of it into the black-bottomed ninety-six-well plate, and then add 100 μL of the RiboGreen low-range detection working solution. Add 100 μL of different concentrations of mRNA standard solution into the black bottom 96-well plate, and add 100 μL of RiboGreen low-range detection working solution. After gently blowing and mixing well, incubate for 5 minutes away from light, and then immediately detect and record the fluorescence signal intensity using a multifunctional enzyme labeling instrument (BMG LABTECH, FLUOstar Omega). The free mRNA content not encapsulated by the lipid nanoparticles was calculated by standard curve fitting and calculation, and then divided by the total amount of mRNA in the wells detected to find the nucleic acid encapsulation rate of this nucleic acid lipid nanoparticle preparation.

5. Detection of Particle Size, Potential, Osmotic Pressure, and Electron Microscopy Imaging of Nucleic Acid Lipid Nanoparticle Preparations 5.1. Particle Size Characterization of Nucleic Acid Lipid Nanoparticle Preparations The 7.5 μL nucleic acid lipid nanoparticle solution (containing approximately 0.04 mg/mL mRNA) was taken and added with 200 μL ultrapure water, mixed by gentle blowing using a pipette tip, and the particle size of the nanopreparation was detected by dynamic lightscattering (DLS) using a Malvern Dynamic Light Scattering Instrument (Malvern Instruments Ltd., ZEN3700, UK).

5.2. Potential Characterization of Nucleic Acid Lipid Nanoparticle Preparations

20 μL of the nucleic acid lipid nanoparticle solution (containing about 0.04 mg/mL mRNA) was taken and added with 780 μL of ultrapure water, used a pipette tip to gently blow and mix, and the potential of the nanopreparation was detected by Malvern particle sizer (model ZEN3700).

5.3. Osmotic Pressure Characterization of Nucleic Acid Lipid Nanoparticle Preparations 50 μL of the nucleic acid lipid nanoparticle solution (containing about 0.04 mg/mL mRNA) was taken and the osmotic pressure of the nanopreparation was detected by freezing point penetrometer (Gonotec GmbH, OSMOMAT 3000-D).

5.4. Simultaneous Characterization of Particle Size and Potential of Nucleic Acid Lipid Nanoparticle Preparations 27.5 μL nucleic acid lipid nanoparticle solution (containing about 0.04 mg/mL mRNA) was taken and added with 200 μL ultrapure water. A pipette tip was used to gently blow the sample and mix well. The particle size of the nanopreparation was detected by Malvern Dynamic Light Scattering Instrument (Malvern Instruments Ltd., ZEN3700, UK). After the detection, the sample was recovered to an EP tube, and 600 μL of ultrapure water was added, gently blown with a pipette tip, and the potential of the nanopreparation was measured by a Malvern particle size meter.

5.5. Characterization by Electron Microscopy

Placed the carbon mesh face up in the center of the nuclease-free EP tube cap. Pipetted 10 μL of the prepared TEM sample (nanoparticle preparation) onto the carbon mesh. Let it stand at room temperature, after the water in the sample evaporated and the carbon mesh was semi-dry (optimal when there was only a film of water on the carbon mesh), 10 μL of nuclease-free water was dropped on the surface of the carbon mesh with a pipette, and the droplets on the surface of the carbon mesh were sucked up with a filter paper after a 10-s period of time. Washed the sample with the nuclease-free water for two times repeatedly. 10 μL of negative dyeing solution was added to the surface of carbon mesh to negative dyeing for 30 s, then the negative dyeing solution was absorbed with filter paper. Cleaned the sample twice with nuclease-free water, let stand on the table, and waited until the water on the surface of the carbon mesh evaporated and dried up. The preparation of samples is completed. The samples were sent for TEM photography using a lanthanum hexaboride transmission electron microscope (FEI Tecnai G2 12,120 KV, FEI, USA).

6. Transfection Effect and Cytotoxicity of Nucleic Acid Lipid Nanoparticle Preparations in Cells 6.1. Cell Seeding A549 cells were digested and collected the day before treatment and the cell concentration was adjusted to $2*10^5$ cells/mL, 200 μL cell culture medium with a concentration of $2*10^5$ cells/mL was added to the 96-well plate, resulting in approximately $4*10^4$ cells per well in the 96-well plate. Digested and collected DC2.4 cells and adjusted the cell concentration to $1*10^5$ cells/mL, added 200 μL cell culture medium with a concentration of $1*10^5$ cells/mL to the 96-well plate, so that the number of cells per well in the 96-well plate is approximately $2*10^4$. The cells were incubated in a cell culture incubator (Esco Micro Pte Ltd, Singapore, CLM-170B-8-NF) at 37° C. 5% CO2 for 24 h.

6.2. Cell Treatment

On the day of cell treatment, the medium (Thermo Fisher Scientific) was aspirated from the 96-well plate, 200 μL of PBS was added to each well to rinse the cells and then the PBS (Thermo Fisher Scientific) was removed, and 180 μL of opti-MEM (Thermo Fisher Scientific) was added to each well of the treatment group.

Different volumes of the preparation were taken and diluted by adding the buffer used for the preparation or the buffer used for dialysis, and four dosing concentrations were prepared for each preparation, and 20 μL of the diluted nanopreparation was added to each well of a 96-well plate (3 replicate wells for each concentration), and the dosing concentrations of the preparation were about 50 ng mRNA/well, 100 ng mRNA/well, 200 ng mRNA/well, and 300 ng mRNA/well, respectively.

The 96-well cell culture plate was placed in a cell culture incubator and incubated at 37° C. 5% $CO_2$ for 4 h. The medium was sucked up, and 200 μL of DMEM complete medium was added to each well and incubated for 20 h for detection.

6.3. Cell Transfection Assay

D-Luciferin (Biohub International Trade Co., Ltd.) stock solution (9900 μL of complete medium+100 μL of 25 mg/mL of D-Luciferin stock solution) was diluted with DMEM complete medium at 99:1 to make a working solution at the concentration of 250 μg/mL (25 μg per well).

The 96-well cell culture plate was taken out and the supernatant was removed. Before imaging, the 96-well plate was added with 100 μL of D-Luciferin working solution, incubated at 37° C. for 5 min, and imaged and analyzed by the plate reader.

6.4. Cytotoxicity Assay

Diluted CCK-8 detection reagent (Shanghai Beyotime Biotechnology Co., Ltd.) masterbatch (900 μL complete medium+100 μL CCK-8 detection reagent) with DMEM complete medium at 9:1 to prepare CCK-8 working solution.

Take out the 96-well cell culture plate and removed the supernatant. Before detection, the 96-well plate was added with 100 μL CCK-8 working solution, incubated in the cell culture incubator at 37° C. 5% $CO_2$ for 2 h, and analyzed by plate reader. The cell viability was calculated to reflect the cytotoxicity.

7. In Vivo Delivery of the Nucleic Acid Lipid Nanoparticle Preparations in Mice

After the preparation was completed, the preparation was injected intramuscularly (mice rectus femoris muscle of the thigh) or intravenously (mice tail vein), with approximately 75 μL per mouse, for a total of 3 mice. After a certain time of injection, in vivo imaging (PerkinElmer, IVIS Lumina III) was performed. 10-15 minutes before imaging, 200 μL of 15 mg/mL D-Luciferin working solution was injected intraperitoneally, and the imaging analysis was performed using an in vivo imager.

8. In Vivo Toxicity of the Nucleic Acid Lipid Nanoparticle Preparations in Mice

After the preparation was administered in mice for 3 h, whole blood was taken from mice by canthus extraction, part of the whole blood was taken and added with anticoagulant for routine blood tests, and part of the whole blood was centrifuged at 5000 rcf for 5 min at 4° C., and the supernatant was transferred to clean 1.5 mL centrifuge tubes for blood biochemistry tests. The samples were stored at room temperature, and the blood routine and blood biochemical indexes were detected by automatic animal blood cell analyzer (Shenzhen Mindray Animal Medical Technology Co., Ltd., BC-2800 Vet) and automatic animal biochemical detection system (Shenzhen Mindray Animal Medical Technology Co., Ltd., BS-240 Vet) within one hour.

9. In Vivo Immunization Effect of Nucleic Acid Lipid Nanoparticle Preparations in Mice 9.1. In Vivo Immunization Lipid nanoparticles encapsulating the nucleic acid drugs were prepared according to step 2. The mRNA was replaced with Delta Spike full length mRNA (Shanghai Zhaowei Science and Technology Development Co., Ltd.) and then administered to the mice at a dose of 5 μg per mouse, and on the 14th day after the first immunization, the whole blood of the mice was collected by canthus sampling, and the drug administration was repeated for the second immunization. On the 14th day after the second immunization, the whole blood was collected from mice by canthus sampling. The whole blood was centrifuged at 5000 rcf for 5 mn, and the supernatant was centrifuged at 10000 rcf for 5 min to obtain the serum, which was aliquated into serial tubes and stored in the refrigerator at −20° C.

9.2. ELISA or ELISA Titer Assay to Detect Specific Antibody Levels 9.2.1 Coating: Add 100 μL of 0.2 μg/100 μL Delta-S protein (Novoprotein Scientific Inc.) dilution solution to each well, and leave it in the refrigerator at 4° C. overnight.

9.2.2 Washing: Add 200 μL of PBST (PBS buffer solution containing 0.05% Tween-20 at pH 7.4) to each well and wash three times.

9.2.3 Blocking: Add 200 μL of 5% (w/v) BSA-PBS solution (BSA bovine serum albumin, Bioss Biotechnology Co., Ltd.) to each well, and shake for 2 h at 50 rcf at room temperature using a shaker.

9.2.4 Washing: Add 200 μL of PBST to each well to wash once.

9.2.5 Adding samples: Add 100 μL of serum diluted 200 times with PBS (0.5 μL of serum) to each well (for the ELISA titer assay, serum diluted 200 times, 800 times, 3200 times, 12800 times, 51200 times, 204800 times), and shake at room temperature for 2 h at 50 rcf using a shaker.

9.2.6 Washing: Add 200 μL of PBST into each well for three times.

9.2.7 Adding detection antibody: Add 100 μL of HRP-labeled goat anti-mouse IgG detection antibody (0.1 μL of antibody master batch) (Sangon Biotech (Shanghai) Co., Ltd.) diluted 1000-fold into each well, and shake at 50 rcf for 1 h at room temperature using a shaker.

9.2.8 Washing: Add 200 μL of PBST to each well and wash three times.

9.2.9 Adding TMB (Beijing Solarbio Science & Technology Co., Ltd.): Add 50 μL of TMB mixture with the volume ratio of liquid A:liquid B of 1:1 to each well, and react for 5 mn (ELISA of blood sample I), 7 min 58 sec (ELISA of blood sample II), and react for about 5 min (ELISA titer of blood sample II).

9.2.10 Adding phosphate (Aladdin Reagent (Shanghai) Co., Ltd.): add 50 μL of 1 mol/L phosphate per well to terminate the reaction.

9.2.11 Detection: Use multi-function plate reader for detection.

9.3. Neutralization Antibody Levels Detected by Pseudovirus Neutralization Assay 9.3.1 Cell seeding: 293T-ACE2 cells (Fubio (Suzhou) Biomedical Technology Co., Ltd.) were inoculated with $1\times10^5$ cells in each well of a 48-well plate at a concentration of $1\times10^5$ cells in 300 μL of DMEM medium (containing 10% heat-inactivated FBS without bispecific antibody), the 48-well plate was labeled with information such as "number, cell type, number of generations, medium type, date and name", and then the cells were cultured in a cell culture incubator at 37° C. with 5% $CO_2$ for 18 hours.

9.3.2 Before the pseudovirus transfection operation, prepare an ice box, re-dissolve the serum to be used on ice, thaw on ice the virus from the −25° C. refrigerator. After thawing, the serum and pseudovirus were flicked homogenously and centrifuged with a palm centrifuge.

9.3.3 Examine the neutralization antibody with serum diluted in different ratios: use complete culture medium to dilute the pseudovirus (Fubio (Suzhou) Biomedical Technology Co., Ltd.) and mouse serum respectively, mix them well, and then dilute them 40-fold, 100-fold, 250-fold and 625-fold according to the final concentration of the cells of incubation. 150 μl of pseudovirus-serum mixture was added into each well and 5 wells out of them were added with pseudovirus dilutions as positive control.

9.3.4 The 48-well plate was taken from the carbon dioxide incubator and the medium was sucked up using waste liquid pump. The serum and pseudovirus were mixed for about 20 min and 150 μL of the mixture were added into each well one by one. The position of the different groups was recorded, and 5 wells out of them were added with only 150 μl medium as the negative control.

9.3.5 The 48-well cell culture plate was placed into the incubator for 18 h after spraying alcohol.

9.3.6 After 18 h of pseudovirus transfection, the 48-well plate was taken out from the $CO_2$ incubator and the transfection results was observed under a fluorescence inverted microscope (Carl Zeiss, Germany, primovert). Cells from each well were collected into a 1.5 mL centrifuge tube and centrifuged for 5 min at 300 G with a freezing centrifuge (Eppendorf, Germany, 5910R). The supernatant was sucked up using a waste liquid pump, and the cells were resuspended by adding 200 μl of PBS to each 1.5 mL centrifuge tube. The cells were placed on ice and assayed using a flow cytometer (BD Biosciences, Canto II analyzer).

Results

Various lipid nanoparticle formulations with some of the compounds of Table IA (L0180, L0181, L0182, L0183, L0184, L0185, L0186, L0187, L0188, L0189, L0190, L0191, L0192, L0193, L0194, L0195, L0196, L0197, L0198, L0199, L0200, L0201, L0202, and L0203) were prepared and tested. SM-102 (Moderna) was used as reference compound. The testing results are shown in Tables 2-3 below.

TABLE 2

Initial screening of lipids

| Comp No. | Molar ratio in Formulation* | N/P[#] | In vivo Route | In vivo IVIS[$] | Particle size (nm) | PDI^ |
|---|---|---|---|---|---|---|
| L0180 | 1.40:11.15:38.95:48.50 | 21 | IV | $3.15 \times 10^6$ | 86.34 ± 1.35 | 0.18 ± 0.01 |
| | 1.09:8.66:30.25:60.00 | 21 | IM | $1.10 \times 10^7$ | 84.26 ± 0.81 | 0.13 ± 0.01 |
| L0181 | 1.71:12.98:45.31:40.00 | 30 | IM | $3.37 \times 10^6$ | 71.39 ± 0.26 | 0.16 ± 0.02 |
| L0182 | 1.40:11.15:38.95:48.50 | 30 | IV | $4.99 \times 10^6$ | 83.26 ± 0.68 | 0.14 ± 0.01 |
| | 1.09:8.66:30.25:60.00 | 30 | IM | $3.25 \times 10^7$ | 89.38 ± 0.09 | 0.16 ± 0.01 |

TABLE 2-continued

| Initial screening of lipids | | | | | | |
|---|---|---|---|---|---|---|
| Comp No. | Molar ratio in Formulation* | N/P# | In vivo Route | IVIS$ | Particle size (nm) | PDI^ |
| L0183 | 1.40:11.15:38.95:48.50 | 24 | IV | $5.98 \times 10^7$ | 75.73 ± 0.33 | 0.14 ± 0.01 |
| | 1.63:12.99:45.38:40.00 | 24 | IM | $2.37 \times 10^7$ | 94.49 ± 1.06 | 0.16 ± 0.01 |
| L0184 | 1.40:11.15:38.95:48.50 | 50 | IV | $1.17 \times 10^8$ | 119.60 ± 0.40 | 0.06 ± 0.00 |
| | 1.09:8.66:30.25:60.00 | 50 | IM | $4.88 \times 10^6$ | 128.20 ± 0.95 | 0.09 ± 0.01 |
| L0185 | 1.40:11.15:38.95:48.50 | 30 | IV | $2.72 \times 10^6$ | 84.46 ± 1.39 | 0.20 ± 0.00 |
| | 0.95:7.58:26.47:65.00 | 30 | IM | $2.52 \times 10^7$ | 94.35 ± 0.52 | 0.13 ± 0.02 |
| L0186 | 1.40:11.15:38.95:48.50 | 18 | IV | $2.77 \times 10^8$ (body) $5.61 \times 10^7$ (liver) $2.65 \times 10^7$ (spleen) | 89.99 ± 0.58 | 0.12 ± 0.00 |
| | | | IM | $1.58 \times 10^8$ | | |
| L0187 | 1.40:11.15:38.95:48.50 | 20 | IV | $1.11 \times 10^8$ (body) $2.46 \times 10^7$ (liver) $2.00 \times 10^7$ (spleen) | 80.11 ± 0.17 | 0.12 ± 0.01 |
| | | | IM | $9.72 \times 10^7$ | | |
| L0188 | 1.40:11.15:38.95:48.50 | 27 | IV | $1.61 \times 10^8$ (body) | 97.72 ± 1.19 | 0.22 ± 0.02 |
| | | | IV | $4.17 \times 10^7$ (liver) | | |
| | | | IV | $4.65 \times 10^7$ (spleen) | | |
| | | | IM | $1.87 \times 10^7$ | | |
| L0189 | 1.40:11.15:38.95:48.50 | 10 | IV | $3.12 \times 10^7$ | 85.92 ± 0.69 | 0.07 ± 0.02 |
| | 1.09:8.66:30.25:60.00 | 20 | IM | $2.16 \times 10^6$ | 106.80 ± 0.85 | 0.06 ± 0.04 |
| L0190 | 1.71:12.98:45.31:40.00 | 40 | IM | $1.19 \times 10^6$ | 121.87 ± 2.71 | 0.20 ± 0.01 |
| L0191 | 1.71:12.98:45.31:40.00 | 40 | IV | $4.36 \times 10^9$ | 92.00 ± 0.39 | 0.15 ± 0.02 |
| | 1.50:11.50:38.50:48.50 | 24 | IV | $1.28 \times 10^9$ (body) $1.03 \times 10^8$ (spleen) $2.77 \times 10^8$ (liver) | 75.33 ± 0.78 | 0.10 ± 0.01 |
| | 1.50:20.00:33.50:45.00 | 40 | IM | $8.97 \times 10^7$ | 70.87 ± 0.35 | 0.17 ± 0.01 |
| L0192 | 1.77:14.07:49.16:35.00 | 54 | IM | $2.13 \times 10^8$ | 96.59 ± 0.78 | 0.08 ± 0.02 |
| | 1.50:4.00:59.50:35.00 | 65 | IV | $5.56 \times 10^{10}$ | 112.83 ± 0.31 | 0.15 ± 0.01 |
| | 1.77:14.07:59.16:25.00 | 52 | IM | $1.26 \times 10^8$ | 113.33 ± 1.07 | 0.11 ± 0.02 |
| L0193 | 1.40:11.15:38.95:48.50 | 12 | IV | $4.33 \times 10^5$ | 93.86 ± 0.59 | 0.11 ± 0.02 |
| | 1.40:11.15:38.95:48.50 | 12 | IM | $2.43 \times 10^5$ | 93.86 ± 0.59 | 0.11 ± 0.02 |
| L0194 | 1.40:11.15:38.95:48.50 | 12 | IV | $2.14 \times 10^5$ | 109.10 ± 0.50 | 0.13 ± 0.00 |
| | 1.40:11.15:38.95:48.50 | 12 | IM | $1.08 \times 10^6$ | 109.10 ± 0.50 | 0.13 ± 0.00 |
| L0195 | 1.40:11.15:38.95:48.50 | 24 | IV | $4.54 \times 10^5$ | 90.79 ± 0.65 | 0.17 ± 0.02 |
| | | | IM | $6.81 \times 10^5$ | | |
| L0196 | 1.40:11.15:38.95:48.50 | 40 | IV | $2.00 \times 10^9$ | 89.18 ± 0.22 | 0.11 ± 0.01 |
| | | | IM | $1.82 \times 10^8$ | | |
| L0197 | 1.40:11.15:38.95:48.50 | 24 | IV | $5.97 \times 10^8$ (body) $2.34 \times 10^6$ (liver) $7.26 \times 10^7$ (spleen) | 102.47 ± 0.25 | 0.13 ± 0.02 |
| | | | IM | $3.81 \times 10^6$ | | |
| L0198 | 1.40:11.15:38.95:48.50 | 30 | IV | $4.61 \times 10^7$ | 90.47 ± 0.74 | 0.17 ± 0.01 |
| | | | IM | $9.58 \times 10^6$ | | |
| L0199 | 1.40:11.15:38.95:48.50 | 40 | IM | $2.19 \times 10^7$ | 97.65 ± 0.59 | 0.11 ± 0.01 |
| | 2.50:7.00:42.00:48.50 | 55 | IV | $1.07 \times 10^9$ | 130.00 ± 1.47 | 0.12 ± 0.01 |
| L0200 | 1.40:11.15:38.95:48.50 | 65 | IM | $3.08 \times 10^5$ | 117.90 ± 0.36 | 0.08 ± 0.02 |
| | 1.00:7.00:57.00:35.00 | 35 | IV | $2.82 \times 10^{10}$ | 106.93 ± 0.71 | 0.06 ± 0.01 |
| | 2.00:16.00:22.00:60.00 | 35 | IV | $1.05 \times 10^9$ | 104.50 ± 0.26 | 0.12 ± 0.01 |
| L0201 | 1.40:11.15:38.95:48.50 | 60 | IV | $4.46 \times 10^6$ (body) $5.29 \times 10^8$ (liver) $7.89 \times 10^7$ (spleen) | 119.70 ± 0.61 | 0.07 ± 0.01 |
| | | | IM | $2.18 \times 10^6$ | | |
| L0202 | 1.40:11.15:38.95:48.50 | 50 | IV | $3.73 \times 10^9$ | 114.43 ± 0.96 | 0.07 ± 0.02 |
| | | | IM | $9.20 \times 10^7$ | | |

TABLE 2-continued

| Initial screening of lipids | | | | | | |
|---|---|---|---|---|---|---|
| Comp No. | Molar ratio in Formulation* | N/P# | In vivo Route | IVIS$ | Particle size (nm) | PDI^ |
| L0203 | 1.40:11.15:38.95:48.50 | 30 | IV | $3.89 \times 10^8$ | 126.73 ± 1.50 | 0.06 ± 0.01 |
| | | | IM | $8.01 \times 10^7$ | | |
| SM-102 | 1.40:11.15:38.95:48.50 | 10 | IV | $1.40 \times 10^9$ | 81.71 ± 0.49 | 0.11 ± 0.01 |

*All formulations used DMG-PEG2000:DSPC:Chol:Lipid (e.g., compound L0181) with mRNA
#N/P: N/P ratio, molar ratio between amines (N) and phosphates (P)
$IVIS: in vivo imaging fluorescent signal intensity; based on whole body scan unless a specific organ is specified
^PDI: polydispersity value As shown in Table 2, all of the tested formulations exhibited low particle sizes and narrow size distribution (PDI). In particular, certain formulations with Compounds L0186, L0187, L0191, L0192, L0196, L0199, L0200, L0201, L0202, and L0203 all had superior in vivo delivery efficiency as compared to the benchmark compound SM102.

TABLE 3

| Compound L191 in vitro data and additional measurements | | | | | |
|---|---|---|---|---|---|
| No. | Molar ratio | Zeta potential | encap-sulation efficiency | osmotic pressure | in vitro dose (ng/well) |
| 1 | 1.50:20:33.50:45.00 | 11.30 ± 0.69 | 96.26% | 2139 | 50 |
| | | | | | 100 |
| | | | | | 200 |
| | | | | | 300 |
| 2 | 1.50:11.50:38.50:48.50 | 12.67 ± 0.61 | 97.92% | — | 50 |
| | | | | | 100 |
| | | | | | 200 |
| | | | | | 300 |

TABLE 3-continued

| No. | A549 transfection/RLU | A549 cellular tox (% cells alive) | DC2.4 cell transfection/RLU | DC2.4 cellular tox (% cells alive) |
|---|---|---|---|---|
| 1 | 61522.00 ± 4200.55 | 103.42% | 44580.00 ± 5193.04 | — |
| | 80557.33 ± 20503.88 | 105.39% | 38457.67 ± 2948.52 | — |
| | 81404.33 ± 378.95 | 103.90% | 51212.00 ± 7734.10 | — |
| | 84806.33 ± 13267.99 | 103.50% | 49462.00 ± 12586.07 | — |
| 2 | 31491.33 ± 4435.56 | 103.82% | 22385.67 ± 3001.79 | 95.97% |
| | 54866.67 ± 14929.46 | 105.86% | 31266.67 ± 5408.83 | 87.33% |
| | 90775.67 ± 20487.67 | 109.06% | 45175.33 ± 19991.64 | 75.79% |
| | 88154.33 ± 37821.07 | 104.35% | 66928.33 ± 3066.07 | 92.20% |

As shown in Table 3, all tested formulations of Compound L191 exhibited high encapsulation and transfection efficiency, and low to no cellular toxicity (even at high doses, e.g., 300 ng/well).

Moreover, both formulations of Compound L191 exhibited excellent stability after storage under different conditions, including physical stability and in vivo delivery efficiency.

In a second batch, compounds L0207, L0208, L0209, L0210, L0211, L0212, L0213, L0214, L0215, L0216, L0217, L0218, L0219, L0220, L0221, L0222, L0223, L0224, L0225, L0226, L0227, L0228, and L0229 were tested with the same assays as described above. In addition, two comparative compounds, L0191-Control and L0199-Control, were prepared. Relative to L0191 and L0199, these comparative compounds did not include the hydroxy groups (see Table 11B). The testing results are shown in Table 4.

TABLE 4

| Testing of second batch of compounds | | | | | | |
|---|---|---|---|---|---|---|
| Comp No. | Molar ratio in Formulation | N/P | In vivo Route | In vivo IVIS | Particle size (nm) | PDI |
| L0207 | 1.40:11.15:38.95:48.50 | 20 | IM | $1.75 \times 10^5$ | 172.13 ± 1.53 | 0.19 ± 0.00 |
| | | | IV | $2.41 \times 10^5$ | | |
| L0208 | 1.40:11.15:38.95:48.50 | 20 | IM | $1.94 \times 10^6$ | 176.67 ± 1.97 | 0.14 ± 0.03 |
| | | | IV | $2.27 \times 10^5$ | | |
| L0209 | 1.50:6.00:57.50:35.00 | 48 | IM | $7.33 \times 10^8$ | 84.17 ± 0.31 | 0.13 ± 0.02 |
| | 1.00:6.00:44.50:48.50 | 40 | IV | $1.52 \times 10^{10}$ | 99.95 ± 0.74 | 0.06 ± 0.03 |
| L0210 | 1.40:11.15:38.95:48.50 | 40 | IM | $2.48 \times 10^7$ | 94.89 ± 0.78 | 0.15 ± 0.01 |
| | 1.00:16.00:48.00:35.00 | 30 | IV | $6.93 \times 10^9$ | 101.83 ± 0.21 | 0.15 ± 0.01 |
| L0211 | 1.40:11.15:38.95:48.50 | 20 | IM | $1.37 \times 10^5$ | 134.47 ± 2.72 | 0.22 ± 0.00 |
| | | | IV | $1.36 \times 10^5$ | | |
| L0212 | 1.40:11.15:38.95:48.50 | 20 | IM | $1.40 \times 10^7$ | 95.87 ± 0.24 | 0.18 ± 0.01 |
| | | | IV | $1.38 \times 10^8$ | | |
| L0213 | 1.40:11.15:38.95:48.50 | 20 | IM | $2.36 \times 10^5$ | 174.43 ± 1.85 | 0.18 ± 0.01 |
| | | | IV | $3.64 \times 10^5$ | | |
| L0214 | 1.40:11.15:38.95:48.50 | 20 | IM | $2.46 \times 10^5$ | 177.07 ± 1.00 | 0.21 ± 0.01 |
| | | | IV | $3.60 \times 10^5$ | | |
| L0215 | 1.40:11.15:38.95:48.50 | 20 | IM | $2.45 \times 10^5$ | 119.27 ± 1.75 | 0.11 ± 0.01 |
| | | | IV | $4.06 \times 10^5$ | | |
| L0216 | 1.40:11.15:38.95:48.50 | 20 | IM | $3.58 \times 10^5$ | 117.97 ± 1.91 | 0.08 ± 0.02 |
| | | | IV | $2.18 \times 10^5$ | | |
| L0217 | 1.40:11.15:38.95:48.50 | 20 | IM | $2.97 \times 10^6$ | 87.05 ± 0.47 | 0.09 ± 0.02 |
| | | | IV | $2.87 \times 10^7$ | | |
| L0218 | 1.40:11.15:38.95:48.50 | 20 | IM | $8.49 \times 10^5$ | 109.43 ± 1.16 | 0.07 ± 0.02 |
| | | | IV | $5.55 \times 10^5$ | | |
| L0219 | 1.40:11.15:38.95:48.50 | 20 | IM | $2.79 \times 10^6$ | 102.47 ± 0.96 | 0.09 ± 0.01 |
| | | | IV | $8.48 \times 10^7$ | | |
| L0220 | 1.40:11.15:38.95:48.50 | 30 | IM | $1.32 \times 10^6$ | 106.97 ± 0.21 | 0.08 ± 0.02 |
| | | | IV | $1.82 \times 10^8$ | | |
| L0221 | 1.40:11.15:38.95:48.50 | 30 | IM | $1.85 \times 10^5$ | 140.97 ± 1.48 | 0.07 ± 0.02 |
| | | | IV | $3.94 \times 10^5$ | | |
| L0222 | 1.40:11.15:38.95:48.50 | 30 | IM | $4.38 \times 10^5$ | 133.83 ± 0.72 | 0.05 ± 0.01 |
| | | | IV | $7.94 \times 10^6$ | | |
| L0223 | 1.40:11.15:38.95:48.50 | 30 | IM | $1.83 \times 10^6$ | 98.88 ± 1.32 | 0.13 ± 0.03 |
| | | | IV | $1.42 \times 10^8$ | | |
| L0224 | 2.00:4.00:59.00:35.00 | 35 | IM | $3.31 \times 10^8$ | 84.67 ± 0.79 | 0.14 ± 0.01 |
| | 1.40:11.15:38.95:48.50 | 36 | IV | $4.84 \times 10^9$ | 108.57 ± 1.60 | 0.07 ± 0.02 |
| L0225 | 1.40:11.15:38.95:48.50 | 36 | IM | $3.13 \times 10^8$ | 117.87 ± 1.55 | 0.10 ± 0.01 |
| | | | IV | $2.15 \times 10^9$ | | |
| L0226 | 1.40:11.15:38.95:48.50 | 36 | IM | $1.41 \times 10^8$ | 115.53 ± 1.04 | 0.09 ± 0.03 |
| | | | IV | $1.24 \times 10^9$ | | |
| L0227 | 2.00:4.00:59.00:35.00 | 35 | IM | $3.49 \times 10^8$ | 112.03 ± 0.65 | 0.13 ± 0.01 |
| | 1.40:11.15:38.95:48.50 | 32 | IV | $2.49 \times 10^8$ | 113.50 ± 0.96 | 0.15 ± 0.01 |
| L0228 | 1.40:11.15:38.95:48.50 | 28 | IM | $8.22 \times 10^6$ | 140.50 ± 1.21 | 0.18 ± 0.01 |
| | 2.50:11.50:51.00:35.00 | 32 | IV | $9.28 \times 10^9$ | 120.07 ± 0.60 | 0.13 ± 0.01 |
| L0229 | 1.40:11.15:38.95:48.50 | 32 | IM | $5.61 \times 10^6$ | 179.07 ± 0.38 | 0.10 ± 0.02 |
| | | | IV | $2.46 \times 10^8$ | | |
| L0191-Control | 1.50:20.00:33.50:45.00 | 40 | IM | $1.07 \times 10^6$ | 153.57 ± 1.17 | 0.13 ± 0.00 |
| L0191 | | | | $2.12 \times 10^7$ | 111.60 ± 1.21 | 0.12 ± 0.00 |
| L0191-Control | 1.00:16.00:34.50:48.50 | 40 | IV | $2.30 \times 10^6$ | 186.33 ± 4.02 | 0.40 ± 0.01 |
| L0191 | | | | $9.64 \times 10^8$ | 133.87 ± 1.86 | 0.13 ± 0.02 |
| L0199-Control | 1.40:11.15:38.95:48.50 | 40 | IM | $5.84 \times 10^6$ | 133.43 ± 1.86 | 0.17 ± 0.02 |
| L0199 | | | | $5.93 \times 10^6$ | 123.50 ± 0.36 | 0.09 ± 0.02 |
| L0199-Control | 1.50:16.00:34.00:48.50 | 55 | IV | $2.12 \times 10^7$ | 144.33 ± 0.31 | 0.16 ± 0.03 |
| L0199 | | | | $9.35 \times 10^8$ | 147.57 ± 1.17 | 0.10 ± 0.02 |

Like in the first batch, these compounds exhibited excellent particle sizes and distribution in vivo delivery efficiency. Interestingly, the delivery efficiency of L0191-Control was about 420 times and 20 times lower than L0191, for IV and IM administrations, respectively. Likewise, the delivery efficiency of L0199-Control was about 44 times lower than L0199 for IV administration (and slightly lower for IM administration). Such comparative data, therefore, demonstrate the importance of the removed hydroxy groups.

In the next assay, animals administered with certain test compounds (L0186, L0187, L0192, L0199, L0200, and L0203, with SM-102 as control) were immunized again, and serum samples were obtained. Measured OD values (Table 5) indicate the amounts of anti-S protein antibodies, which correlated to the expressed S protein in the serum.

TABLE 5

Serum S protein after second administration

| Comp No. | Molar ratio in Formulation | N/P | Route | OD 450 nm-630 nm |
|---|---|---|---|---|
| SM-102 | 1.40:11.15:38.95:48.50 | 10 | IM | 1.64 |
| Naked Spike mRNA | — | — | IM | 0.62 |
| PBS Buffer | — | — | IM | 0.14 |
| L0186 | 1.40:11.15:38.95:48.50 | 18 | IM | 1.70 |
| L0187 | 1.40:11.15:38.95:48.50 | 20 | IM | 1.70 |
| L0192 | 2.00:4.00:59.00:35.00 | 35 | IM | 1.68 |
| L0199 | 1.50:16.00:34.00:48.50 | 55 | IV | 1.52 |
| L0200 | 1.00:7.00:57.00:35.00 | 35 | IV | 1.61 |
| L0203 | 1.40:11.15:38.95:48.50 | 30 | IM | 1.72 |

These results demonstrate that the tested compounds had excellent effective serum transduction efficiencies.

Unless otherwise defined, all technical and scientific terms used herein have the same meaning as commonly understood by one of ordinary skill in the art to which this disclosure belongs.

This disclosure illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims.

Thus, it should be understood that although the present disclosure has been specifically disclosed by certain embodiments and optional features, modification, improvement and variation of the disclosure embodied herein disclosed may be resorted to by those skilled in the art, and that such modifications, improvements and variations are considered to be within the scope of this disclosure. The materials, methods, and examples provided here are representative, and are not intended as limitations.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A compound of Formula I:

I

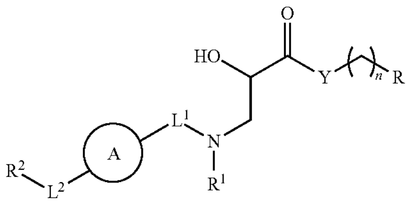

or a pharmaceutically acceptable salt, stereoisomer, or mixture of stereoisomers thereof, wherein:

Ring A is $C_{3-10}$ cycloalkyl, heterocyclyl, aryl, or heteroaryl;

$L^1$ is a bond or $C_{1-10}$ alkylene;

$L^2$ is a bond or $C_{1-10}$ alkylene;

$R^1$ is hydrogen, $C_{1-20}$ alkyl, $C_{2-20}$ alkenyl, $C_{2-20}$ alkynyl, $C_{2-20}$ heteroalkyl,

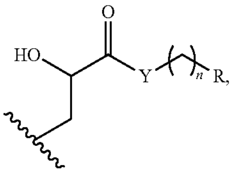

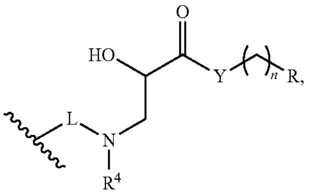 or

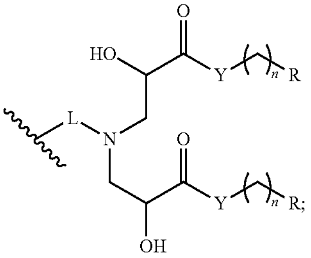

wherein the $C_{1-20}$ alkyl, $C_{2-20}$ alkenyl, $C_{2-20}$ alkynyl, or $C_{2-20}$ heteroalkyl is independently optionally substituted with one to five halo, cyano, —$OR^4$, —$SR^4$, —$NR^4_2$, —$N(R^4)_3^+$, oxo, $C_{1-6}$ alkyl, $C_{2-6}$ alkenyl, $C_{2-6}$ alkynyl, or $C_{1-6}$ haloalkyl;

$R^2$ is

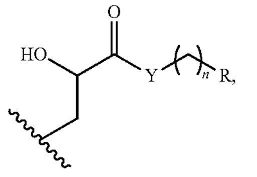
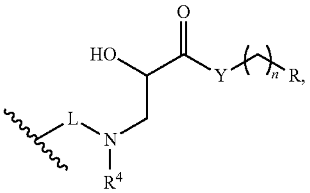
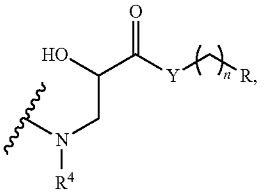
or
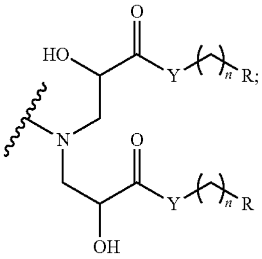

L is $C_{1-10}$ alkylene or $C_{3-10}$ heteroalkylene;

each $R^4$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —$SR^5$, —$NR^5_2$, —$N(R^5)_3^+$, or oxo;

each $R^5$ is independently hydrogen, $C_{1-12}$ alkyl, $C_{2-12}$ alkenyl, or $C_{2-12}$ alkynyl; wherein each $C_{1-12}$ alkyl, $C_{2-12}$ alkenyl, or $C_{2-12}$ alkynyl is independently optionally substituted with one to five halo, cyano, —OH, —SH, —$NH_2$, —NH($C_{1-6}$ alkyl), —N($C_{1-6}$ alkyl)$_2$, —N($C_{1-6}$ alkyl)$_3^+$, or oxo;

each Y is independently —O—, —NH—, or —$NR^7$—;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —NH($C_{1-6}$ alkyl), —N($C_{1-6}$ alkyl)$_2$, —N($C_{1-6}$ alkyl)$_3^+$, oxo, $C_{1-6}$ alkoxy, or $C_{1-6}$ haloalkoxy;

each n is independently an integer from 1-20;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2NR^4$—, each $Z^1$ is independently —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2NR^4$—; and provided that each

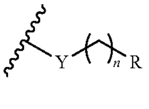

moiety comprises at least 6 linear atoms.

2. The compound of claim 1, or a pharmaceutically acceptable salt, stereoisomer, or mixture of stereoisomers thereof, wherein:

Ring A is $C_{3-10}$ cycloalkyl, heterocyclyl, aryl, or heteroaryl;

$L^1$ is a bond or $C_{1-10}$ alkylene;

$L^2$ is a bond or $C_{1-10}$ alkylene;

$R^1$ is hydrogen,

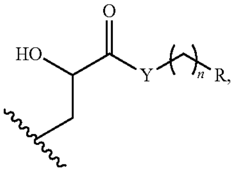
or
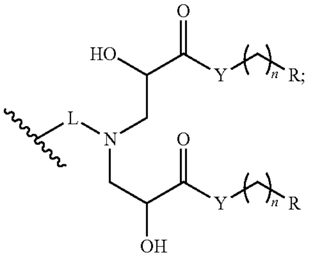

$R^2$ is

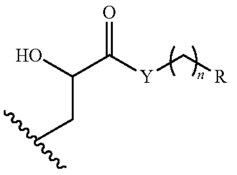
or
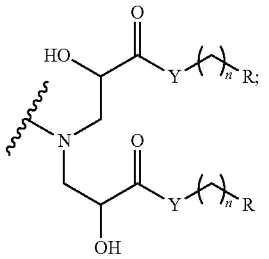

L is $C_{1-10}$ alkylene or $C_{3-10}$ heteroalkylene;

each $R^4$ is independently hydrogen, $C_{1-12}$ alkyl, $C_{2-12}$ alkenyl, or $C_{2-12}$ alkynyl;

each Y is independently —O—, —NH—, or —$NR^7$—;

each n is independently an integer from 1-20;

each $R^7$ is independently $C_{1-6}$ alkyl, $C_{2-6}$ alkenyl, $C_{2-6}$ alkynyl, or $C_{1-6}$ haloalkyl; wherein each $C_{1-6}$ alkyl, $C_{2-6}$ alkenyl, $C_{2-6}$ alkynyl, or $C_{1-6}$ haloalkyl is independently optionally substituted with one to five halo, cyano, —OH, —$NH_2$, —NH($C_{1-6}$ alkyl), —N($C_{1-6}$ alkyl)$_2$, —N($C_{1-6}$ alkyl)$_3^+$, oxo, $C_{1-6}$ alkoxy, or $C_{1-6}$ haloalkoxy;

each R is independently hydrogen, —Z—$C_{1-20}$ alkyl, —Z—$C_{2-20}$ alkenyl, —Z—$C_{2-20}$ alkynyl, —$Z^1$—$C_{1-6}$ alkylene-Z—$C_{1-20}$ alkyl, —$Z^1$—$C_{1-6}$ alkylene-Z—$C_{2-20}$ alkenyl, —$Z^1$—$C_{1-6}$ alkylene-Z—$C_{2-20}$ alkynyl, —$Z^1$—$C_{2-6}$ alkenyl-Z—$C_{1-20}$ alkyl, —$Z^1$—$C_{2-6}$ alkenyl-Z—$C_{2-20}$ alkenyl, —$Z^1$—$C_{2-6}$ alkenyl-Z—$C_{2-20}$ alkynyl, —$Z^1$—$C_{2-6}$ alkynyl-Z—$C_{1-20}$ alkyl, —$Z^1$—$C_{2-6}$ alkynyl-Z—$C_{2-20}$ alkenyl, or —$Z^1$—$C_{2-6}$ alkynyl-Z—$C_{2-20}$ alkynyl;

each Z is independently a bond, —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2NR_4$—;

each $Z^1$ is independently —O—, —$NR^4$—, —S—, —S—S—, —C(O)—, —OC(O)—, —C(O)O—, —C(O)$NR^4$—, —S(O)—, —S(O)$_2$—, —$NR^4$C(O)—, —$NR^4$C(O)O—, —$NR^4$C(O)$NR^4$—, —$NR^4$S(O)—, or —S(O)$_2NR^4$—, and provided that each

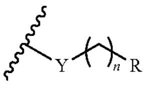

moiety comprises at least 6 linear atoms.

3. The compound of claim 1, wherein the compound is represented by Formula IA:

IA

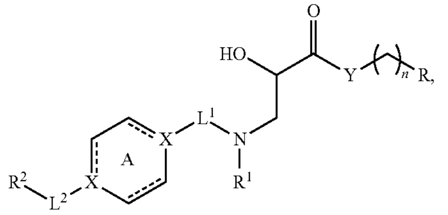

or a pharmaceutically acceptable salt, stereoisomer, or mixture of stereoisomers thereof, wherein:

each X is independently CH or N, and each bond represents a single bond; or each X is C, and each bond represents a double bond;

$L^1$ is a bond or $C_{1-10}$ alkylene; provided that when $L^1$ is a bond, then the X bonded thereto is a carbon atom; and $L^2$ is a bond or $C_{1-10}$ alkylene; provided that when $L^2$ is a bond, then the X—$R^2$ bond is not a N—N bond.

4. The compound of claim 1, wherein Ring A is

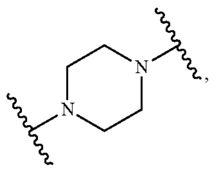
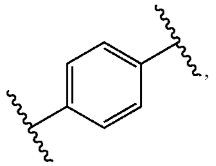
or
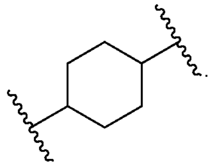

5. The compound of claim 1, wherein each n is independently an integer from 2-12.

6. The compound of claim 1, wherein Y is O or NH.

7. The compound of claim 1, wherein $L^1$ is $C_{1-10}$ alkylene.

8. The compound of claim 7, wherein $L^1$ is ethylene, propylene, or butylene.

9. The compound of claim 1, wherein $L^2$ is $C_{1-10}$ alkylene.

10. The compound of claim 9, wherein $L^2$ is ethylene, propylene, or butylene.

11. The compound of claim 1, wherein $R^1$ is hydrogen,

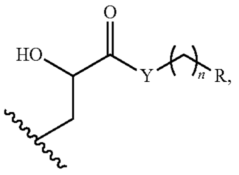
or
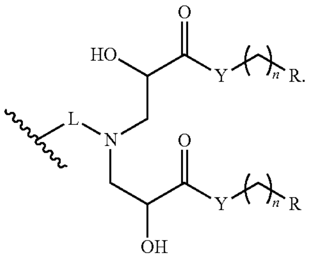

12. The compound of claim 11, wherein L is $C_{1-10}$ alkylene.

13. The compound of claim 12, wherein L is ethylene, propylene, or butylene.

14. The compound of claim 1, wherein $R^2$ is

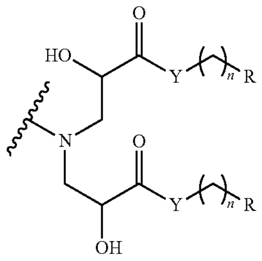
or
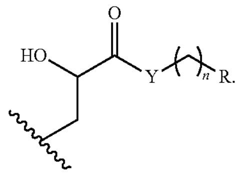

15. The compound of claim 1, which is of a formula selected from the group consisting of

IIA

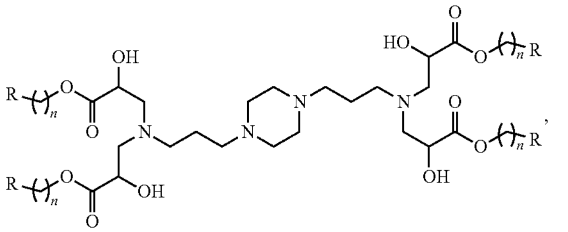

IIB

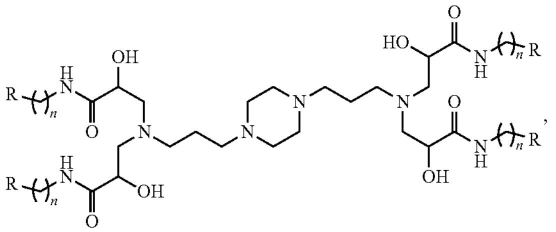

-continued
IIIA
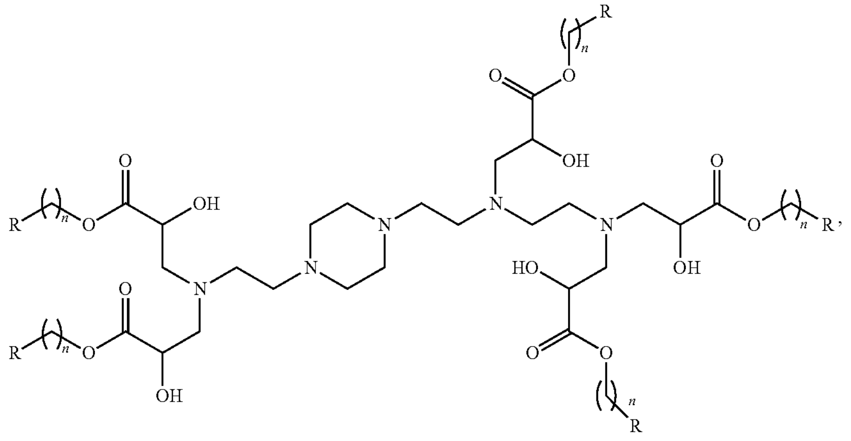
IIIB
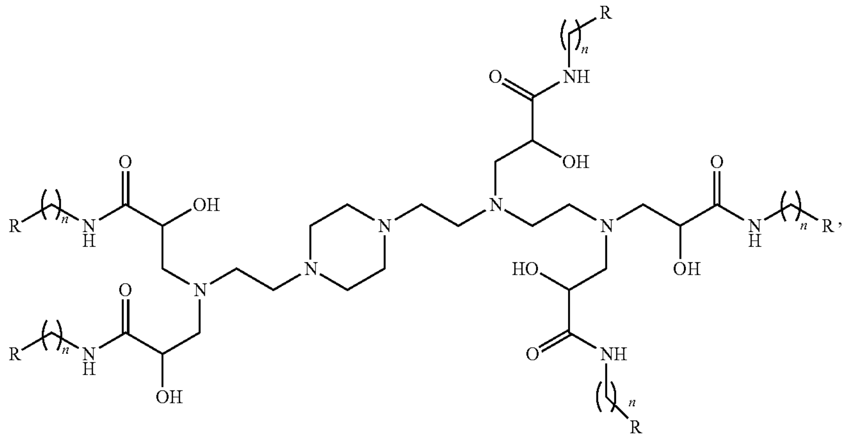
IVA
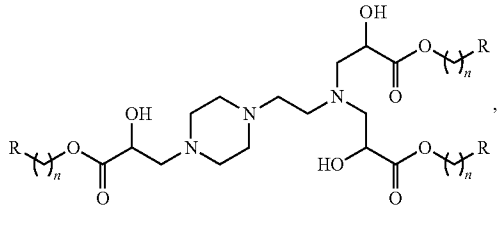
, and
IVB
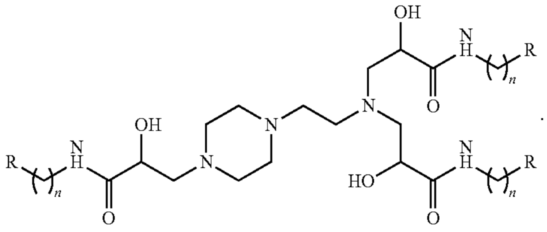
.
16. The compound of claim 1, wherein R is hydrogen, —Z—$C_{1-20}$ alkyl, —$Z^1$—$C_{1-6}$ alkylene-Z—$C_{1-12}$ alkyl, or —$Z^1$—$C_{1-6}$ alkylene-Z—$C_{2-12}$ alkenyl.
17. The compound of claim 1, wherein the moiety
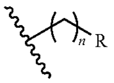
is selected from the group consisting of
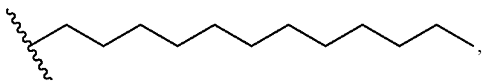
,
-continued
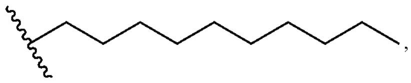
,
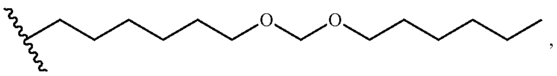
,
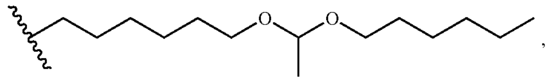
,
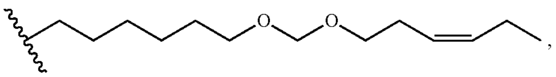
,
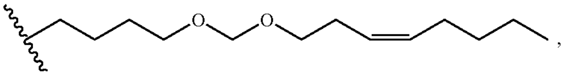
, -continued
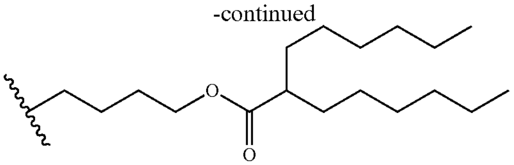,
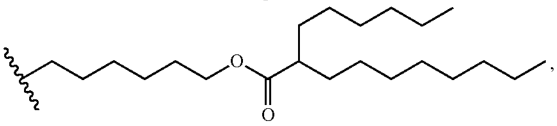,
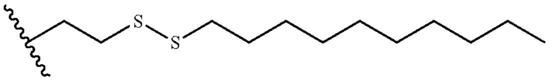,
-continued
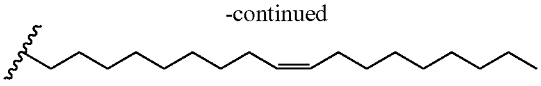,
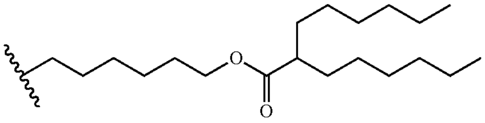, and
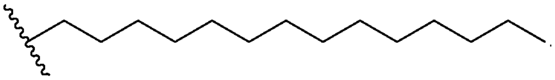.
18. The compound of claim 1, which is selected from the group consisting of
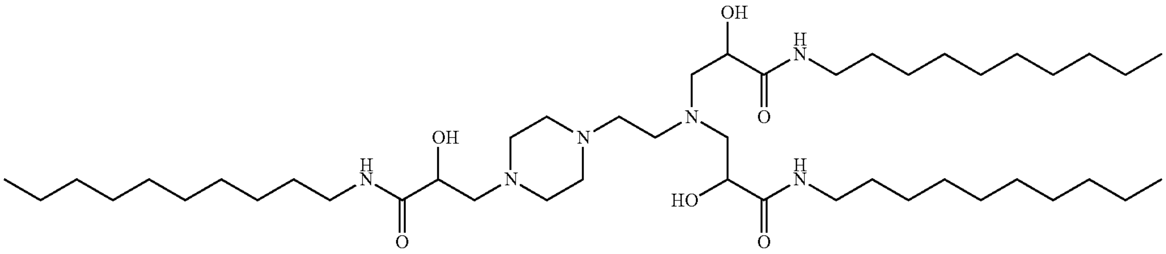,
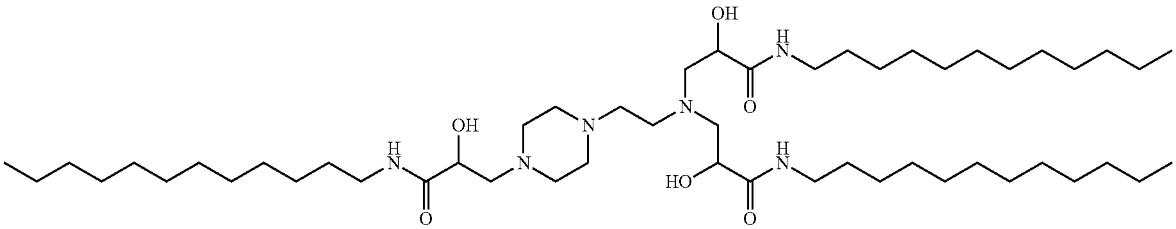,
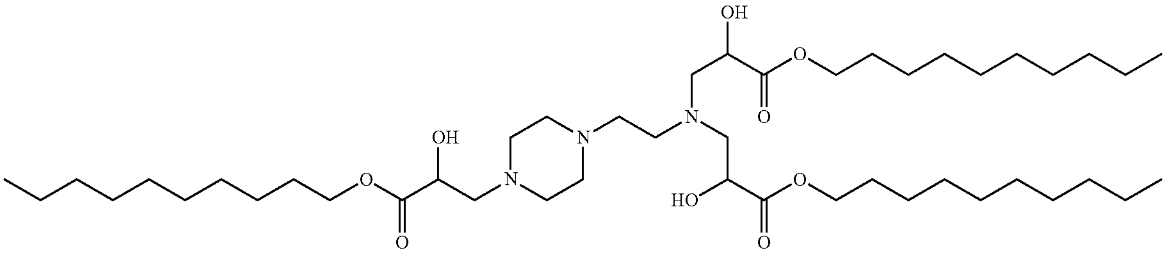,
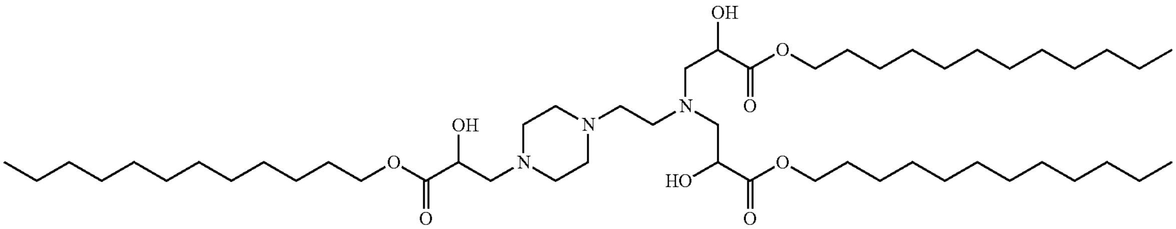,
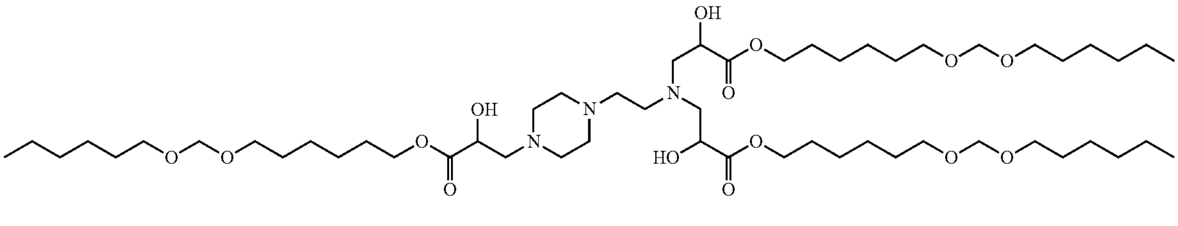, -continued
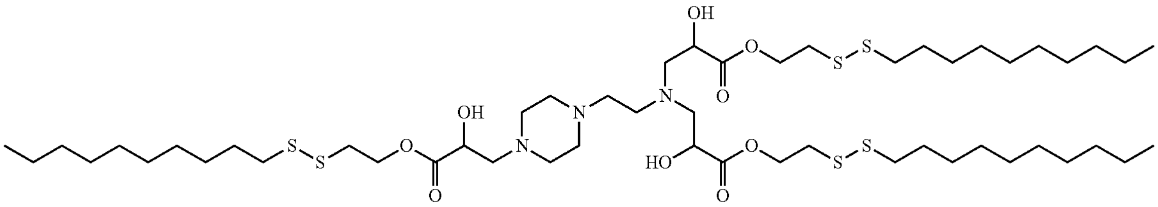
,
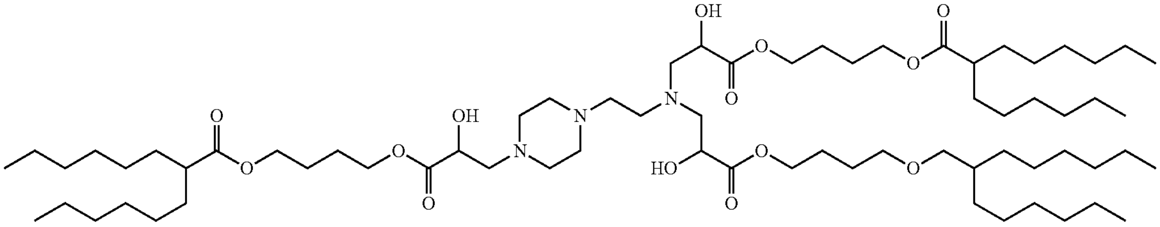
,
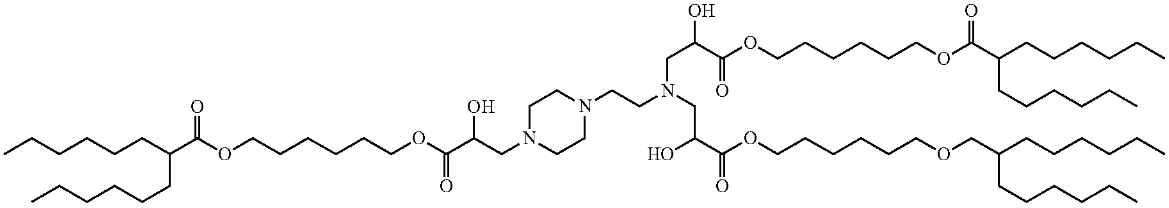
,
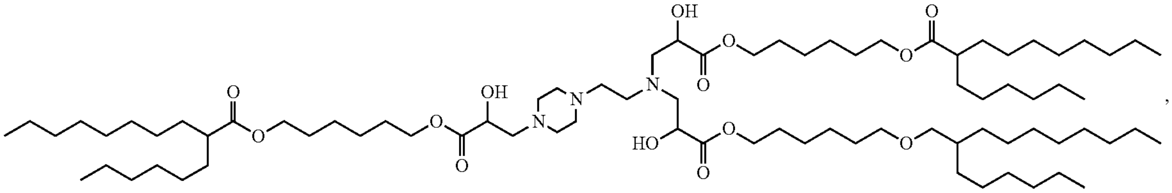
,
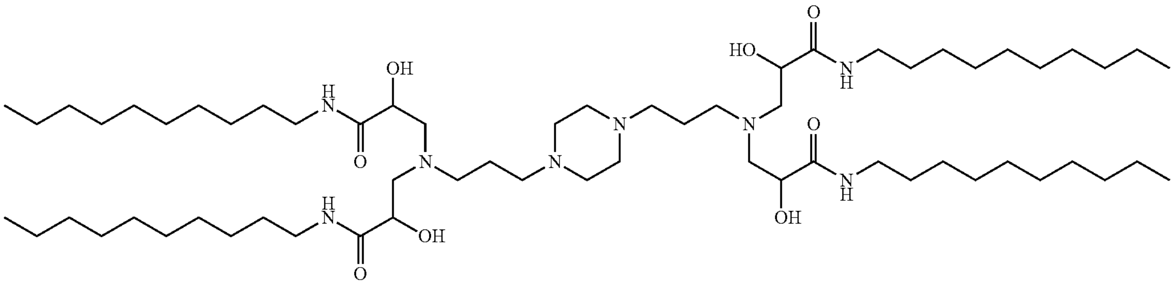
,
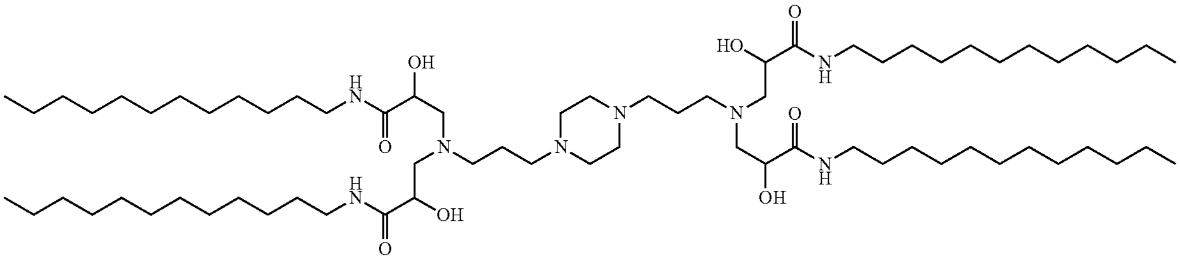
,
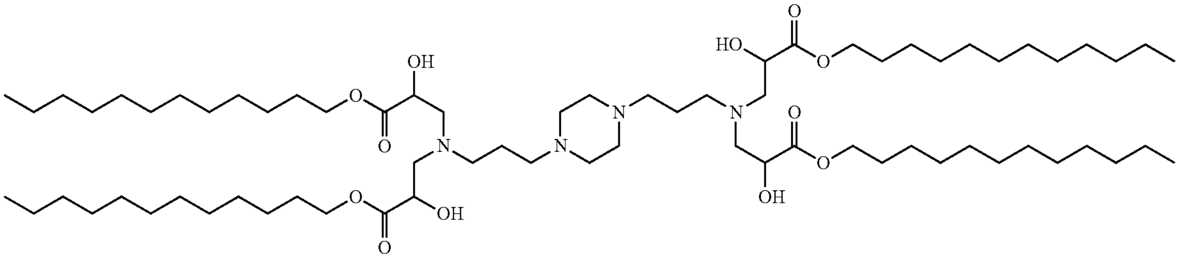
, -continued
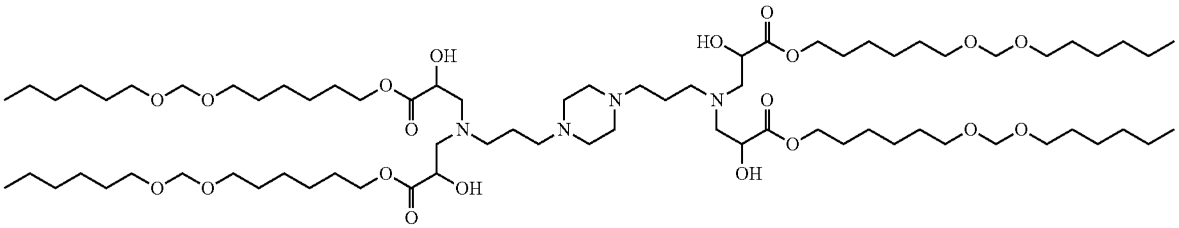
,
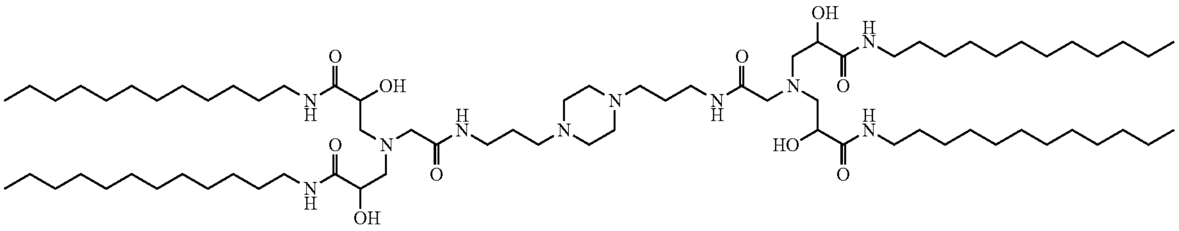
,
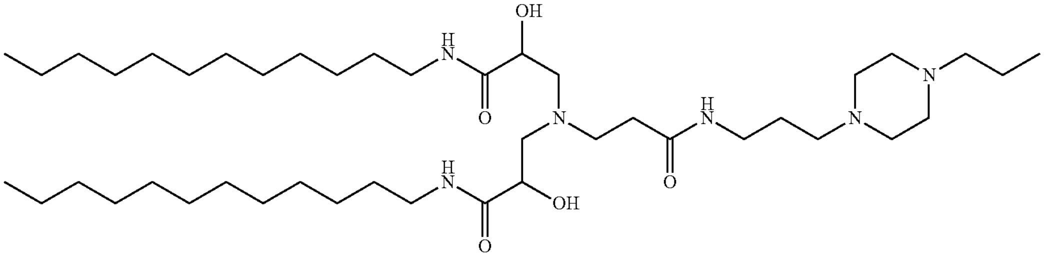
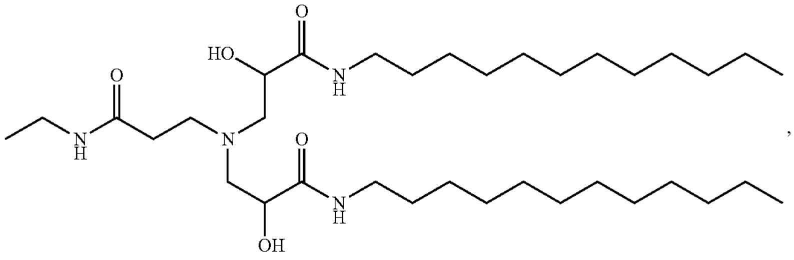
,
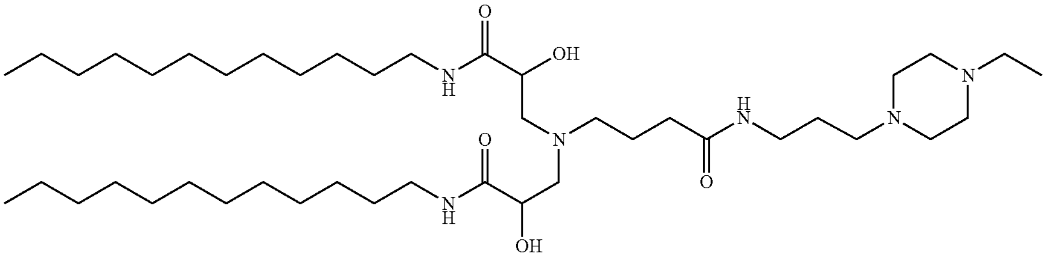
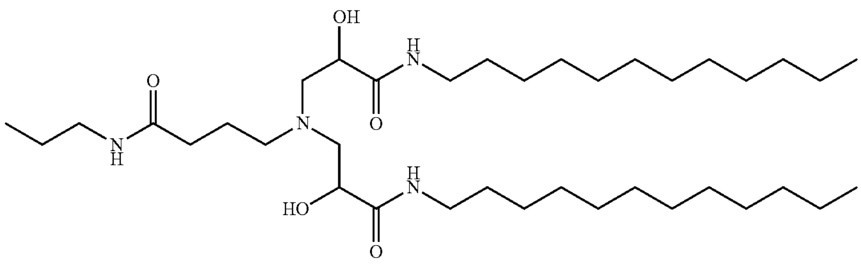
, -continued
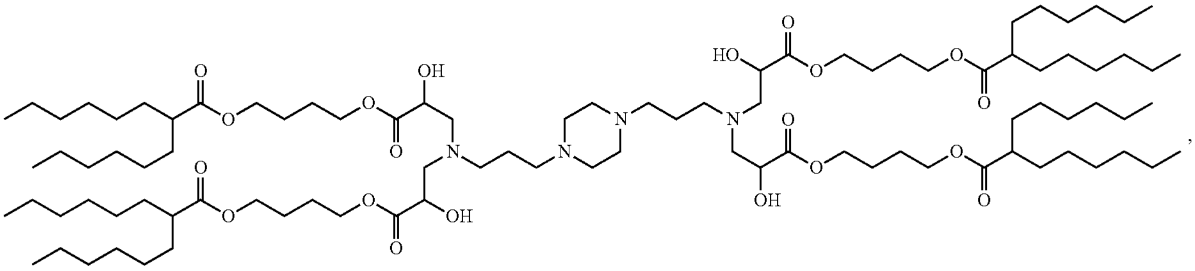
,
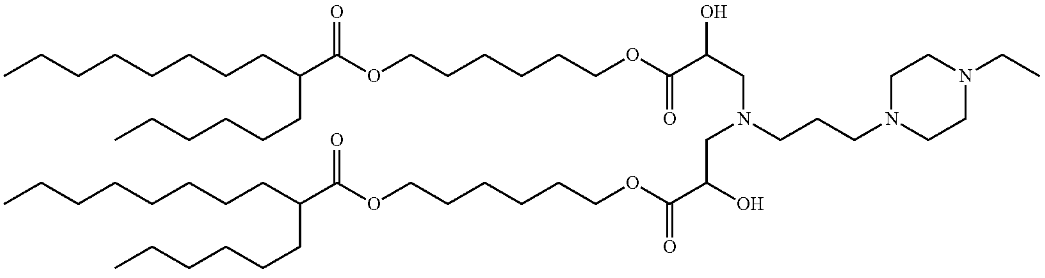
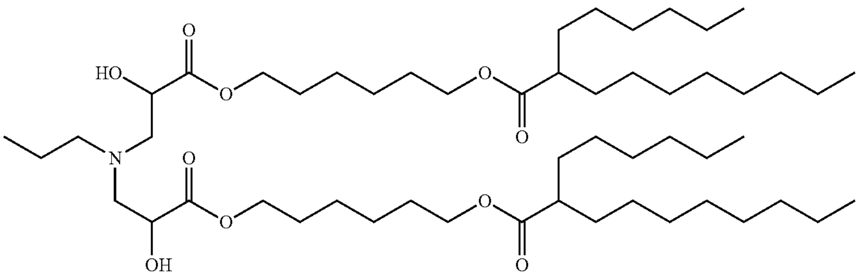
,
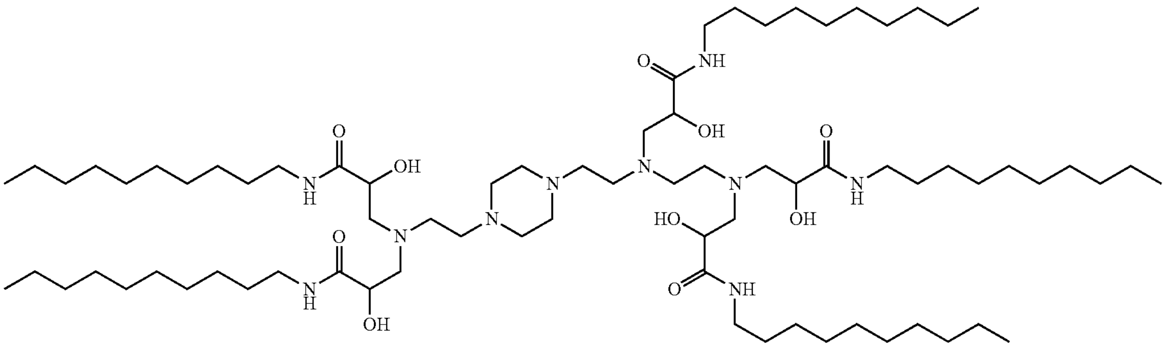
,
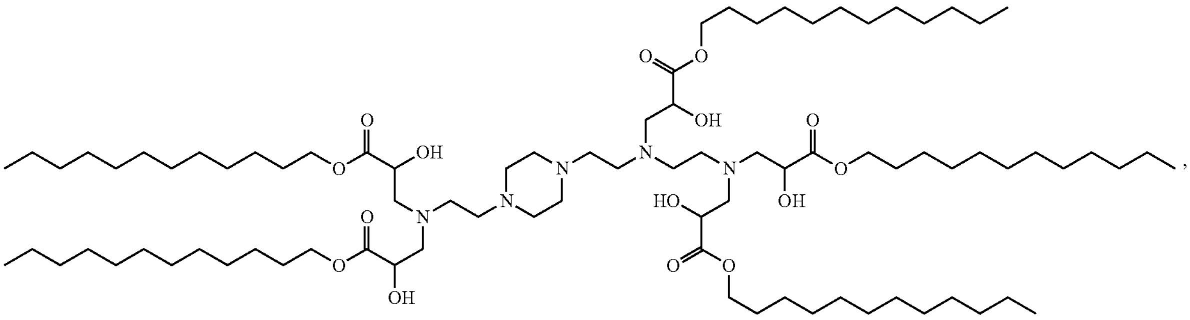
, -continued
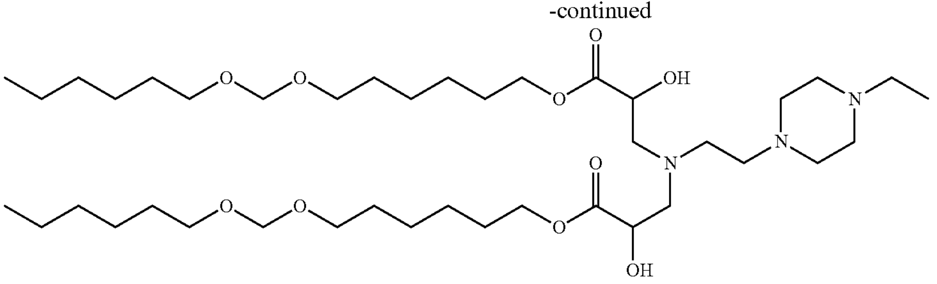
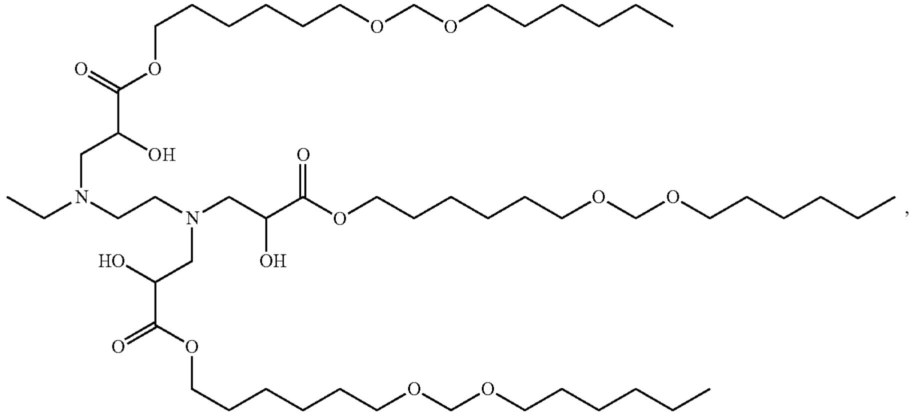
,
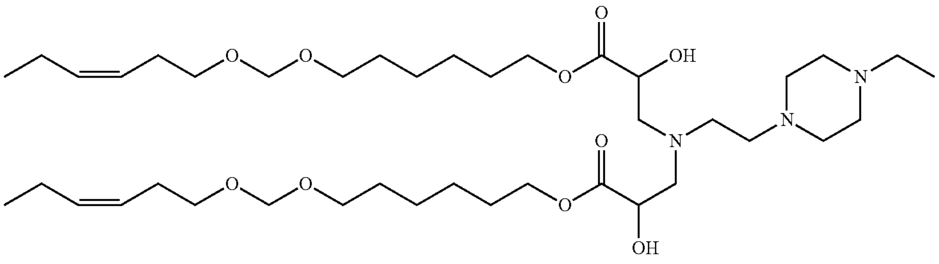
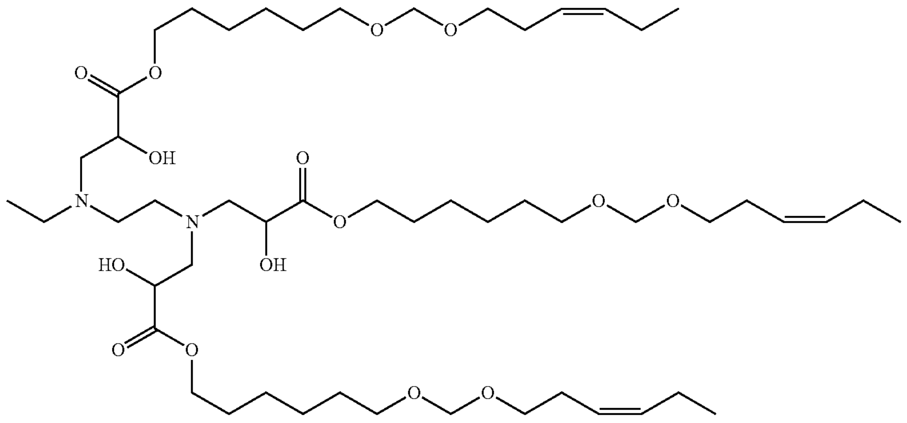
, -continued
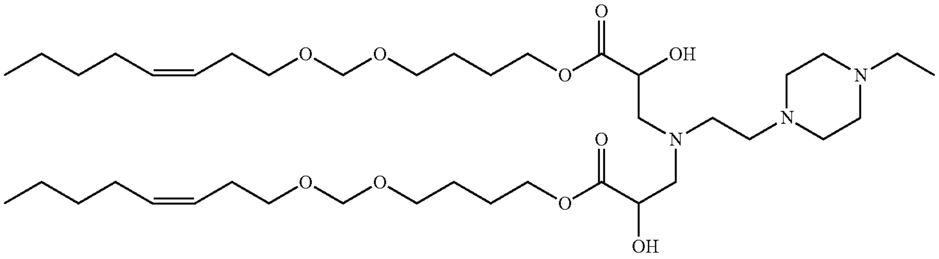
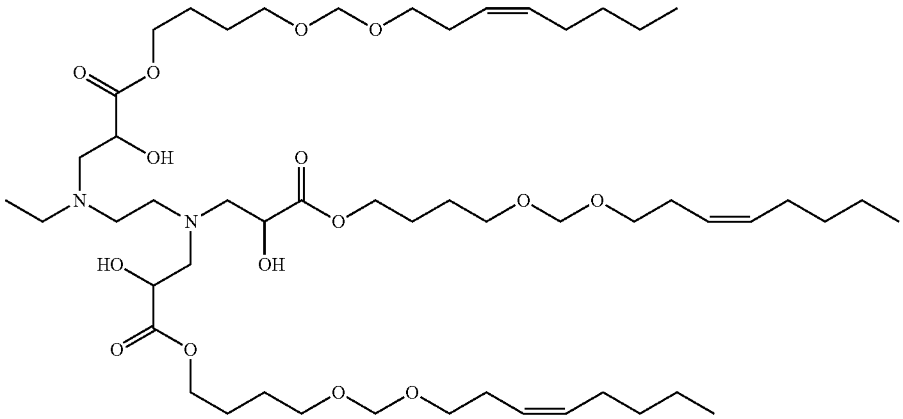
,
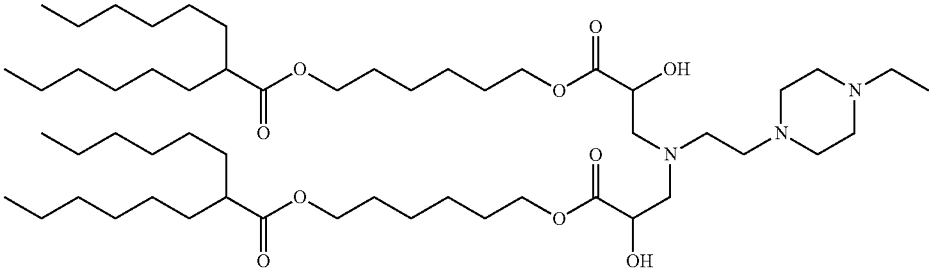
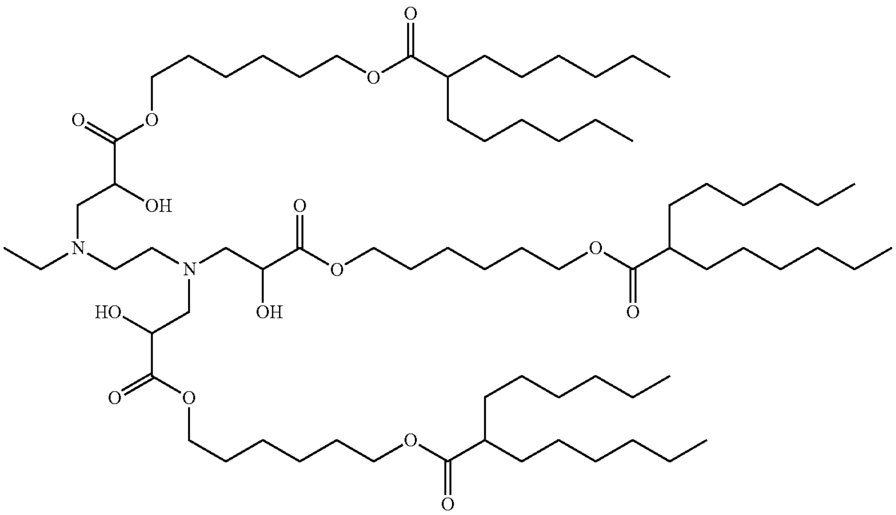
, -continued
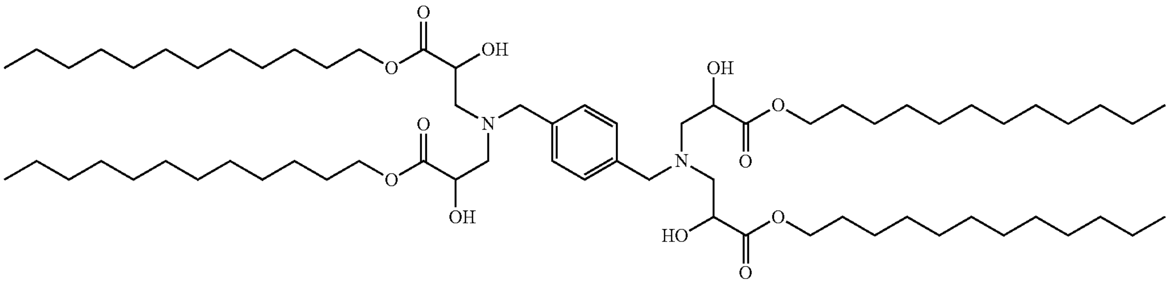
,
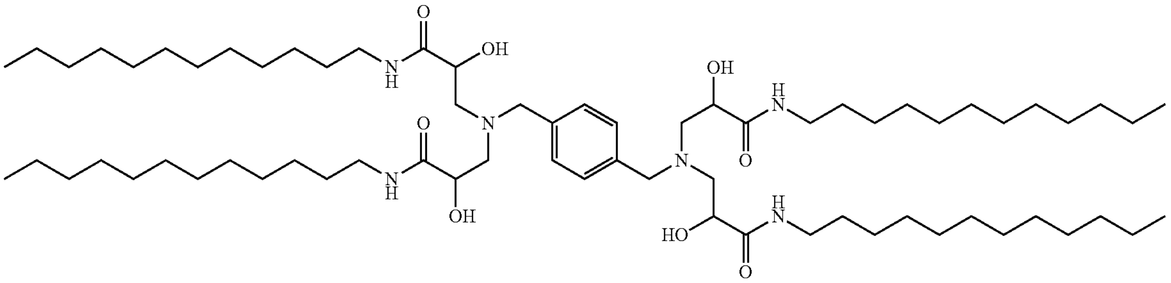
,
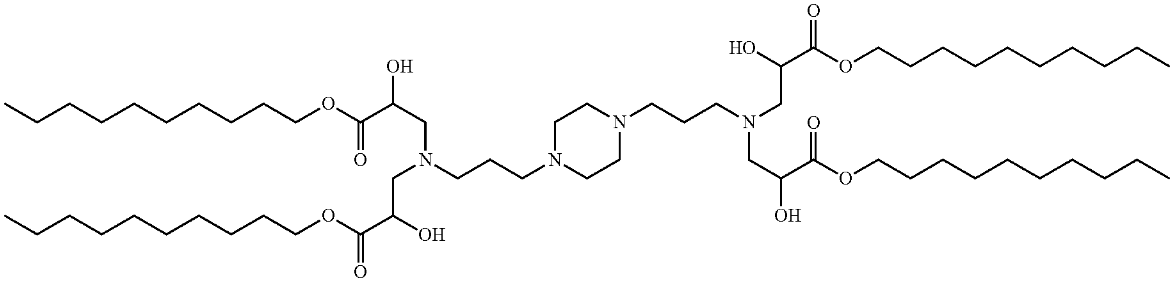
,
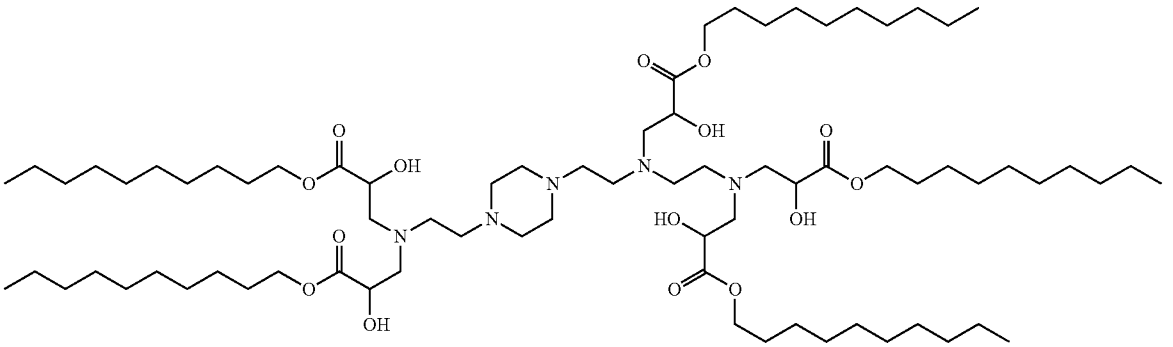
,
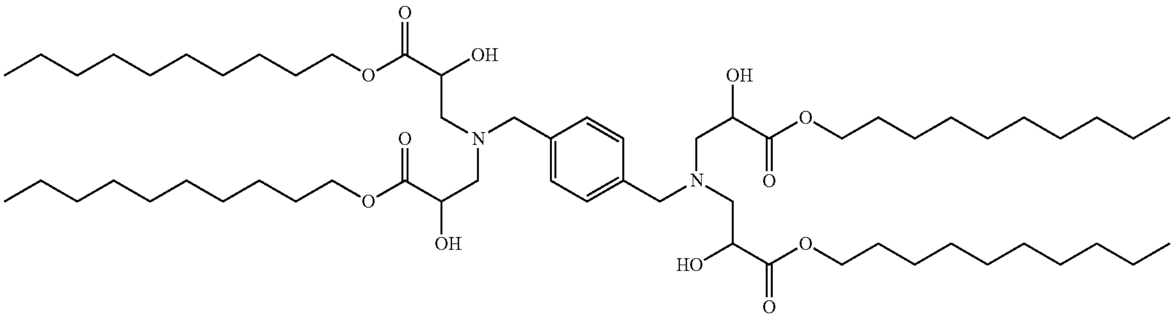
, -continued
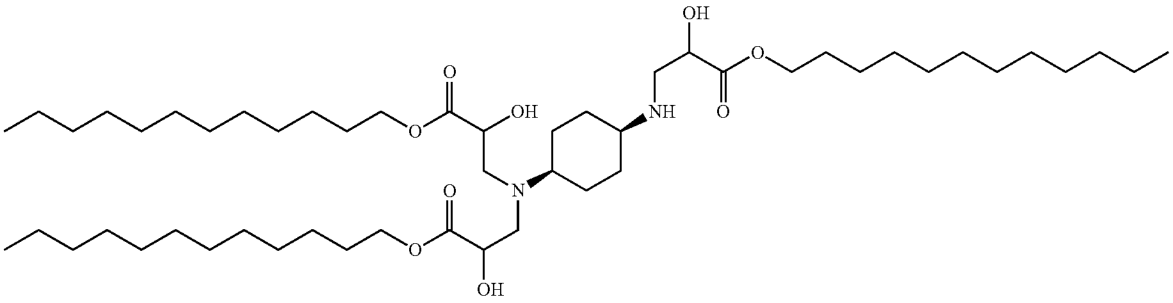
,
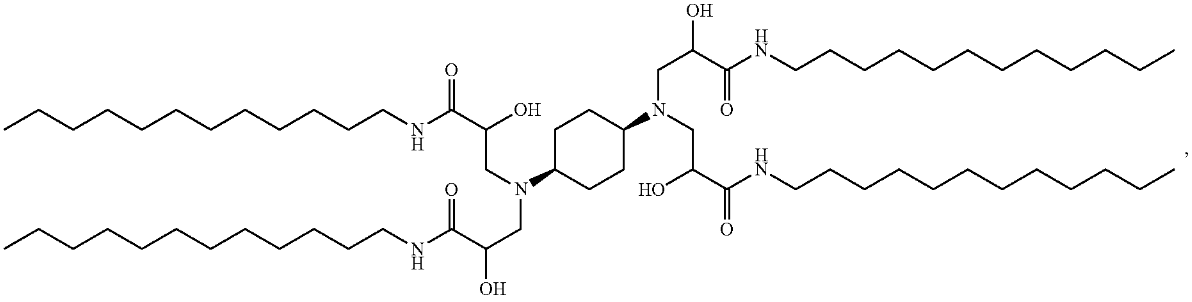
,
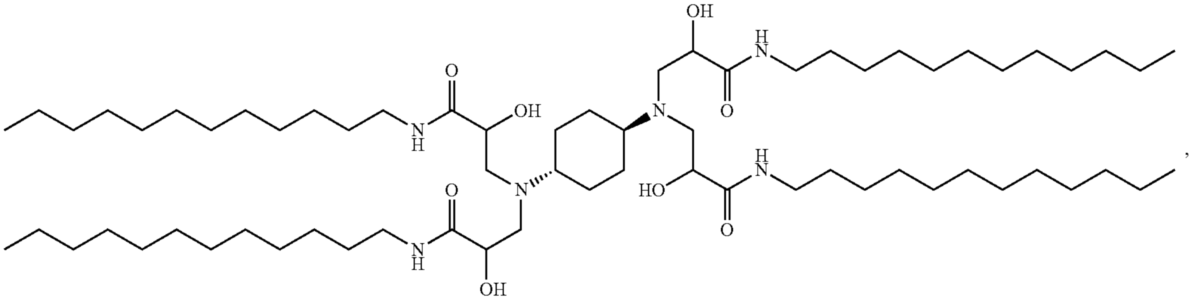
,
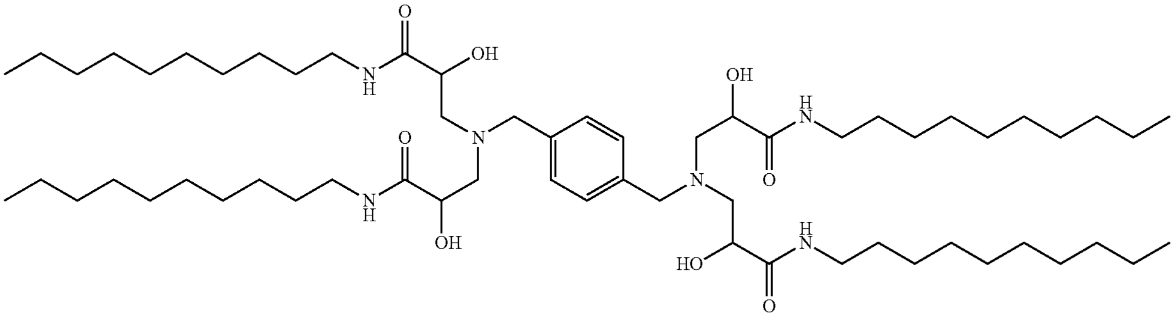
,
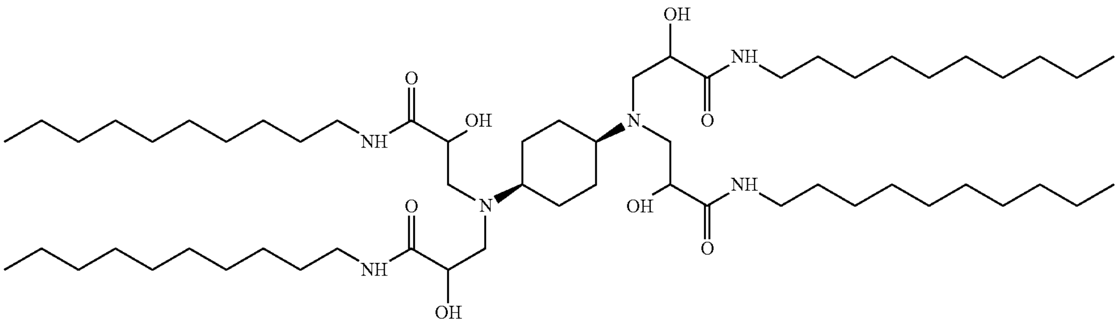
, -continued
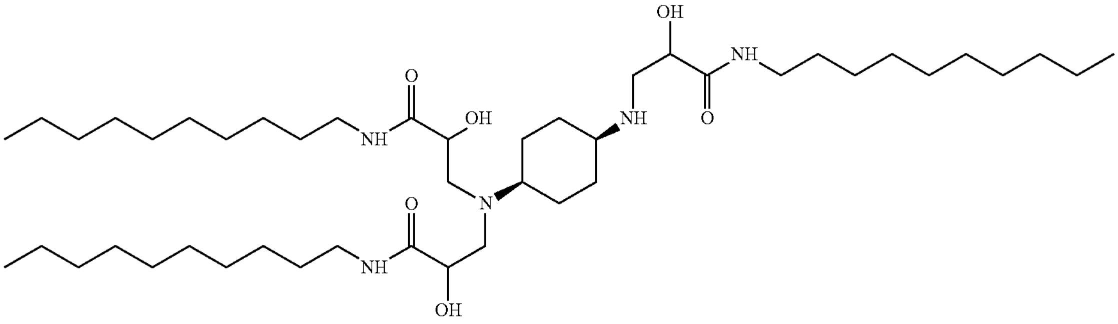
,
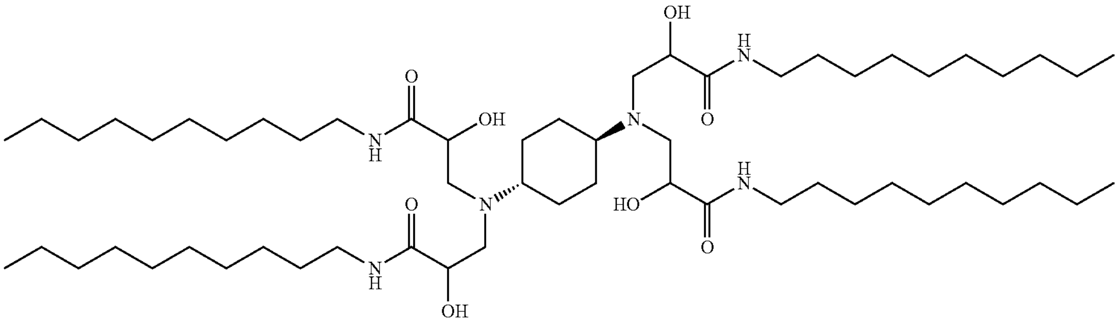
,
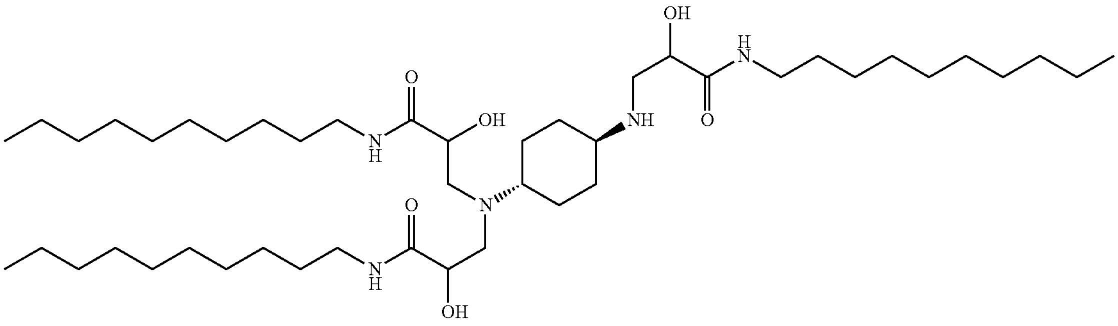
,
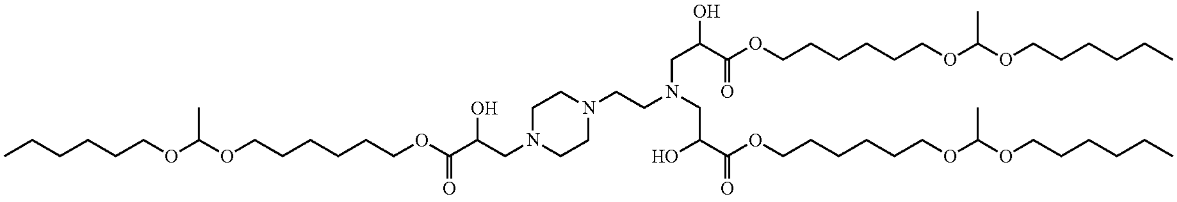
,
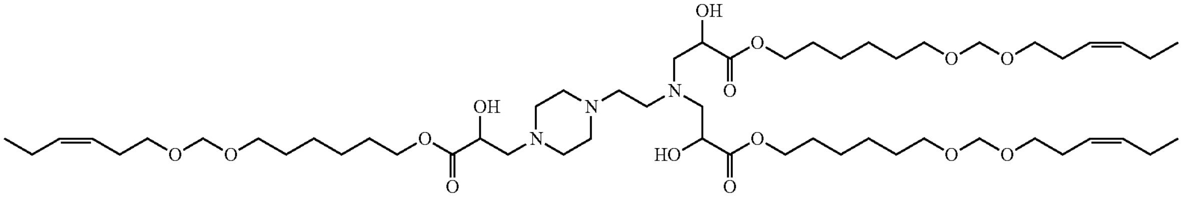
,
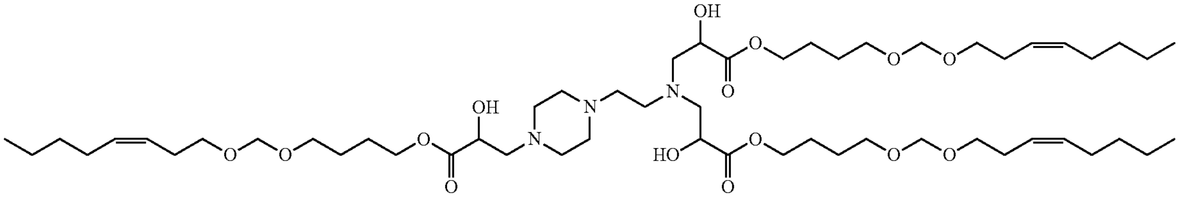
, -continued
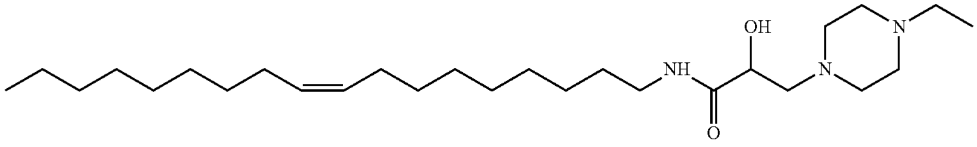
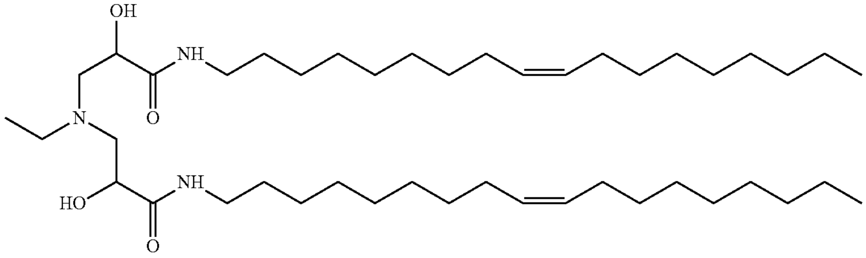
,
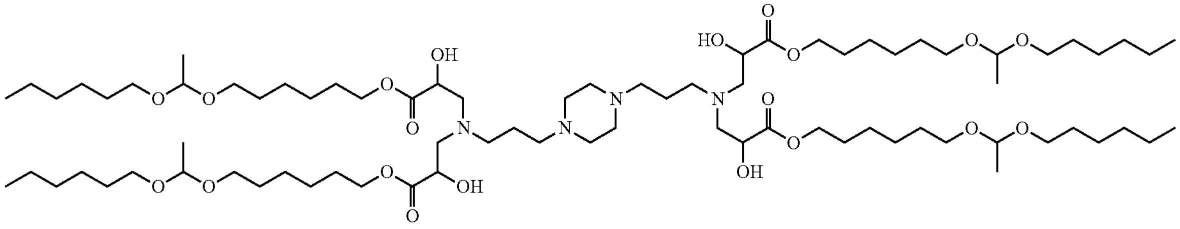
,
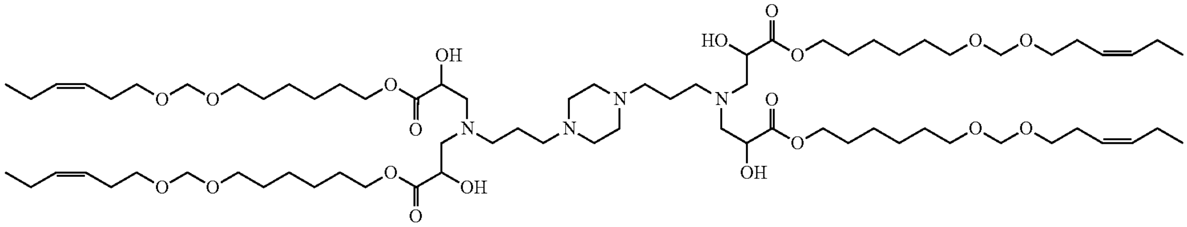
,
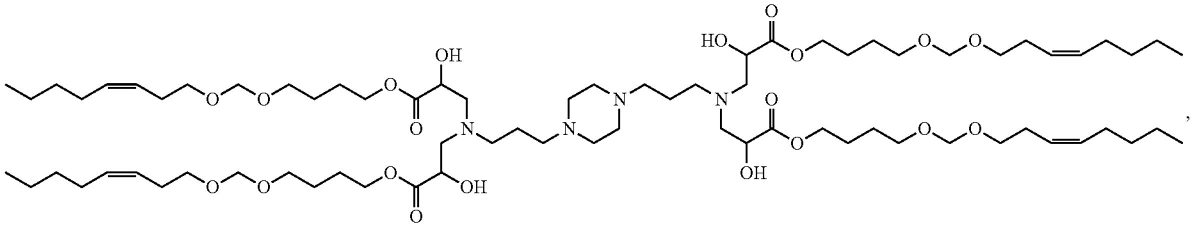
,
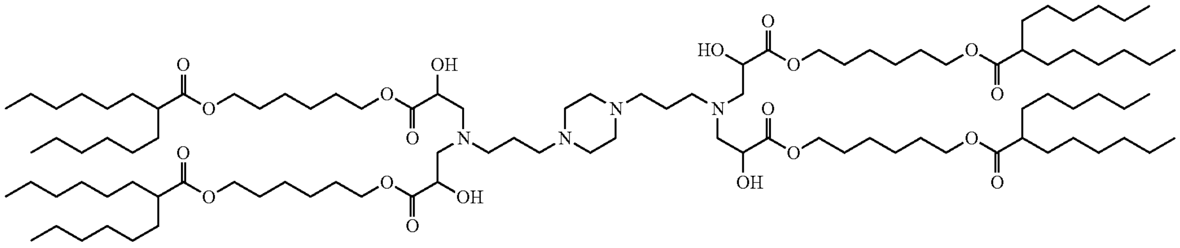
,
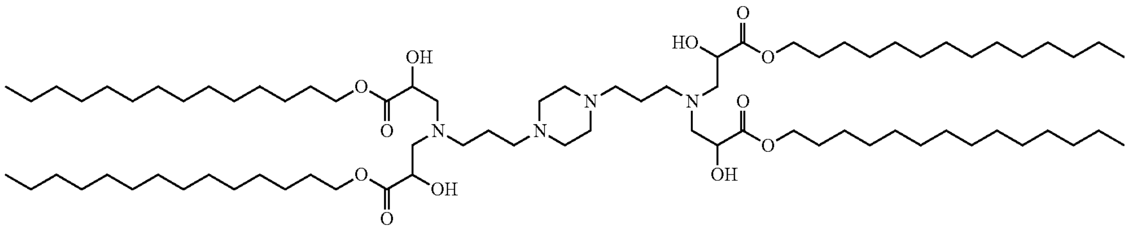
, and -continued
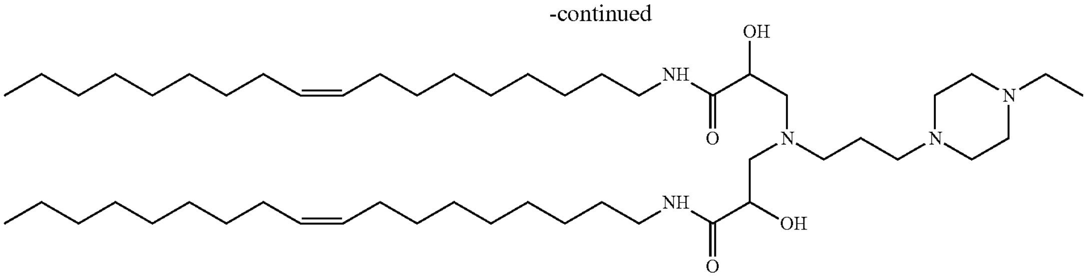
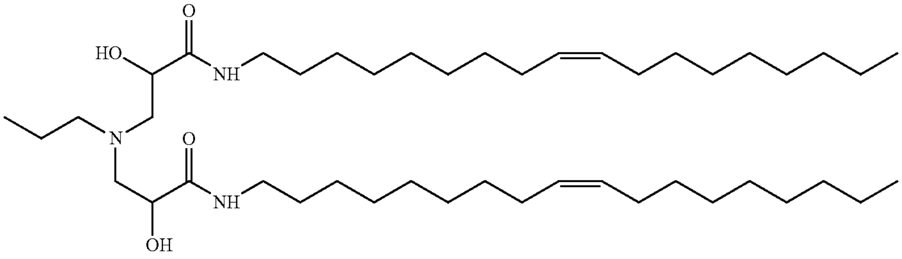
.
19. A composition comprising a compound of claim 1, a phospholipid, a structural lipid, and a polyethylene glycol (PEG) lipid.
20. A method of delivering a therapeutic or prophylactic agent to a mammalian cell, the method comprising contacting the cell with a composition of claim 19 that further comprises the therapeutic or prophylactic agent.
* * * * *